(12) United States Patent
Hauser et al.

(10) Patent No.: US 10,286,110 B2
(45) Date of Patent: *May 14, 2019

(54) CROSSLINKED PEPTIDE HYDROGELS

(71) Applicant: Agency for Science, Technology and Research, Singapore (SG)

(72) Inventors: Charlotte Hauser, Singapore (SG); Wei Yang Seow, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/398,288

(22) Filed: Jan. 4, 2017

(65) Prior Publication Data

US 2017/0182218 A1    Jun. 29, 2017

Related U.S. Application Data

(60) Division of application No. 14/634,559, filed on Feb. 27, 2015, which is a division of application No. 13/751,295, filed on Jan. 28, 2013, now Pat. No. 8,999,916, which is a continuation-in-part of application No. 13/638,152, filed as application No. PCT/SG2010/000469 on Dec. 15, 2010, now Pat. No. 9,067,084.

(60) Provisional application No. 61/319,838, filed on Mar. 31, 2010.

(51) Int. Cl.
| | | |
|---|---|---|
| A61K 38/00 | (2006.01) |
| A01N 25/00 | (2006.01) |
| A61K 47/00 | (2006.01) |
| C12N 5/00 | (2006.01) |
| C12N 5/02 | (2006.01) |
| A61L 27/38 | (2006.01) |
| A61K 47/42 | (2017.01) |
| A61K 38/02 | (2006.01) |
| A61L 27/22 | (2006.01) |
| A61L 27/50 | (2006.01) |
| A61L 27/52 | (2006.01) |
| A61L 26/00 | (2006.01) |
| A61K 9/06 | (2006.01) |
| A61K 35/33 | (2015.01) |
| C12N 5/071 | (2010.01) |

(52) U.S. Cl.
CPC ............ *A61L 27/3804* (2013.01); *A61K 9/06* (2013.01); *A61K 35/33* (2013.01); *A61K 38/02* (2013.01); *A61K 47/42* (2013.01); *A61L 26/008* (2013.01); *A61L 26/0028* (2013.01); *A61L 26/0061* (2013.01); *A61L 27/22* (2013.01); *A61L 27/38* (2013.01); *A61L 27/50* (2013.01); *A61L 27/52* (2013.01); *C12N 5/0018* (2013.01); *C12N 5/0062* (2013.01); *C12N 5/0068* (2013.01); *C12N 5/0671* (2013.01); *C12N 5/0691* (2013.01); *A61L 2300/412* (2013.01); *A61L 2300/426* (2013.01); *A61L 2400/06* (2013.01); *A61L 2430/00* (2013.01); *A61L 2430/06* (2013.01); *A61L 2430/38* (2013.01); *C12N 2513/00* (2013.01); *C12N 2533/50* (2013.01); *C12N 2533/54* (2013.01); *C12N 2537/10* (2013.01)

(58) Field of Classification Search
None
See application file for complete search history.

(56) References Cited

U.S. PATENT DOCUMENTS

| | | |
|---|---|---|
| 5,256,287 A | 11/1993 | Baxter et al. |
| 5,723,129 A | 3/1998 | Potter et al. |
| 6,204,359 B1 | 3/2001 | Delaey et al. |
| 7,413,877 B2 | 8/2008 | Collier et al. |
| 8,999,916 B2 * | 4/2015 | Hauser .................. A61K 47/42 435/397 |
| 9,067,084 B2 | 6/2015 | Hauser et al. |

(Continued)

FOREIGN PATENT DOCUMENTS

| | | |
|---|---|---|
| WO | WO-2006/036826 A2 | 4/2006 |
| WO | WO-2009/005151 A1 | 1/2009 |

(Continued)

OTHER PUBLICATIONS

Anonymous, Technical Information: N-Terminal Acetylation and C-terminal Amidation of Pepties, Thermo Electron Corporation Brochure (2004).

(Continued)

*Primary Examiner* — Zachary J Miknis
(74) *Attorney, Agent, or Firm* — Choate, Hall & Stewart LLP

(57) ABSTRACT

The present invention relates to hydrogels comprising a plurality of amphiphilic peptides and/or peptoids capable of self-assembling into three-dimensional macromolecular nanofibrous networks, which entrap water and form said hydrogels, wherein at least a portion of said plurality of amphiphilic peptides and/or peptoids is chemically cross-linked. The present invention further relates to methods for preparing such hydrogels and to various uses of such hydrogels, e.g. as cell culture substrates, for drug and gene delivery, as wound dressing, as an implant, as an injectable agent that gels in situ, in pharmaceutical or cosmetic compositions, in regenerative medicine, in tissue engineering and tissue regeneration, or in electronic devices. It also relates to a method of tissue regeneration or tissue replacement using a hydrogel in accordance with the present invention.

18 Claims, 54 Drawing Sheets

Specification includes a Sequence Listing.

(56) References Cited

U.S. PATENT DOCUMENTS

| | | |
|---|---|---|
| 9,120,841 B2 | 9/2015 | Hauser et al. |
| 9,687,591 B2 | 6/2017 | Hauser et al. |
| 2002/0068346 A1 | 6/2002 | Krystek et al. |
| 2006/0084607 A1 | 4/2006 | Spirio et al. |
| 2007/0203062 A1 | 8/2007 | Ellis-Behnke et al. |
| 2010/0015197 A1 | 1/2010 | Rapaport |
| 2010/0291210 A1 | 11/2010 | Miyachi et al. |
| 2011/0293709 A1 | 12/2011 | Hantash |
| 2013/0023460 A1 | 1/2013 | Hauser et al. |
| 2013/0267455 A1 | 10/2013 | Hauser et al. |
| 2015/0273114 A1 | 10/2015 | Hauser et al. |
| 2015/0320908 A1 | 11/2015 | Hauser et al. |
| 2015/0367028 A1 | 12/2015 | Hauser et al. |
| 2017/0182113 A1* | 6/2017 | Hauser .................. A61K 38/02 |
| 2017/0182217 A1* | 6/2017 | Hauser ................ A61L 27/3804 |
| 2017/0182219 A1* | 6/2017 | Hauser ................ A61L 27/3804 |

FOREIGN PATENT DOCUMENTS

| | | |
|---|---|---|
| WO | WO-2009/039854 A2 | 4/2009 |
| WO | WO-2009/114815 A1 | 9/2009 |
| WO | WO-2009/132287 A2 | 10/2009 |
| WO | WO-2011/032181 A2 | 3/2011 |
| WO | WO-2011/116072 A1 | 9/2011 |
| WO | WO-2011/123061 A1 | 10/2011 |
| WO | WO-2013/0066274 A1 | 5/2013 |

OTHER PUBLICATIONS

Chao et al., Binding of uracil derivative to hydrophobic peptides and sodium dodecyl sulfate, J. Biol. Chem. 251:6924-6928, (1976).

International Search Report for PCT/SG2010/000469, 8 pages (dated Mar. 23, 2011).

Johnson, et al. Directed Self-Assembly of Dipeptides to Form Ultrathin Hydrogel Membranes, J. Am. Chem. Soc., 132: 5130-5136 (2010).

Koda, D. et al., Proteinase-mediated drastic morphological change of peptide-amphiphile to induce supramolecular hydrogelation, Chemical Communications, 46:979-981 (2010).

Measey, T. J. et al., Aggregation of the Amphipathic Peptides $(AAKA)_n$ into Antiparallel β-Sheets, Journal of the American Chemical Society, 128:13324-13325 (2006).

Mishra, A. et al., Ultrasmall natural peptides self-assemble to strong temperature-resistant helical fbers in scaffolds suitable for tissue engineering, Nano Today, 6: 232-239 (2011).

Pak et al., Binding effect and design of a competitive inhibitory peptide for HMG-CoA reductase through modeling of an active peptide backbone, Bioorgan & Med. Chem. 16:1309-1318, (2007).

Seow, W, and Hauser, C., Tunable Mechanical Properties of Ultrasmall Peptide Hydrogels by Crosslinking and Functionalization to Achieve the 3D Distribution of Cells, Advanced Healthcare Materials, 2: 1219-1223 (2013).

Supplementary European Search Report for EP14743041, 9 pages (dated Oct. 25, 2016).

Written Opinion for PCT/SG2010/000469, 10 pages (dated Mar. 23, 2011).

Yu-Lin, S. et al., Two-dimensional differentiation of neural stem cells induced by self-assembled hydrogel from IKVAV-containing peptide amphiphile, Journal of Clinical Rehabilitative Tissue Engineering Research, 13(34):6667-6670 (2009) (English Abstract).

Yulin, S. et al., Angiogenesis Induced with Neotype Amphiphic Peptide, Journal of Biomedical Engineering, 27(1):113-115 (2010) (English Abstract).

Vauthey et al., Molecular self-assembly of surfactant-like peptides to forma nanotubes and nanovesicles, Proc. Natl. Acad. Sci., 99: 5355-5360 (2002).

\* cited by examiner

Fig. 1A: SEVEN MEMBER PEPTIDES WITH ASPARTIC ACID HEAD GROUP

| SEQ ID No. | Peptide | Peptide sequence | Observation |
|---|---|---|---|
| 1 | Ac-LD$_7$ (L) | Ac-LIVAGDD-COOH (L) | Hydrogelation |

Fig. 1B: SIX MEMBER PEPTIDES WITH ASPARTIC ACID HEAD GROUP

| SEQ ID No. | Peptide | Peptide sequence | Observation |
|---|---|---|---|
| 2 | Ac-LD$_6$ (L) | Ac-LIVAGD-COOH (L) | Hydrogelation |
| 3 | Ac-LD$_6$ (D) | Ac-LIVAGD-COOH (D) | Hydrogelation |
| 4 | Ac-AD$_6$ (L) | Ac-AIVAGD-COOH (L) | Hydrogelation |
| 5 | Ac-AD$_6$ (D) | Ac-AIVAGD-COOH (D) | Hydrogelation |
| 6 | Ac-ID$_6$ (L) | Ac-ILVAGD-COOH (L) | Hydrogelation |
| 7 | Ac-ID$_6$ (D) | Ac-ILVAGD-COOH (D) | Hydrogelation |
| 8 | Ac-LD$_{6-1}$ (L) | Ac-LAVAGD-COOH (L) | Hydrogelation |
| 9 | Ac-LD$_{6-2}$ (L) | Ac-LIVAAD-COOH (L) | Hydrogelation |

Fig. 1C: SIX MEMBER PEPTIDES WITH SERINE HEAD GROUP

| SEQ ID No. | Peptide | Peptide sequence | Observation |
|---|---|---|---|
| 10 | Ac-LS$_6$ (L) | Ac-LIVAGS-COOH (L) | Hydrogelation |
| 10 | Ac-LS$_6$ (L) | Ac-LIVAGS-CONH$_2$ (L) | Hydrogelation |
| 11 | Ac-LS$_6$ (D) | Ac-LIVAGS-COOH (D) | Hydrogelation |
| 12 | Ac-AS$_6$ (L) | Ac-AIVAGS-COOH (L) | Hydrogelation |
| 12 | Ac-AS$_6$ (L) | Ac-AIVAGS-CONH$_2$ (L) | Hydrogelation |
| 13 | Ac-IS$_6$ (L) | Ac-ILVAGS-COOH (L) | Hydrogelation |

Fig. 1D: SIX MEMBER PEPTIDES WITH THREONINE HEAD GROUP

| SEQ ID No. | Peptide | Peptide sequence | Observation |
|---|---|---|---|
| 14 | Ac-LT$_6$ (L) | Ac-LIVAGT-COOH (L) | Hydrogelation |
| 14 | Ac-LT$_6$ (L) | Ac-LIVAGT-CONH$_2$ (L) | Hydrogelation |
| 15 | Ac-AT$_6$ (L) | Ac-AIVAGT-COOH (L) | Hydrogelation |
| 15 | Ac-AT$_6$ (L) | Ac-AIVAGT-CONH$_2$ (L) | Hydrogelation |

Fig. 1E: SEVEN MEMBER PEPTIDES WITH GLUTAMIC ACID HEAD GROUP

| SEQ ID No. | Peptide | Peptide sequence | Observation |
|---|---|---|---|
| 16 | Ac-LE$_7$ (L) | Ac-LIVAGEE-COOH (L) | Hydrogelation |

Fig. 1F: SIX MEMBER PEPTIDES WITH GLUTAMIC ACID HEAD GROUP

| SEQ ID No. | Peptide | Peptide sequence | Observation |
|---|---|---|---|
| 17 | Ac-LE$_6$ (L) | Ac-LIVAGE-COOH (L) | Hydrogelation |
| 18 | Ac-LE$_6$ (D) | Ac-LIVAGE-COOH (D) | Hydrogelation |

Fig. 1G: SIX MEMBER PEPTIDES WITH LYSINE HEAD GROUP

| SEQ ID No. | Peptide | Peptide sequence | Observation |
|---|---|---|---|
| 19 | Ac-LK$_6$ (L) | Ac-LIVAGK-CONH$_2$ (L) | Hydrogelation |

Fig. 1H: FIVE MEMBER PEPTIDES WITH ASPARTIC ACID HEAD GROUP

| SEQ ID No. | Peptide | Peptide sequence | Observation |
|---|---|---|---|
| 20 | Ac-LD$_{5-1}$ (L) | Ac-LIVAD-COOH (L) | Hydrogelation |
| 21 | Ac-LD$_{5-2}$ (L) | Ac-LIVGD-COOH (L) | Hydrogelation |

Fig. 1I: FOUR MEMBER PEPTIDES WITH ASPARTIC ACID HEAD GROUP

| SEQ ID No. | Peptide | Peptide sequence | Observation |
|---|---|---|---|
| 22 | Ac-ID$_4$ (L) | Ac-IVAD-COOH (L) | Hydrogelation |
| 23 | Ac-ID$_4$ (D) | Ac-IVAD-COOH (D) | Hydrogelation |

Fig. 1J: THREE MEMBER PEPTIDES WITH ASPARTIC ACID HEAD GROUP

| SEQ ID No. | Peptide | Peptide sequence | Observation |
|---|---|---|---|
| 24 | Ac-ID$_3$ (L) | Ac-IVD-COOH (L) | Hydrogelation |

Fig. 1K: SEVEN MEMBER PEPTIDES WITH ADDITIONAL CYSTEIN HEAD GROUP

| SEQ ID No. | Peptide | Peptide sequence | Observation |
|---|---|---|---|
| 43 | Ac-LK$_6$C (L) | Ac-LIVAGKC-COOH (L) | Hydrogelation |
| 44 | Ac-LS$_6$C (L) | Ac-LIVAGSC-COOH (L) | Hydrogelation |
| 45 | Ac-LD$_6$C (L) | Ac-LIVAGDC-COOH (L) | Hydrogelation |
| 46 | Ac-IK$_6$C (L) | Ac-ILVAGKC-COOH (L) | Hydrogelation |
| 47 | Ac-ID$_6$C (L) | Ac-ILVAGDC-COOH (L) | Hydrogelation |

Fig. 1L: SIX MEMBER PEPTIDES WITH CYSTEIN HEAD GROUP

| SEQ ID No. | Peptide | Peptide sequence | Observation |
|---|---|---|---|
| 48 | Ac-LC$_6$ (L) | Ac-LIVAGC-COOH (L) | Hydrogelation |
| 49 | Ac-AC$_6$ (L) | Ac-AIVAGC-COOH (L) | Hydrogelation |
| 50 | Ac-IC$_6$ (L) | Ac-ILVAGC-COOH (L) | Hydrogelation |

Fig. 1M: FOUR MEMBER PEPTIDES WITH ADDITIONAL CYSTEIN HEAD GROUP

| SEQ ID No. | Peptide | Peptide sequence | Observation |
|---|---|---|---|
| 51 | Ac-IK$_3$C (L) | Ac-IVKC-COOH (L) | Hydrogelation |
| 52 | Ac-ID$_3$C (L) | Ac-IVDC-COOH (L) | Hydrogelation |
| 53 | Ac-IS$_3$C (L) | Ac-IVSC-COOH (L) | Hydrogelation | a. Ac-LD-6 (L) 1mg/ml b. Ac-AD-6 (L) 5mg/ml a. Ac-AS-6 (L) 5mg/ml b. Ac-AS-6 (L) 10mg/ml c. Ac-AS-6 (L) 15mg/ml

ESEM image of ACLD6 (L) gels at magnification of 260X at 4 °C.

ESEM image of ACLD6 (L) gels at magnification of 1000X at 4 °C.

ESEM image of ACLD6 (L) gels at magnification of 2000X at 4 °C.

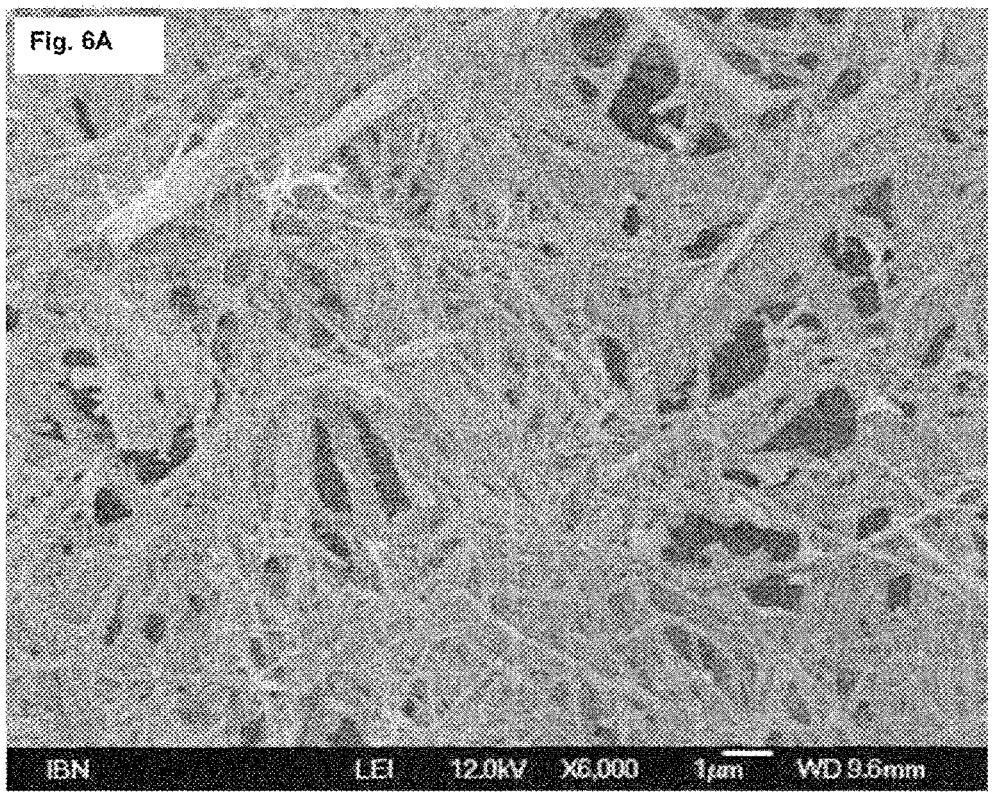

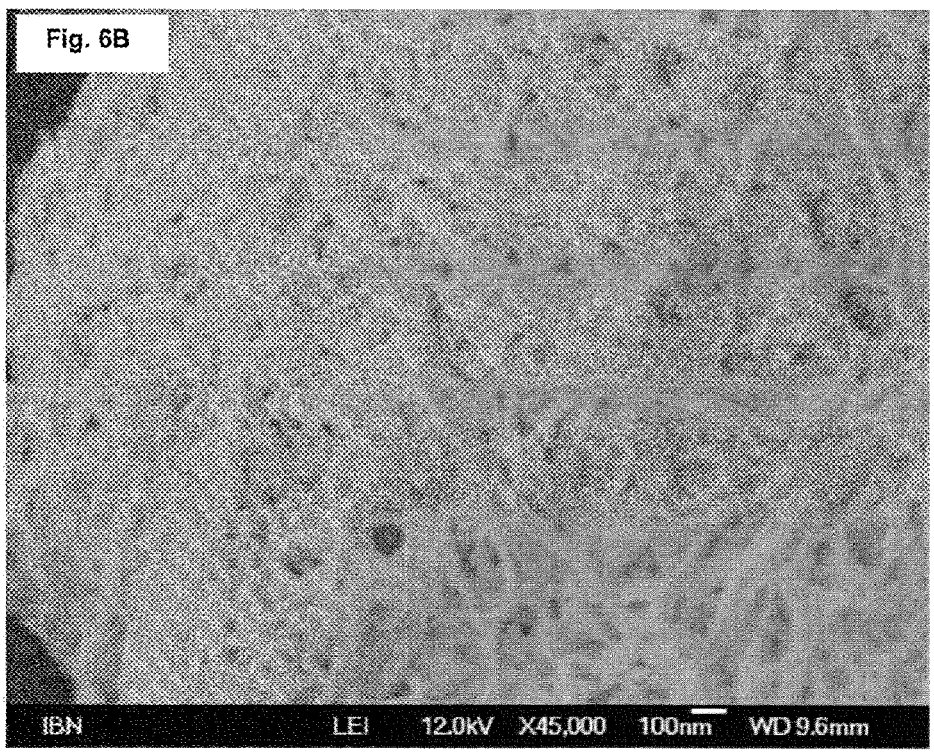

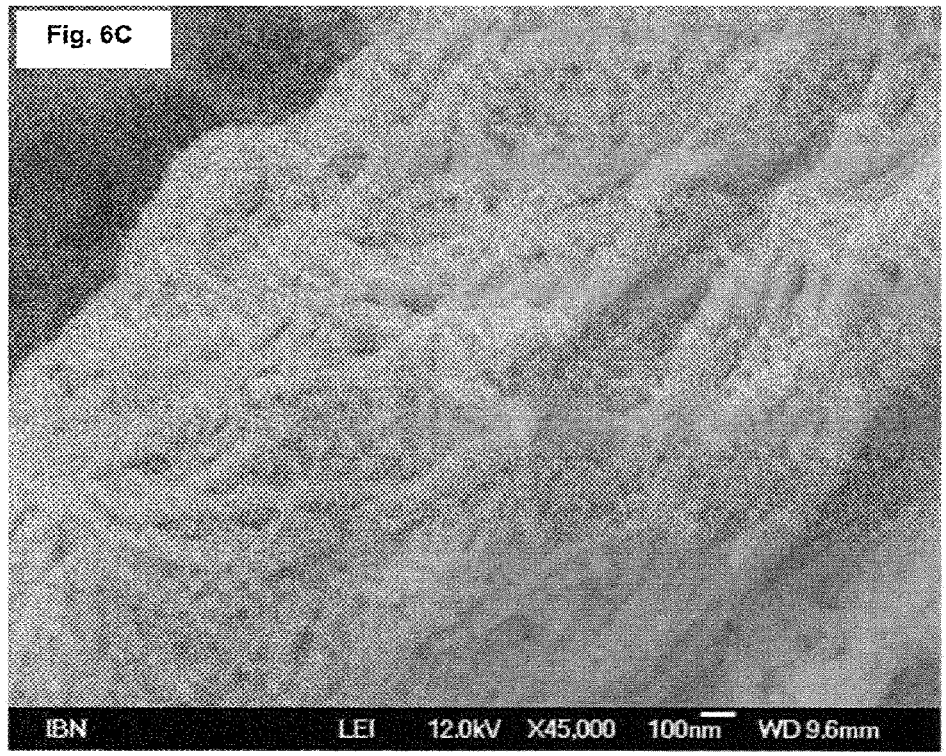

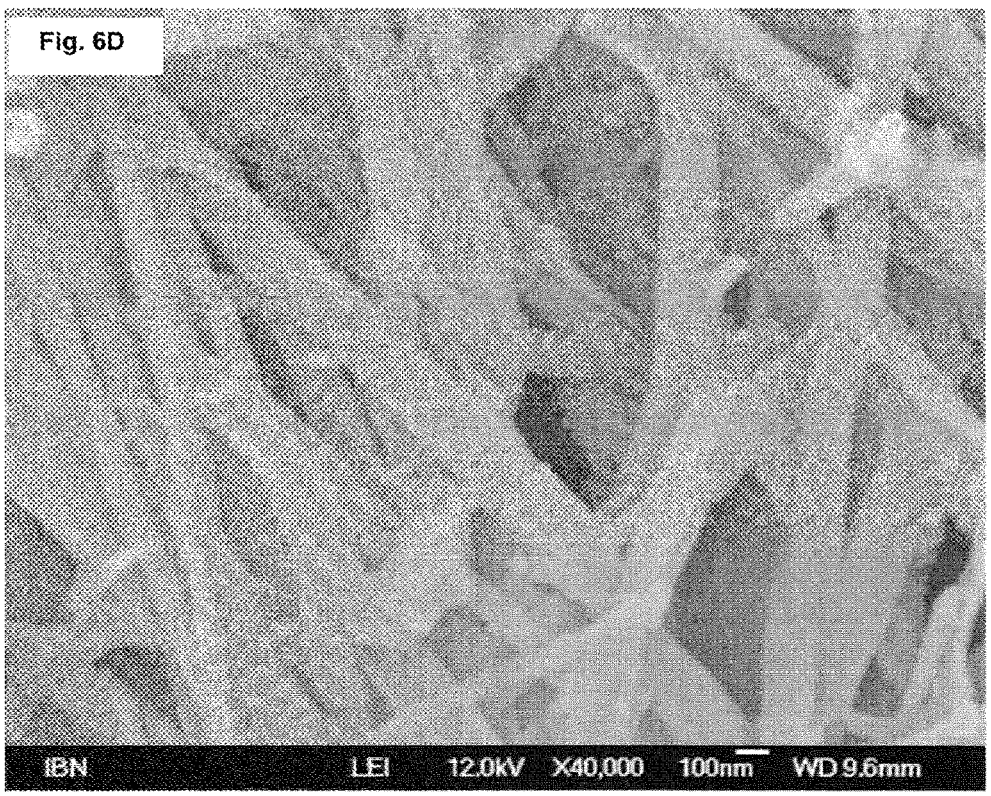

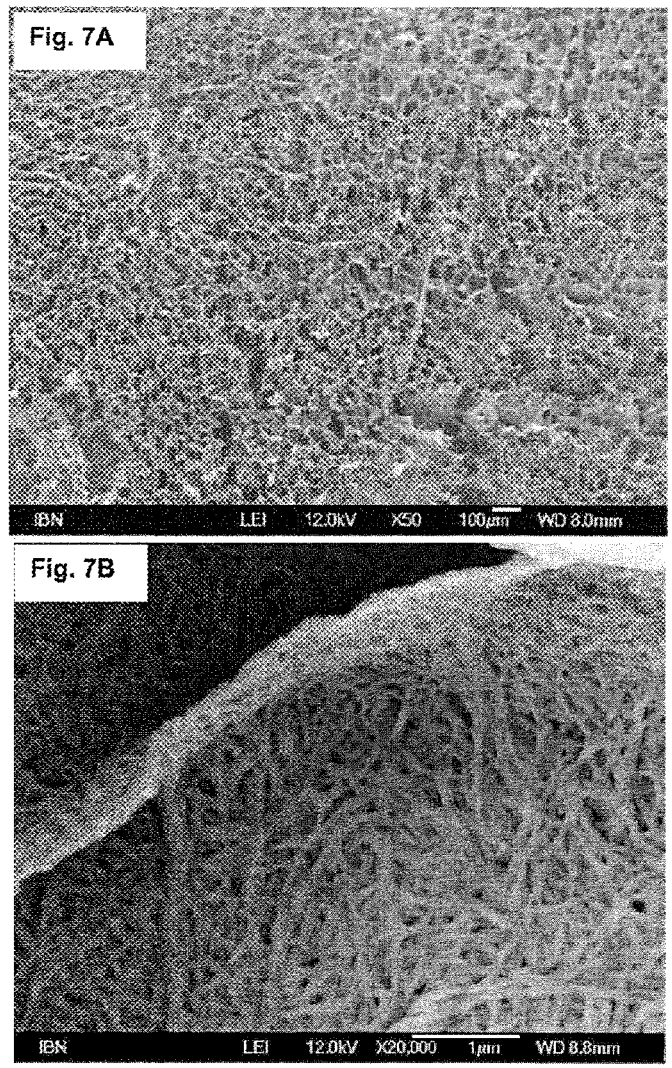

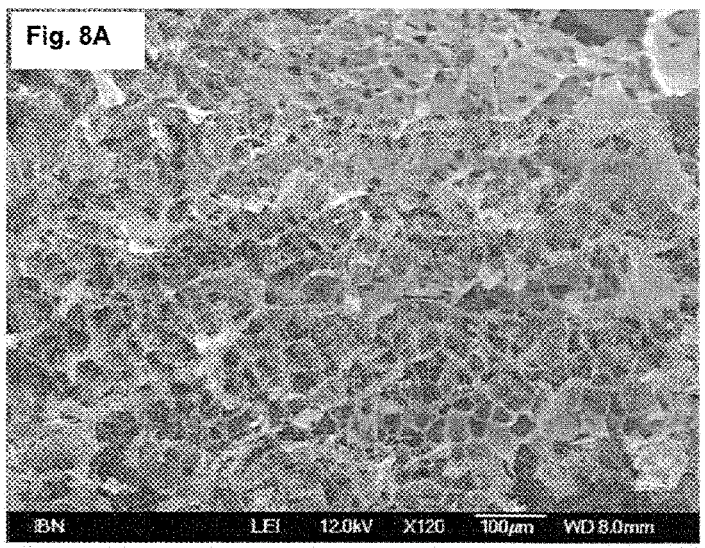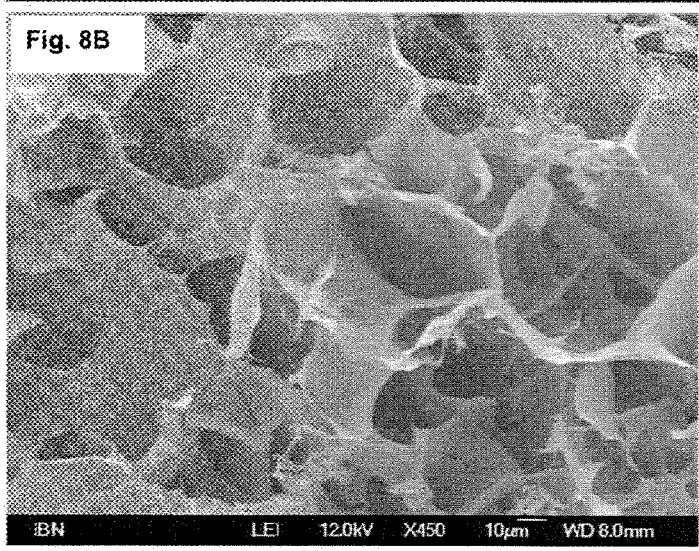

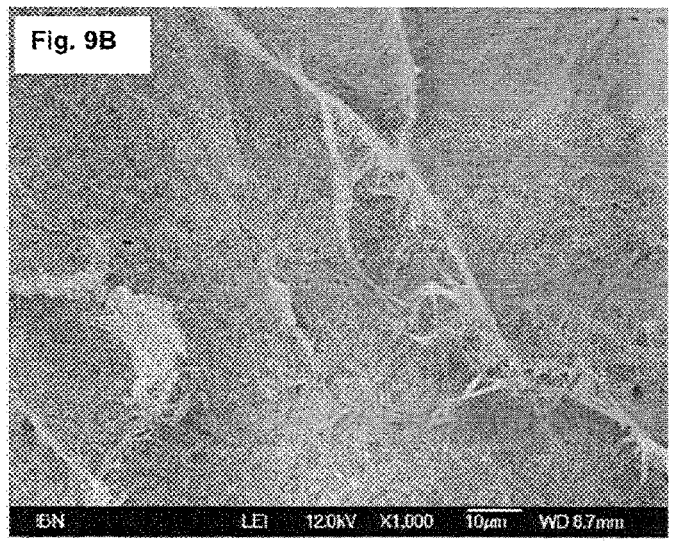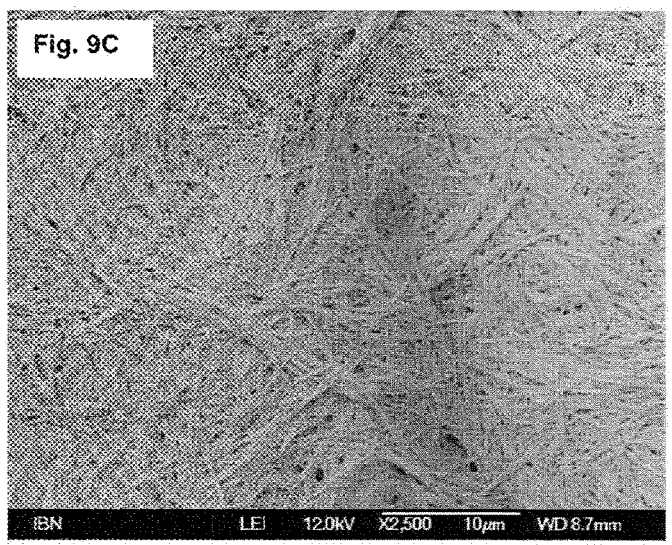

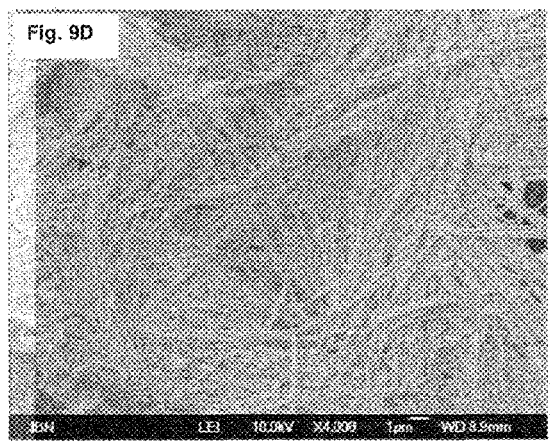 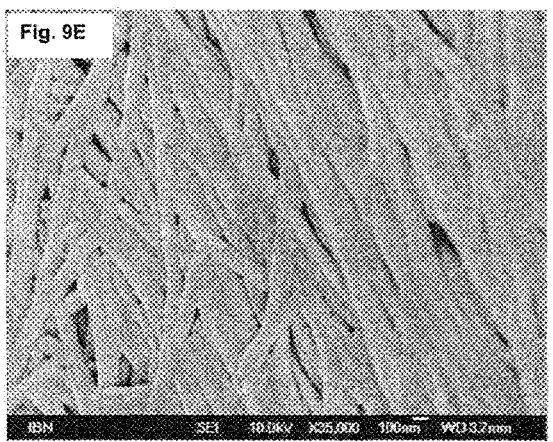

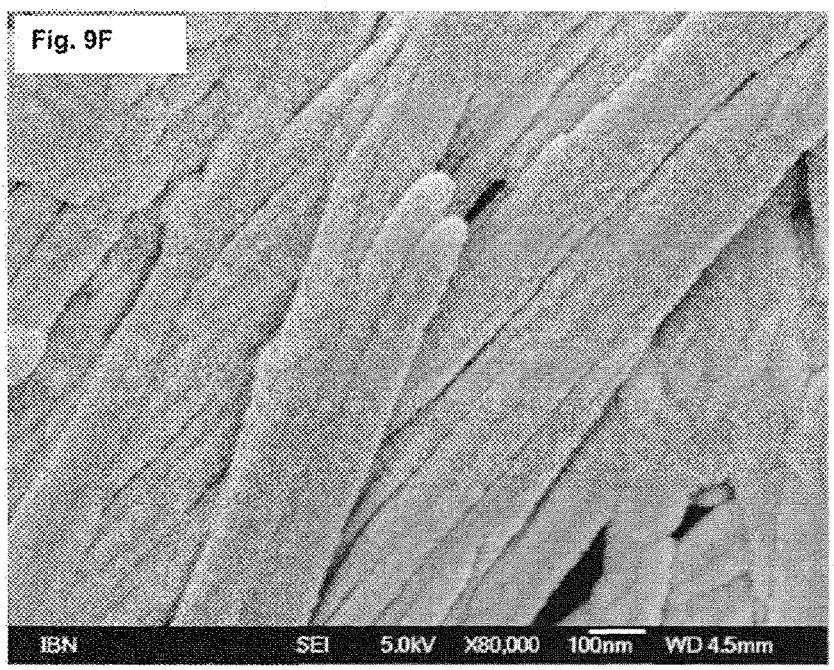

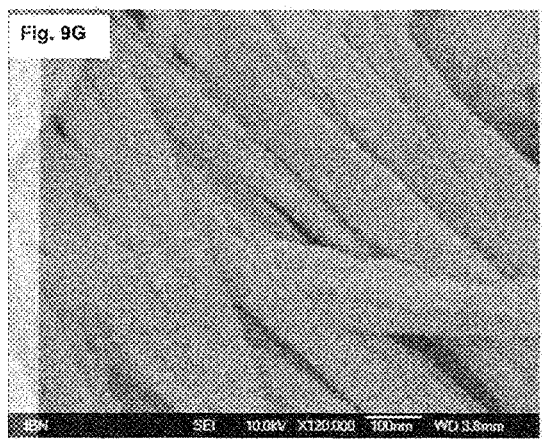 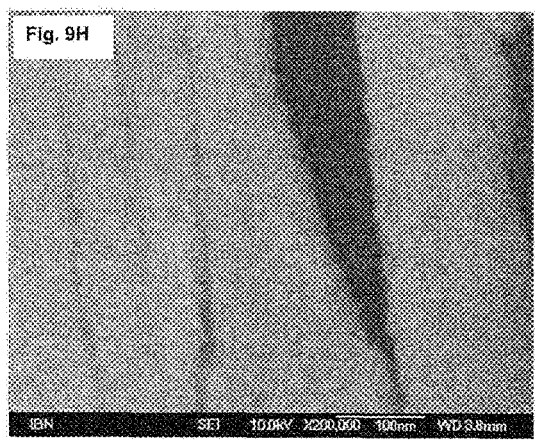

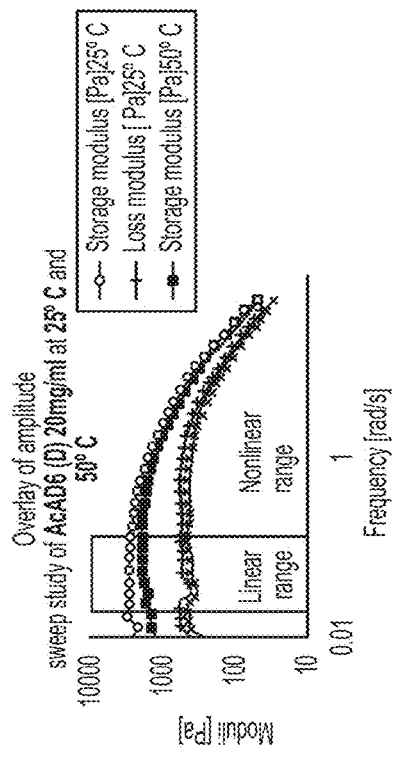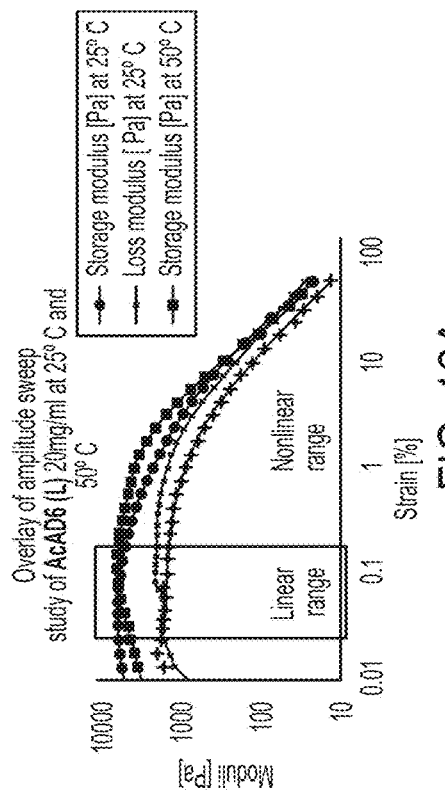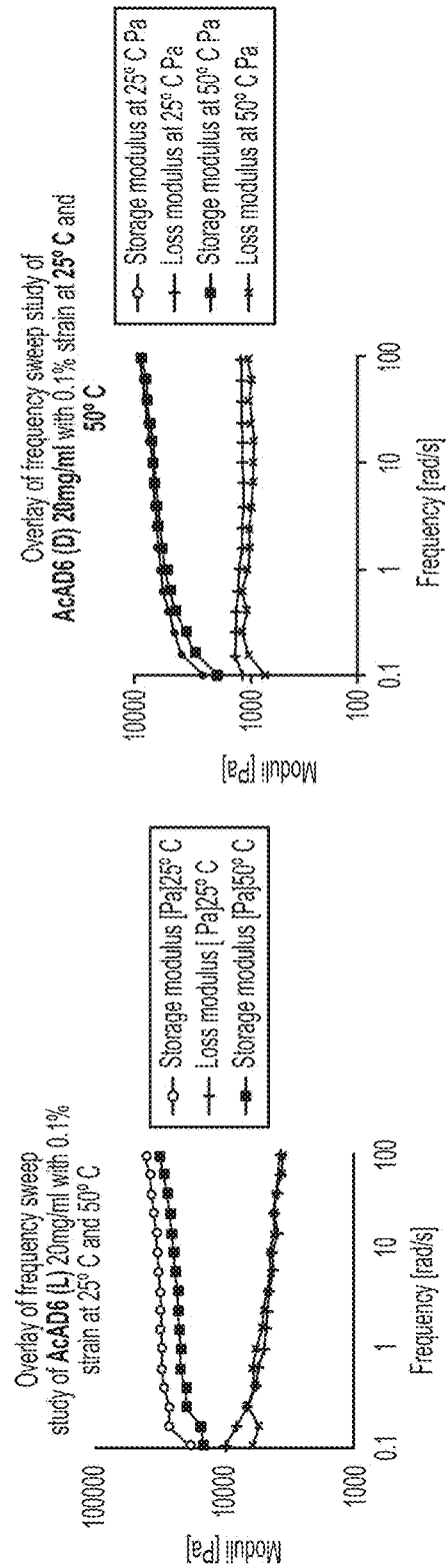
FIG. 12A
FIG. 12B
FIG. 12C
FIG. 12D

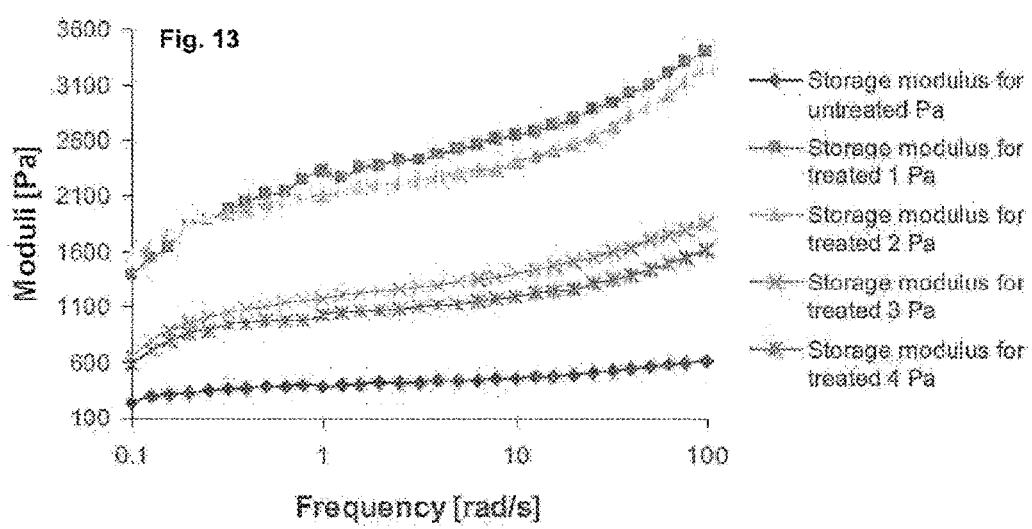

| Gelatin concentration | Frequency [rad/s] | Storage Modulus [Pa] | Loss Modulus [Pa] |
|---|---|---|---|
| 10 mg/ml | 0.1 | 17.63 | 2.77 |
| 15 mg/ml | | 36.72 | 5.48 |
| 20 mg/ml | | 54.36 | 3.95 |
| 10 mg/ml | 1 | 20.87 | 0.80 |
| 15 mg/ml | | 50.68 | 5.93 |
| 20 mg/ml | | 57.00 | 6.95 |
| 10 mg/ml | 10 | 21.90 | 0.86 |
| 15 mg/ml | | 74.35 | -15.48 |
| 20 mg/ml | | 62.63 | -7.27 |
| 10 mg/ml | 100 | 21.68 | 3.83 |
| 15 mg/ml | | 56.35 | 8.74 |
| 20 mg/ml | | 73.80 | 10.60 |

Fig. 14

LK$_6$C = Monomer-thiol = M-SH = 745.0 amu (theoretical)

CROSSLINKED PEPTIDE HYDROGELS

CROSS REFERENCE TO RELATED APPLICATIONS

This application is a divisional application of U.S. patent application Ser. No. 14/634,559, entitled "CROSSLINKED PEPTIDE HYDROGELS" and filed on Feb. 27, 2015, which is a divisional application of U.S. patent application Ser. No. 13/751,295, entitled "CROSSLINKED PEPTIDE HYDROGELS", and filed on Jan. 28, 2013, now U.S. Pat. No. 8,999,916, which is a continuation in part application of U.S. patent application Ser. No. 13/638,152, entitled "AMPHIPHILIC LINEAR PEPTIDE/PEPTOID AND HYDROGEL COMPRISING THE SAME", and filed on Sep. 28, 2012, now U.S. Pat. No. 9,067,084, which is a 35 U.S.C. § 371 National Stage of International Application No. PCT/SG2010/000469, entitled "AMPHIPHILIC LINEAR PEPTIDE/PEPTOID AND HYDROGEL COMPRISING THE SAME" and filed on Dec. 15, 2010 and claims the benefit of priority to U.S. Provisional Patent Application Ser. No. 61/319,838, filed Mar. 31, 2010, the entire contents of each of which are hereby incorporated by reference herein.

FIELD OF THE INVENTION

The present invention relates to hydrogels comprising a plurality of amphiphilic peptides and/or peptoids capable of self-assembling into three-dimensional macromolecular nanofibrous networks, which entrap water and form said hydrogels, wherein at least a portion of said plurality of amphiphilic peptides and/or peptoids is chemically crosslinked. The present invention further relates to methods for preparing such hydro gels and to various uses of such hydrogels, e.g. as cell culture substrates, for drug and gene delivery, as wound dressing, as an implant, as an injectable agent that gels in situ, in pharmaceutical or cosmetic compositions, in regenerative medicine, in tissue engineering and tissue regeneration, or in electronic devices. It also relates to a method of tissue regeneration or tissue replacement using a hydrogel in accordance with the present invention.

SEQUENCE LISTING

In accordance with 37 CFR 1.52(e)(5), the present specification makes reference to a Sequence Listing submitted electronically in the form of an ASCII text file (entitled "Sequence_Listing.txt", created on May 18, 2015 and 11 KB in size). The entire contents of the Sequence Listing are herein incorporated by reference, with the intention that, upon publication (including issuance), this incorporated sequence listing will be inserted into the published document immediately before the claims.

BACKGROUND OF THE INVENTION

Supramolecular structures are held together by intermolecular bondings that are responsible for the organization of polymolecular systems. The non-covalent, intermolecular forces which are required for the assembly of the defined supramolecular structures are mainly electrostatic interactions, hydrogen bondings, van der Waals forces, etc. Supramolecular chemistry or biology gathers a vast body of two or three dimensional complex structures and entities formed by association of chemical or biological species. These associations are governed by the principles of molecular complementarity or molecular recognition and self-assembly. The knowledge of the rules of intermolecular association can be used to design polymolecular assemblies in form of membranes, films, layers, micelles, tubules, gels for a variety of biomedical or technological applications (J.-M. Lehn, Science, 295, 2400-2403, 2002).

Peptides have been used for the fabrication of supramolecular structures through molecular self-assembly (S. Zhang, Nature Biotechnology, 21, 1171-1178, 2003). Peptides are for instance able to assemble into nanotubes (US 7, 79, 84) or into supramolecular hydrogels consisting of three dimensional scaffolds with a large amount of around 98-99% immobilized water or aqueous solution. The peptide-based biomaterials are powerful tools for potential applications in biotechnology, medicine and even technical applications. Depending on the individual properties these peptide-based hydrogels are thought to serve in the development of new materials for tissue engineering, regenerative medicine, as drug and vaccine delivery vehicles or as peptide chips for pharmaceutical research and diagnosis (E. Place et al., Nature Materials, 8, 457-470, 2009). There is also a strong interest to use peptide-based self-assembled biomaterial such as gels for the development of molecular electronic devices (A. R. Hirst et al., Angew. Chem. Int. Ed., 47, 8002-8018, 2008).

A variety of "smart peptide hydro gels" have been generated that react on external manipulations such as temperature, pH, mechanical influences or other stimuli with a dynamic behavior of swelling, shrinking or decomposing. Nevertheless, these biomaterials are still not "advanced" enough to mimic the biological variability of natural tissues as for example the extracellular matrix (ECM) or cartilage tissue or others. The challenge for a meaningful use of peptide hydrogels is to mimic the replacing natural tissues not only as "space filler" or mechanical scaffold, but to understand and cope with the biochemical signals and physiological requirements that keep the containing cells in the right place and under "in vivo" conditions (R. Fairman and K. Akerfeldt, Current Opinion in Structural Biology, 15, 453-463, 2005). Much effort has been undertaken to understand and control the relationship between peptide sequence and structure for a rational design of suitable hydrogels. In general hydrogels contain macroscopic structures such as fibers that entangle and form meshes. Most of the peptide based hydrogels utilize as their building blocks 0-pleated sheets which assemble to fibers. Later it was shown that it is possible to design hydrogelating self-assembling fibers purely from a-helices. Besides 0-sheet structure-based materials (S. Zhang et al., PNAS, 90, 3334-3338, 1993; A. Aggeli et al., Nature, 386, 259-262, 1997, etc.) a variety of a-helical hydrogels has been developed (W. A. Petka et al., Science, 281, 389-392, 1998; C. Wang et al., Nature, 397, 417-420, 1999; C. Gribbon et al., Biochemistry, 47, 10365-10371, 2008; E. Banwell et al., Nature Materials, 8, 596-600, 2009, etc.).

Nevertheless, the currently known peptide hydrogels are in most of the cases associated with low rigidity, sometimes unfavourable physiological properties and/or complexity and the requirement of substantial processing thereof which leads to high production costs. There is therefore a widely recognized need for peptide hydrogels that are easily formed, non-toxic and have a sufficiently high rigidity for standard applications. The hydrogels should also be suitable for the delivery of bioactive moieties (such as nucleic acids, small molecule therapeutics, cosmetic and anti-microbial

SUMMARY OF THE INVENTION

It is therefore desirable to provide a biocompatible compound that is capable of forming a hydrogel that meets at least some of the above requirements to a higher extent than currently available hydro gels and that is not restricted by the above mentioned limitations.

Disclosed is an amphiphilic peptide and/or peptoid capable of forming a hydrogel, the amphiphilic peptide and/or peptoid comprising an amphiphilic sequence consisting of:
a hydrophobic sequence stretch of n aliphatic amino acids, wherein n is an integer from 2 to 15, and
a hydrophilic sequence stretch linked to said hydrophobic sequence stretch and having a polar moiety which is acidic, neutral or basic, said polar moiety comprising m adjacent hydrophilic amino acids, wherein m is an integer from 1 to 5.

In one embodiment the amphiphilic peptide and/or peptoid has a C-terminus and an N-terminus wherein the N-terminus is protected by a protecting group, wherein said protecting group preferably is an acetyl group.

In one embodiment, the amphiphilic peptide and/or peptoid has a C-terminus, which, if a basic polar amino acid is located at the C-terminus, is preferably amidated.

In one embodiment, n is an integer from 2 to 6.

In one embodiment, m is an integer from 1 to 2.

In one embodiment, the amphiphilic peptide and/or peptoid consists of o amphiphilic sequences, as defined above, which amphiphilic sequences are linked to each other, o being an integer from 1 to 50.

In one embodiment, for a given amphiphilic peptide and/or peptoid, said aliphatic amino acids and said hydrophilic amino acids are either D-amino acids or L-amino acids.

In one embodiment, each of the hydrophilic amino acids has a polar group which is independently selected from a hydroxyl, an ether, a carboxyl, an imido, an amido, an ester, an amino, a guanidine, a thio, a thioether, a seleno, and a telluro group.

In one embodiment, said polar moiety of said hydrophilic sequence stretch comprises m adjacent hydrophilic amino acids, m being defined as defined above, said hydrophilic amino acids being selected from the group comprising aspartic acid, asparagine, glutamic acid, glutamine, 5-N-ethyl-glutamine (theanine), citrulline, thio-citrulline, cysteine, homocysteine, methionine, ethionine, selenomethionine, telluromethionine, threonine, allo-threonine, serine, homoserine, arginine, homoarginine, ornithine, lysine and N(6)-carboxymethyllysine, histidine, and wherein said hydrophobic sequence stretch comprises n aliphatic amino acids, n being as defined above, said aliphatic amino acids being selected from the group comprising isoleucine, norleucine, leucine, valine, alanine, glycine, homoallylglycine and homopropargylglycine. In one embodiment, m is 1 to 2.

In one embodiment, m is 2 and said polar moiety comprises two identical amino acids, or m is 1 and said polar moiety comprises any one of aspartic acid, asparagine, glutamic acid, glutamine, serine, threonine, cysteine, methionine, lysine and histidine.

In one embodiment, said polar moiety is adjacent to the hydrophobic sequence stretch of n aliphatic amino acids.

In one embodiment, said polar moiety has a sequence selected from Asp, Asn, Glu, Gin, Ser, Thr, Cys, Met, Lys, His, Asn-Asn, Asp-Asp, Glu-Glu, Gln-Gln, Asn-Gln, Gln-Asn, Asp-Gln, Gin-Asp, Asn-Glu, Glu-Asn, Asp-Glu, Glu-Asp, Gln-Glu, Glu-Gln, Asp-Asn, Asn-Asp Thr-Thr, Ser-Ser, Thr-Ser, Ser-Thr, Asp-Ser, Ser-Asp, Ser-Asn, Asn-Ser, Gln-Ser, Ser-Gln, Glu Ser, Ser-Glu, Asp-Thr, Thr-Asp, Thr-Asn, Asn-Thr, Gin-Thr, Thr-Gln, Glu-Thr, Thr-Glu.

In one embodiment, said polar moiety comprises the C-terminus of the amphiphilic peptide and/or peptoid, or wherein said polar moiety comprises the N-terminus of the amphiphilic peptide and/or peptoid.

In one embodiment, both said C-terminus and said N-terminus do not carry any protecting groups attached to them.

In one embodiment, said polar moiety comprises the C-terminus of the amphiphilic peptide and/or peptoid, wherein both said C-terminus and said N-terminus do not carry any protecting groups attached to them.

In one embodiment, said polar moiety comprises the C-terminus of the amphiphilic peptide and/or peptoid, wherein said C-terminus does not carry any protecting group, and wherein said N-terminus carries a protecting group.

In one embodiment, said protecting group is an acetyl group attached to the amino-group of said N-terminus.

In one embodiment, said polar moiety comprises the C-terminus of the amphiphilic peptide and/or peptoid, wherein said C-terminus carries a protecting group, and wherein said N-terminus does not carry any protecting group.

In one embodiment, said protecting group is an amido-group attached to the carboxyl group of said C-terminus.

In one embodiment, said polar moiety comprises the C-terminus of the amphiphilic peptide and/or peptoid, wherein both said C-terminus and N-terminus carry a protecting group.

In one embodiment, said C-terminus protecting group is an amido-group attached to the carboxyl group of said C-terminus, and wherein said N-terminus protecting group is an acetyl group attached to the amino-group of said N-terminus.

In one embodiment, said polar moiety consists of at least one amino acid positioned at the C-terminus of the amphiphilic peptide and/or peptoid.

In one embodiment, said hydrophobic sequence stretch comprises and/or forms the N-terminus of the amphiphilic peptide and/or peptoid.

In one embodiment, all or a portion of the aliphatic amino acids of the hydrophobic sequence stretch are arranged in an order of decreasing amino acid size in the direction from N- to C-terminus of the amphiphilic peptide and/or peptoid, wherein the size of the aliphatic amino acids is defined as I=L>V>A>G.

In one embodiment, said aliphatic amino acids arranged in an order of decreasing amino acid size have a sequence which is a repetitive or non-repetitive sequence.

In one embodiment, said aliphatic amino acids arranged in order of decreasing amino acid size have a sequence with a length of 2 to 7, preferably 2 to 6, more preferably 2 to 5 amino acids. In one embodiment, said aliphatic amino acids arranged in an order of decreasing amino acid size have a sequence selected from LIVAG, ILVAG, LIVAA, LAVAG, IVAG, LIVA, LIVG, IVA and IV, wherein, optionally, there is an A preceding such sequence at the N-terminus.

In one embodiment, all or a portion of the aliphatic amino acids of the hydrophobic sequence stretch are arranged in an order of identical amino acid size in the amphiphilic peptide and/or peptoid.

In one embodiment, said aliphatic amino acids arranged in order of identical amino acid size have a sequence with a length of 2 to 4 amino acids. In one embodiment, said aliphatic amino acids arranged in an order of identical size have a sequence selected from LLLL, LLL, LL, IIII, III, II, VVVV, VVV, VV, AAAA, AAA, AA, GGGG, GGG, and GG.

In one embodiment, the amphiphilic sequence undergoes a conformational change during self-assembly, preferably a conformational change from a random coil conformation to a helical intermediate structure to a final beta conformation. In one embodiment, the conformational change is concentration dependent.

In one embodiment, the amphiphilic linear sequence comprises a single hydrophilic and at least two aliphatic amino acids.

In one embodiment, the amphiphilic sequence is one of SEQ ID NO: 1-42. It should be noted that any of the amphiphilic sequences may carry a protecting group at the N-terminus or the C-terminus or both. For example, SEQ ID NO:1-42 may all carry an acetyl group as protecting group at the N-terminus. As a further example, SEQ ID NO: 19 (LIVAGK) may carry an amido-group as protecting group at the C-terminus, and additionally it may have an acetyl group at the N-terminus as protecting group.

In one embodiment, said amphiphilic peptide and/or peptoid is stable in aqueous solution at physiological conditions at ambient temperature for a period of time in the range from 1 day to at least 6 months, preferably to at least 8 months more preferably to at least 12 months.

In one embodiment, the amphiphilic peptide and/or peptoid is stable in aqueous solution at physiological conditions, at a temperature up to 90° C., for at least 1 hour.

Also disclosed is a hydrogel comprising the amphiphilic peptide and/or peptoid as defined above.

In one embodiment, the hydrogel is stable in aqueous solution at ambient temperature for a period of at least 7 days, preferably at least 2 to 4 weeks, more preferably at least 1 to 6 months.

In one embodiment, the hydrogel is characterized by a storage modulus G' to loss modulus G" ratio that is greater than 2.

In one embodiment, the hydrogel is characterized by a storage modulus G' from 100 Pa to 80, 00 Pa at a frequency in the range of from 0.02 Hz to 16 Hz.

In one embodiment, the hydrogel has a higher mechanical strength than collagen or its hydrolyzed form (gelatin).

In one embodiment, the hydrogel as defined above comprises fibers of the amphiphilic peptide and/or peptoid as defined above, said fibers defining a network that is capable of entrap-ping at least one of a microorganism, a virus particle, a peptide, a peptoid, a protein, a nucleic acid, an oligosaccharide, a polysaccharide, a vitamin, an inorganic molecule, a synthetic polymer, a small organic molecule or a pharmaceutically active compound.

In one embodiment, the hydrogel comprises at least one of a microorganism, a virus particle, a peptide, a peptoid, a protein, a nucleic acid, an oligosaccharide, a polysaccharide, a vitamin, an inorganic molecule, a synthetic polymer, a small organic molecule or a pharmaceutically active compound entrapped by the network of fibers of the amphiphilic polymer.

In one embodiment, the fibers of the amphiphilic polymer are coupled to the at least one of a microorganism, a virus particle, a peptide, a peptoid, a protein, a nucleic acid, an oligosaccharide, a polysaccharide, a vitamin, an inorganic molecule, a synthetic polymer, a small organic molecule or a pharmaceutically active compound entrapped by the network of fibers of the amphiphilic polymer.

In one embodiment, the hydrogel is comprised in at least one of a fuel cell, a solar cell, an electronic cell, a biosensing device, a medical device, an implant, a pharmaceutical composition and a cosmetic composition. In one embodiment, the hydrogel as defined above is for use in at least one of the following:
release of a pharmaceutically active compound, medical tool kit, a fuel cell, a solar cell, an electronic cell, tissue regeneration, stem cell therapy and gene therapy.

In one embodiment, the hydrogel as defined above is injectable.

Also disclosed is a method of preparing a hydrogel, the method comprising dissolving an amphiphilic peptide and/or peptoid as defined above in an aqueous solution.

In one embodiment, the dissolved amphiphilic peptide and/or peptoid in aqueous solution is further exposed to temperature, wherein the temperature is in the range from 20° C. to 90° C., preferably from 20° C. to 70° C.

In one embodiment, the amphiphilic peptide and/or peptoid is dissolved at a concentration from 0.01 µg/ml to 100 mg/ml, preferably at a concentration from 1 mg/ml to 50 mg/ml, more preferably at a concentration from about 1 mg/ml to about 20 mg/ml.

Also disclosed is a surgical implant, or stent, the surgical implant or stent comprising a peptide and/or peptoid scaffold, wherein the peptide and/or peptoid scaffold is formed by a hydrogel as defined above.

Also disclosed is a pharmaceutical and/or cosmetic composition and/or a biomedical device and/or electronic device comprising the amphiphilic peptide and/or peptoid as defined above.

In one embodiment, the pharmaceutical and/or cosmetic composition and/or the biomedical device, and/or the electronic devices as defined above, further comprises a pharmaceutically active compound.

In one embodiment, the pharmaceutical and/or cosmetic composition as defined above, further comprises a pharmaceutically acceptable carrier.

Also disclosed is a kit of parts, the kit comprising a first container with an amphiphilic peptide and/or peptoid as defined above and a second container with an aqueous solution.

In one embodiment, the aqueous solution of the second container further comprises a pharmaceutically active compound.

In one embodiment, the first container with an amphiphilic peptide and/or peptoid further comprises a pharmaceutically active compound.

Also disclosed is a method of tissue regeneration comprising the steps:
providing a hydrogel as defined above, exposing said hydrogel to cells which are to form regenerated tissue, allowing said cells to grow on said hydrogel.

In one embodiment, the method as defined above is performed in-vitro or in-vivo.

In one embodiment, the method as defined above is performed in vivo, wherein, in step a), aid hydrogel is provided at a place in a body where tissue regeneration is intended.

In one embodiment, said step a) is performed by injecting said hydrogel at a place in the body where tissue regeneration is intended.

In a first aspect the present disclosure provides an amphiphilic peptide and/or peptoid capable of forming a hydrogel. The amphiphilic peptide and/or peptoid includes a hydrophobic and a hydrophilic sequence. This hydrophobic sequence has a length of n L- or D-amino acids. n is an integer, which may typically range from 2 to about 15. The hydrophilic sequence has a polar and/or charged moiety comprising m L- or D-amino acids. m is an integer from 1 to 5. Each of the m aliphatic amino acids carries an independently selected polar group. The amphiphilic linear sequence has a net charge at physiological pH and a N-terminus carrying a protecting group. The protecting group can be an acetyl group. The amphiphilic peptide and/or peptoid may comprise o linked amphiphilic peptide and/or peptoid sequences of n hydrophobic and m hydrophilic L- and D-amino acids, wherein o is an integer from 1 to about 50. The amphiphilic peptide and/or peptoid may consist of o linked amphiphilic peptide and/or peptoid sequences of n hydrophobic and m hydrophilic L- and D-amino acids. The value of n may be an integer from 2 to about 15. The value of m may be 1 to 5. The charged and/or polar group of each of the m hydrophilic L- and D-amino acids may be independently selected from a hydroxyl, an ether, a carboxyl, an amido, an ester, an amino, a guanidino, athio, a thioether, a seleno, and a telluro group. The charged or polar moiety of the hydrophilic sequence may comprise m L- or D-amino acids selected from the group consisting of aspartic acid, asparagine, glutamic acid, glutamine, 5-N-ethyl-glutamine (theanine), citrulline, thiocitrulline, cysteine, homocysteine, methionine, ethionine, selenomethionine, telluromethionine, threonine, allo-threonine, serine, homoserine, arginine, homoarginine, ornithine, lysin and N(6)-carboxymethyllysine. The charged and/or polar moiety of the hydrophilic sequence may comprise two identical amino acids. The two identical amino acids may be adjacent to the non-polar hydrophobic moiety. The charged and/or polar moiety may consist of two amino acids with a sequence selected from Asn-Asn, Asp-Asp, Glu-Glu, Gln-Gln, Asn-Gln, Gln-Asn, Asp-Gin, Gin-Asp, Asn-Glu, Glu-Asn, Asp-Glu, Glu-Asp, Gln-Glu, Glu-Gln, Asp-Asn, Asn-Asp, Thr-Thr, Ser-Ser, Thr-Ser, Ser-Thr, Asp-Ser, Ser-Asp, Ser-Asn, Asn-Ser, Gln-Ser, Ser-Gln, Glu-Ser, Ser-Glu, Asp-Thr, Thr-Asp, Thr-Asn, Asn-Thr, Gin-Thr, Thr-Gln, Glu-Thr, Thr-Glu. The charged and/or polar moiety may comprise the C-terminus of the amphiphilic peptide and/or peptoid. The charged and/or polar moiety may comprise (i) the C-terminus, the C-terminus carrying an unprotected C-terminal carboxyl group or (ii) the N-terminus, the N-terminus carrying an unprotected N-terminal amino group. The charged and/or polar moiety may comprise the C-terminus of the amphiphilic peptide and/or peptoid, the C-terminus carrying an unprotected C-terminal carboxyl group and wherein the N-terminus carries a protecting group preferably the acetyl group. The protecting group may be an amido protecting group. The charged and/or polar moiety may consist of at least one amino acid positioned at the C-terminus of the amphiphilic peptide and/or peptoid. The hydrophobic sequence may comprise at least two aliphatic amino acids that is defined by a main chain comprising 1 to about 20 carbon atoms. A portion of the amino acids of the non-polar moiety may be arranged in a general sequence of decreasing size in the direction from N- to C-terminus of the amphiphilic peptide and/or peptoid, and the size of adjacent amino acids of the non-polar moiety may be identical or smaller in the direction of the general sequence of decreasing size. The general sequence of decreasing size may be preferably a non-repetitive sequence. The direction of the general sequence of decreasing size in which adjacent amino acids may be of identical or smaller size may be the direction toward the charged and/or polar moiety of the sequence. The portion of the amino acids arranged in a general sequence of decreasing size may have a length of 2-7, preferably 2-6, more preferably 2, 3, 4, 5 or 6 amino acids. The portion of the amino acids arranged in a general sequence of decreasing size may also have a length of n−m−1 acids and wherein the portion of the amino acids arranged in the general sequence of decreasing size may be positioned between the remaining non-polar amino acid of the non-polar moiety of n−m amino acids and the polar moiety. The remaining nonpolar amino acid of the non-polar moiety of n−m amino acids may define the N-terminus or the C-terminus of the amphiphilic peptide and/or peptoid. The remaining non-polar amino acid of the non-polar moiety of n−m amino acids may be one of alanine, valine and glycine. The amphiphilic linear sequence may undergo a conformational change from a random coil conformation to a helical conformation during self-assembly. The conformational change may be concentration dependent. The non-polar moiety of the amphiphilic linear sequence may comprise at least one L- or D-amino acid selected from the group consisting of glycine, homoallylglycine, homopropargylglycine, alanine, valine, leucine, norleucine and isoleucine. The amphiphilic linear sequence may comprise a single polar and/or charge and a single nonpolar moiety. The amphiphilic linear sequence may have a positive or a negative net charge. The net charge may be from about −1 to about −4 or from about +5 to about +1. The net charge may be from about −1 to about −2. The net charge may be −2. The net charge may be +1 or +2 or +5. The amphiphilic peptide and/or peptoid may be stable in aqueous solution at physiological conditions at ambient temperature for a period of time in the range from 1 day to at least 6 months, preferably at least 8 months, more preferably at least 12 months. The amphiphilic peptide and/or peptoid may be stable in aqueous solution at physiological conditions at a temperature to 90° C. for at least 1 hour.

In a second aspect the disclosure provides a hydrogel. The hydrogel includes an amphiphilic peptide and/or peptoid according to the first aspect. The hydrogel may be stable in aqueous solution at ambient temperature for a period of at least 7 days. The hydrogel may be stable in aqueous solution at ambient temperature for a period of at least 2 to 4 weeks. The hydrogel may be stable in aqueous solution at ambient temperature for a period of at least 1 to 6 months. The hydrogel mechanical property may be characterized by a loss modulus G" to storage modulus G' ratio that is less than 1. The hydrogel may be characterized by magnitude of storage modulus G' greater than loss modulus G" by minimum factor of 1.5. The hydrogel may be characterized by a storage modulus G' of from 100 Pa to 80, 00 Pa at a frequency in the range of from 0.02 Hz to 16 Hz. The hydrogel may be characterized by higher storage modulus G' with increase in the concentration of peptide. The hydrogel may have a higher mechanical strength than collagen or hydrolyzed form (gelatin). The hydrogel may comprise fibers of an amphiphilic peptide and/or peptoid described herein. The fibers may define a network that is capable of entrapping at least one of a microorganism, a virus particle, a peptide, a peptoid, a protein, a nucleic acid, an oligosaccharide, a polysaccharide, a vitamin, an inorganic molecule, a synthetic polymer, a small organic molecule or a pharmaceutically active compound. The hydrogel may comprise at least one of a microorganism, a virus particle, a peptide, a peptoid, a protein, a nucleic acid, an oligosaccharide, a polysaccharide, a vitamin, an inorganic molecule, a synthetic polymer, a small organic molecule or a pharmaceutically active compound entrapped by the network of fibers of the amphiphilic polymer. The fibers of the amphiphilic polymer may be coupled to the at least one of a microorganism, a virus particle, a peptide, a peptoid, a protein, a nucleic acid, an oligosaccharide, a polysaccharide, a vitamin, an inorganic molecule, a synthetic polymer, a small organic molecule or a pharmaceutically active compound entrapped by the network of fibers of the amphiphilic polymer. The hydrogel may be comprised in at least one of a fuel cell, a solar cell, a electronic cell, a biosensing device, a medical device, an implant, a pharmaceutical composition, drug delivery system, tissue culture medium, biosensor devices and a cosmetic composition. The hydrogel may be for at least one of release of a pharmaceutically active compound, medical tool kit, a fuel cell, a solar cell, an electronic cell, tissue regeneration, stem cell therapy and gene therapy. In some embodiments the hydrogel may be used for tissue regeneration, drug release or gene therapy.

In a third aspect the disclosure provides a method of preparing a hydrogel. The method includes providing an amphiphilic peptide and/or peptoid according to the first aspect. The method further includes dissolving and/or dispersing the amphiphilic peptide and/or peptoid in an aqueous solution. The dissolved/dispersed amphiphilic peptide and/or peptoid in aqueous solution may be further exposed to a temperature. The temperature may be selected in the range from about 20° C. to about 90, preferably from 20° C. to 70° C. The amphiphilic peptide and/or peptoid may be dissolved at a concentration from about 0.01 µg/ml to about 100 mg/ml. The amphiphilic peptide and/or peptoid may be dissolved at a concentration from about 1 mg/ml to about 50 mg/ml. The amphiphilic peptide and/or peptoid may be dissolved and/or dispersed at a concentration from about 1 mg/ml to about 30 mg/ml.

In a fourth aspect the disclosure provides a surgical implant or stent. The surgical implant or stent includes a peptide and/or peptoid scaffold. The peptide and/or peptoid scaffold is defined by a hydrogel according to the second aspect.

In a fifth aspect the disclosure provides a pharmaceutical and/or cosmetic composition. The pharmaceutical and/or cosmetic composition includes the amphiphilic peptide and/or peptoid according to the first aspect. The pharmaceutical and/or cosmetic composition may comprise a pharmaceutically active compound. The pharmaceutical and/or cosmetic composition may comprise a pharmaceutically acceptable carrier.

In a sixth aspect the disclosure provides a kit of parts. The kit includes a first container and a second container. The first container includes a peptide and/or peptoid according to the first aspect. The second container includes an aqueous solution. The aqueous solution of the second container may further comprise a pharmaceutically active compound. The first container with an amphiphilic peptide and/or peptoid may further comprise a pharmaceutically active compound.

It was an object of the present invention to further improve the above disclosed hydrogels in terms of their material properties, such as stiffness, elasticity and resistance to degradation. It was a further object of the present invention to facilitate the conjugation of bioactive agents or other compounds of interest (e.g. nanoparticles) to the hydrogel. Yet another object was to reduce the amount of amphiphilic peptides and/or peptoids required for preparing hydrogels as disclosed above.

The objects of the present invention are solved by a hydrogel comprising a plurality of amphiphilic peptides and/or peptoids capable of self-assembling into three-dimensional macromolecular nanofibrous networks, which entrap water and form said hydrogel, the amphiphilic peptides and/or peptoids having the general formula:

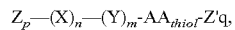

$Z_p-(X)_n-(Y)_m-AA_{thiol}-Z'_q,$ wherein
Z is an N-terminal protecting group, X is, at each occurrence, independently selected from an aliphatic amino acid, Y is, at each occurrence, independently selected from a hydrophilic amino acid, $AA_{thiol}$ is an amino acid comprising a thiol group, Z' is a C-terminal protecting group, n is an integer selected from 2 to 6, preferably 2 to 5, m is selected from 0, 1 and 2, preferably 0 and 1, and p and q are independently selected from 0 and 1, wherein, preferably, p is 1, wherein at least a portion of said plurality of amphiphilic peptides and/or peptoids is chemically (e.g. covalently) cross-linked.

In one embodiment, said amino acid comprising a thiol group is selected from cysteine and homocysteine.

In one embodiment, said at least a portion of said plurality of amphiphilic peptides and/or peptoids is chemically cross-linked via sulfhydryl-to-sulfhydryl cross-linking (i.e. via disulfide bridges), via sulfhydryl-to-hydroxyl cross-linking, via sulfhydryl-to-aldehyde cross-linking, via sulfhydryl-to-amine cross-linking, via peptidoglycans or via photo-induced cross-linking, preferably via sulfhydryl-to-sulfhydryl cross-linking. In one embodiment, said N-terminal protecting group has the general formula —C(O)—R, wherein R is selected from the group consisting of H, unsubstituted or substituted alkyls, and unsubstituted or substituted aryls. Preferred alkyls are methyl, ethyl, butyl, isobutyl, propyl and isopropyl.

In one embodiment, said N-terminal protecting group is an acetyl group (R=methyl).

In one embodiment, said N-terminal protecting group is a peptidomimetic molecule, including natural and synthetic amino acid derivatives, wherein the N-terminus of said peptidomimetic molecule may be modified with a functional group selected from the group consisting of carboxylic acid, amide, alcohol, aldehyde, amine, imine, nitrile, an urea analog, thiol, phosphate, carbonate, sulfate, nitrate, maleimide, vinyl sulfone, azide, alkyne, alkene, carbohydrate, imide, peroxide, ester, thioester; aryl, ketone, sulphite, nitrite, phosphonate and silane.

In one embodiment, said C-terminal protecting group is an amide group.

In one embodiment, the C-terminus of said amphiphilic peptides and/or peptoids has the formula —CONHR or —CONRR', with R and R' being selected from the group consisting of H, unsubstituted or substituted alkyls, and unsubstituted or substituted aryls. Preferred alkyls are methyl, ethyl, butyl, isobutyl, propyl and isopropyl.

In one embodiment, said C-terminal protecting group is an ester group.

In one embodiment, the C-terminus of said amphiphilic peptide and/or peptoid has the formula —$CO_2R$, with R being selected from the group consisting of H, unsubstituted or substituted alkyls, and unsubstituted or substituted aryls. Preferred alkyls are methyl, ethyl, butyl, isobutyl, propyl and isopropyl.

In one embodiment, said C-terminal protecting group is a peptidomimetic molecule, including natural and synthetic amino acid derivatives, wherein the C-terminus of said peptidomimetic molecule may be modified with a functional group selected from the group consisting of carboxylic acid, amide, alcohol, aldehyde, amine, imine, nitrile, an urea analog, thiol, phosphate, carbonate, sulfate, nitrate, maleimide, vinyl sulfone, azide, alkyne, alkene, carbohydrate, imide, peroxide, ester, thioester, aryl, ketone, sulphite, nitrite, phosphonate and silane.

In one embodiment, for a given amphiphilic peptide and/or peptoid, said aliphatic amino acid, said hydrophilic amino acid and said amino acid comprising a thiol group are either D-amino acids or L-amino acids.

In one embodiment, said hydrophilic amino acid has a polar group which is independently selected from a hydroxyl, an ether, a carboxyl, an imido, an amido, an ester, an amino, a guanidino, a thio, a thioether, a seleno, and a telluro group.

In one embodiment, said hydrophilic amino acid is selected from the group consisting of aspartic acid, asparagine, glutamic acid, glutamine, 5-N-ethyl-glutamine (theanine), citrulline, thio-citrulline, cysteine, homocysteine, methionine, ethionine, selenomethionine, telluromethionine, threonine, allo-threonine, serine, homoserine, arginine, homoarginine, ornithine (Orn), 2,-diaminobutyric acid (Dab), 2,-diaminopropionic acid (Dap), lysine and N(6) carboxymethyllysine and histidine.

In one embodiment, said hydrophilic amino acid is selected from the group consisting of aspartic acid, asparagine, glutamic acid, glutamine, serine, threonine, cysteine, methionine, lysine, ornithine (Orn), 2,-diaminobutyric acid (Dab), 2,-diaminopropionic acid (Dap) and histidine.

In one embodiment, said aliphatic amino acid is selected from the group consisting of isoleucine, norleucine, leucine, valine, alanine, glycine, homoallylglycine and homopropargylglycine. Preferably, said aliphatic amino acid is selected from the group consisting of isoleucine, leucine, valine, alanine and glycine.

In one embodiment, all or a portion of the aliphatic amino acids of the amphiphilic peptides and/or peptoids, i.e. (X)n, are arranged in an order of decreasing amino acid size in the direction from N- to C-terminus of the amphiphilic peptides and/or peptoids, wherein the size of the aliphatic amino acids is defined as I=L>V>A>G.

In one embodiment, said aliphatic amino acids arranged in an order of decreasing amino acid size have a sequence which is a repetitive or non-repetitive sequence. In one embodiment, said aliphatic amino acids arranged in an order of decreasing amino acid size have a sequence selected from LIVAG, ILVAG, LIVAA, LAVAG, LAVAG, LIVA, LIVG, IVA and IV, wherein, optionally, there is an A preceding such sequence at the N-terminus.

In one embodiment, said amphiphilic peptides and/or peptoids undergo a conformational change during self-assembly, preferably a conformational change from a random coil conformation to a helical intermediate structure to a final beta conformation.

In one embodiment, the conformational change is dependent on the concentration of the amphiphilic peptides and/or peptoids, dependent on the ionic environment, pH dependent and/or temperature dependent. In one embodiment, said amphiphilic peptides and/or peptoids are the same or different. In one embodiment, $(X)_n\text{-}(Y)_m$ is selected from the group consisting of SEQ ID NO: 1 to 42. In one embodiment, $(X)_n\text{-}(Y)_m\text{-}AA_{thiol}$ is selected from the group consisting of LIVAGKC (SEQ ID NO:43), LIVAGSC (SEQ ID NO: 44), LIVAGDC (SEQ ID NO: 45), ILVAGKC (SEQ ID NO: 46), ILVAGDC (SEQ ID NO: 47), LIVAGC (SEQ ID NO: 48), AIVAGC (SEQ ID NO: 49), ILVAGC (SEQ ID NO: 50), IVKC (SEQ ID NO: 51), IVDC (SEQ ID NO: 52) and IVSC (SEQ ID NO: 53).

In one embodiment, the hydrogel is stable in aqueous solution at ambient temperature for a period of at least 7 days, preferably at least 2 to 4 weeks, more preferably at least 1 to 6 months.

In one embodiment, at least 5%, preferably at least 10%, more preferably at least 15%, more preferably at least 20%, more preferably at least 25%, more preferably at least 30%, more preferably at least 35%, more preferably at least 40%, more preferably at least 45%, even more preferably at least 50% of said plurality of amphiphilic peptides and/or peptoids are chemically cross-linked.

In one embodiment, at least 60% of said plurality of amphiphilic peptides and/or peptoids are chemically cross-linked. In one embodiment, the hydrogel is characterized by a storage modulus G' to loss modulus G" ratio that is greater than 2.

In one embodiment, the hydrogel is characterized by a storage modulus G' from 100 Pa to 400, 00 Pa, preferably 500 Pa to 400, 00 Pa, even more preferably 1000 Pa to 400, 00 Pa, at a frequency in the range of from 0.02 Hz to 16 Hz.

In one embodiment, the hydrogel has a higher mechanical strength than collagen or its hydrolyzed form (gelatine).

In one embodiment, the hydrogel has an elasticity defined as % strain at linear viscoelasticity (LVE) limit above 0.01% strain, preferably above 0.5% strain, more preferably above 1% strain, more preferably above 2% strain.

In one embodiment, the hydrogel further comprises a non-peptidic polymer.

In one embodiment, the hydrogel further comprises at least one of a microorganism, a cell, a virus particle, a peptide, a peptoid, a protein, a nucleic acid, an oligosaccharide, a polysaccharide, a vitamin, an inorganic molecule, a nano- or microparticle, a synthetic polymer, a small organic molecule, a cosmetic agent or a pharmaceutically active compound.

In one embodiment, said at least one of a microorganism, a cell, a virus particle, a peptide, a peptoid, a protein, a nucleic acid, an oligosaccharide, a polysaccharide, a vitamin, an inorganic molecule, a nano- or microparticle, a synthetic polymer, a small organic molecule, a cosmetic agent or a pharmaceutically active compound is entrapped by said three-dimensional macromolecular nanofibrous networks.

In one embodiment, said at least one of a microorganism, a cell, a virus particle, a peptide, a peptoid, a protein, a nucleic acid, an oligosaccharide, a polysaccharide, a vitamin, an inorganic molecule, a nano- or microparticle, a synthetic polymer, a small organic molecule, a cosmetic agent or a pharmaceutically active compound is coupled to said amphiphilic peptides and/or peptoids, preferably via a disulfide bridge.

In one embodiment, said at least one of a microorganism, a cell, a virus particle, a peptide, a peptoid, a protein, a nucleic acid, an oligosaccharide, a polysaccharide, a vitamin, an inorganic molecule, a nano- or microparticle, a synthetic polymer, a small organic molecule, a cosmetic agent or a pharmaceutically active compound is coupled to said non-peptidic polymer. In one embodiment, said pharmaceutically active compound is selected from the group consisting of haemostatic agents, antibiotics, anti-microbial agents, anti-fungal agents, anti-inflammatory agents, analgesics, anti-coagulants, antibodies, antigens, growth factors and cytokines. In one embodiment, said nano- or microparticle is a metal nano- or microparticle, preferably a gold nano- or microparticle.

In one embodiment, said peptide comprises a signal sequence, wherein, preferably, said peptide is coupled to said amphiphilic peptides and/or peptoids via a disulfide bridge.

In one embodiment, said signal sequence comprises an adhesion or growth signal, such as an integrin binding sequence (e.g. CRGD).

In one embodiment, said hydrogel is provided in an injectable form and gels in situ. The objects of the present invention are also solved by a method of preparing a hydrogel, preferably a hydrogel according to the present invention, the method comprising the step of dissolving amphiphilic peptides and/or peptoids, as defined above in connection with the hydrogel according to the present invention, in an aqueous solution, wherein said aqueous solution comprises an oxidizing agent or wherein said method further comprises the step of exposing the ready-made hydrogel to a solution of an oxidizing agent.

In one embodiment, said oxidizing agent is $H_2O_2$, wherein, preferably, $H_2O_2$ is used at a concentration from 0.02 to 0.1% (w/w), preferably 0.04 to 0.08% (w/w), more preferably 0.05 to 0.07% (w/w).

In one embodiment, said amphiphilic peptides and/or peptoids are dissolved at a concentration from 0.01 µg/ml to 50 mg/ml, preferably at a concentration from 1 mg/ml to 25 mg/ml, more preferably at a concentration from 1 mg/ml to 15 mg/ml, even more preferably at a concentration from 5 mg/ml to 12 mg/ml.

In one embodiment, the dissolved amphiphilic peptides and/or peptoids in aqueous solution are further exposed to a temperature in the range of from 20° C. to 90° C., preferably 20° C. to 70 C, more preferably 20° C. to 40° C.

In one embodiment, the dissolved amphiphilic peptides and/or peptoids in aqueous solution are exposed to said temperature for at least 1 hour, preferably at least 2 hours, more preferably at least 4 hours, more preferably at least 6 hours, more preferably at least 8 hours, more preferably at least 10 hours, more preferably at least 12 hours, even more preferably at least 24 hours.

In one embodiment, the method further comprises the step of exposing the ready-made hydrogel to an aqueous solution not comprising said oxidizing agent, wherein, if said method comprises the step of exposing the ready-made hydrogel to a solution of said oxidizing agent, said step of exposing the ready-made hydrogel to an aqueous solution not comprising said oxidizing agent is performed after said step of exposing the ready-made hydrogel to a solution of said oxidizing agent.

In one embodiment, said step of exposing the ready-made hydrogel to an aqueous solution not comprising said oxidizing agent is repeated at least once.

In one embodiment, said step of exposing the ready-made hydrogel to an aqueous solution not comprising said oxidizing agent occurs for at least 1 hour, preferably at least 2 hours, more preferably at least 4 hours, even more preferably at least 6 hours.

In one embodiment, said step of exposing the ready-made hydrogel to an aqueous solution not comprising said oxidizing agent occurs at a temperature in the range of from 30° C. to 45° C., preferably 35° C. to 40° C.

The step of exposing the ready-made hydrogel to an aqueous solution not comprising said oxidizing agent is used to remove unreacted oxidizing agent and/or residual acid from solid-phase peptide synthesis. In one embodiment, more than 90%, preferably more than 95%, more preferably more than 97%, even more preferably more than 99% of the unreacted oxidizing agent (e.g. $H_2O_2$) are removed.

In one embodiment, said aqueous solution not comprising said oxidizing agent is water or a buffered aqueous solution (e.g. PBS).

In one embodiment, said aqueous solution not comprising said oxidizing agent is a cell culture medium. In one embodiment, the method further comprises at least one of the steps of:
 adding at least one of a microorganism, a cell, a virus particle, a peptide, a peptoid, a protein, a nucleic acid, an oligosaccharide, a polysaccharide, a vitamin, an inorganic molecule, a nano- or microparticle, a synthetic polymer, a small organic molecule, a cosmetic agent or a pharmaceutically active compound;
 adding at least one non-peptidic polymer;
 adding at least one gelation enhancer; —adding at least one buffer, preferably at least one physiologically acceptable buffer.

In one embodiment, said gelation enhancer is a salt or a solution of a salt. The objects of the present invention are also solved by a hydrogel prepared by the method according to the present invention.

The objects of the present invention are also solved by the use of a hydrogel according to the present invention as a cell culture substrate, preferably a cell culture substrate for 3-D cell culture.

The objects of the present invention are also solved by the use of a hydrogel according to the present invention as a device for drug or gene delivery, preferably for sustained or controlled release drug delivery, or as a wound dressing or as an implant or as an injectable agent that gels in situ.

The objects of the present invention are also solved by a cell culture substrate, preferably a cell culture substrate for 3-D cell culture, comprising a hydrogel according to the present invention.

The objects of the present invention are also solved by a device for drug or gene delivery, preferably sustained or controlled release drug delivery, comprising a hydrogel according to the present invention.

The objects of the present invention are also solved by an implant or injectable agent or wound dressing comprising a hydrogel according to the present invention.

The objects of the present invention are also solved by a pharmaceutical or cosmetic composition comprising a hydrogel according to the present invention.

In one embodiment, the pharmaceutical or cosmetic composition is provided in the form of a topical gel or cream, a spray, a powder, or a sheet, patch or membrane.

In one embodiment, the pharmaceutical or cosmetic composition is provided in the form of an injectable solution. In one embodiment, the pharmaceutical or cosmetic composition further comprises a pharmaceutically active compound.

In one embodiment, the pharmaceutical or cosmetic composition further comprises a pharmaceutically acceptable carrier.

The objects of the present invention are also solved by a hydrogel according to the present invention for use in regenerative medicine or for use in tissue engineering and tissue regeneration, e.g. regeneration of adipose and cartilage tissue.

The objects of the present invention are also solved by a hydrogel according to the present invention for use in the treatment of wounds.

The objects of the present invention are also solved by a hydrogel according to the present invention for use in the treatment of degenerative diseases of the skeletal system, e.g. degenerative disc disease, or urinary incontinence.

The objects of the present invention are also solved by a hydrogel according to the present invention for cosmetic use.

The objects of the present invention are also solved by an electronic device comprising a hydrogel according to the present invention.

In one embodiment, the electronic device is selected from a fuel cell, a solar cell, an electronic cell or a biosensing device.

The objects of the present invention are also solved by a method of tissue regeneration or tissue replacement comprising the steps:
 a) providing a hydrogel according to the present invention;
 b) exposing said hydrogel to cells which are to form regenerated tissue;
 c) allowing said cells to grow on or in said hydrogel.

In one embodiment, the method is performed in vitro or in vivo or ex vivo.

In one embodiment, the method is performed in vivo, wherein, in step a), said hydrogel is provided at a place in the body of a patient where tissue regeneration or tissue replacement is intended. In one embodiment, said tissue is selected from the group comprising skin tissue, nucleus pulposus in the intervertebral disc, cartilage tissue, synovial fluid and submucosal connective tissue in the bladder neck. In one embodiment, said step a) is performed by injecting said hydrogel or a solution of amphiphilic peptides and/or peptoids as defined above in connection with the hydrogel according to the present invention at a place in the body of a patient where tissue regeneration or tissue replacement is intended. In one embodiment, said step a) further comprises the co-injection of a gelation enhancer, preferably of a solution of a salt, and/or the co-injection of an oxidizing agent.

In one embodiment, the method is performed ex vivo, wherein, in step a) or b), cells from a patient or from a donor are mixed with said hydrogel, and the resulting mixture is provided at a place in the body of a patient where tissue regeneration or tissue replacement is intended.

In one embodiment, said hydrogel comprises one or more bioactive therapeutics that stimulate regenerative processes and/or modulate the immune response.

Other aspects and features of the present invention will become apparent to those skilled in the art upon review of the following description of specific embodiments of the invention in conjunction with the accompanying FIGS. 1K-M and 17 to 40.

BRIEF DESCRIPTION OF THE DRAWINGS

Reference is now made to the figures, wherein:

FIGS. 1A to 1M represent a sorted list of some exemplary peptides capable of forming hydrogels. These peptides are embodiments in which the entire peptide consists of a single linear amphiphilic sequence. Peptides which are forming hydrogels are named with a short code, but their individual sequence is disclosed. The peptides of these examples consist of a sequence of natural amino acids containing 3 to 7 amino acids. The N-terminus is acetylated which removes the charge that would otherwise restrain the amphiphilic character of the peptides.

FIG. 5A, FIG. 5B and FIG. 5C are images obtained at magnification of 260×, 1000×, 2000×, 2400×, 4000× at a temperature of 4° C. with HV at 10 KV. The images indicate the formation of fibrous structures.

FIGS. 6A-D show field emission scanning electron microscopy (FESEM) images of hydrogels of Ac-LD6 (Ac-LIVAGD) (L) (15 mg/ml), where FIGS. 6A-D are images obtained at magnifications of 6000×, 45000×, 45000× and 40000× with HV at 10 KV.

FIGS. 7A-B depict field emission scanning electron microscopy (FESEM) images of Ac-AD6 (Ac-AIVAGD) (D) hydrogels (20 mg/ml) at a magnification of 50× (FIG. 7A) and 20000× (FIG. 7B) at 12 KV.

FIGS. 8A-B show field emission scanning electron microscopy (FESEM) images of hydrogels of Ac-AD6 (Ac-AIVAGD) (D) (20 mg/ml) obtained at 120× (FIG. 8A), and 450× (FIG. 8B).

FIG. 9B shows an image obtained at a magnification of 1000×, HV of 12 KV, FIG. 9C obtained at a magnification of 2500×, HV of 12 KV, FIG. 9D obtained at a magnification of 4000×, HV of 10 KV, FIG. 9E obtained at a magnification of 35000×, HV of 10 KV, FIG. 9F at a magnification of 80000×, HV of 5 KV, FIG. 9G obtained at a magnification of 120000×, HV of 10 KV, and FIG. 9H at a magnification of 200000×, HV of 10 KV.

FIGS. 12A-D show further examples of a rheology measurements for peptide based hydrogels. FIG. 12A and FIG. 12B depict oscillatory amplitude sweep studies at temperatures of 25° C. and 50° C. for Ac-AD6 (Ac-AIVAGD) (L) and Ac-AD6 (D) at a concentration of 20 mg/ml with a constant frequency of [1rad-s] and a gap of 0.8 mm. The graphs indicate the plot of moduli [Pa] versus strain (%) at temperatures of 25° C. and 50° C. The linear viscoelastic range was observed at 0.07% to 0.2 strain % at temperatures of 25° C. and 50° C. FIG. 12C and FIG. 12D depict oscillatory frequency sweep Studies at temperatures of 25° C. and 50° C. for Ac-AD6(L) and Ac-AD6(D) at a concentration of 20 mg/ml with varying frequency ranges from 0.1 to 100 [Rad/s] with a constant strain [%] of 0.1% linear viscoelastic range and a gap of 0.8 mm.

FIG. 13 shows a further example of a rheology measurement for peptide based hydrogels. Depicted is a frequency sweep study of a UV cross-linked peptide at a temperature of 25° C. with 0.1% strain.

FIG. 14 depicts rheology measurements for gelatin-1890 (type A, porcine skin). This figure shows moduli data obtained at 25° C. when applying different frequencies.

FIG. 15A shows a microscopy image of human primary renal tubule cells (HPRTC) after 72 hours after seeding on a hydrogel of Ac-LD$_6$ (Ac-LIVAGD) (L) in DMEM medium, grown at optimum conditions. FIG. 15B shows microscopy images of human primary renal tubule cells (HPRTC) after 72 hrs after seeding on tissue culture plastic, grown at optimum conditions. FIG. 15C shows microscopy images of human umbilical vein endothelial cells (HUVEC) after 72 hrs after seeding on gels of Ac-LD$_6$ (L) in DMEM medium, grown at optimum conditions. FIG. 15D shows microscopy images of human umbilical vein endothelial cells (HUVEC) after 72 hrs after seeding on tissue culture plastic, grown at optimum conditions.

Figure 2:
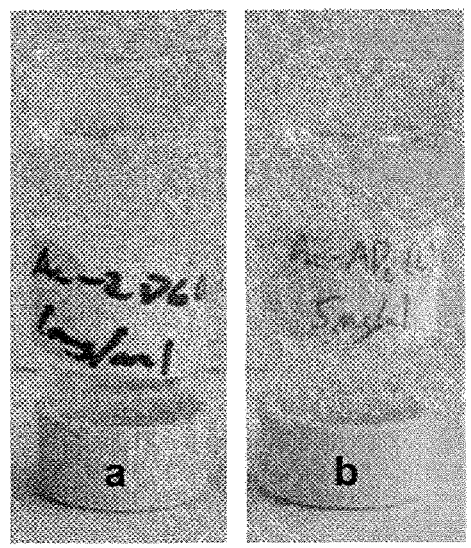
FIG. 2 depicts gelation pictures for peptide based hydro gels at lowest concentrations.
Figure 3:
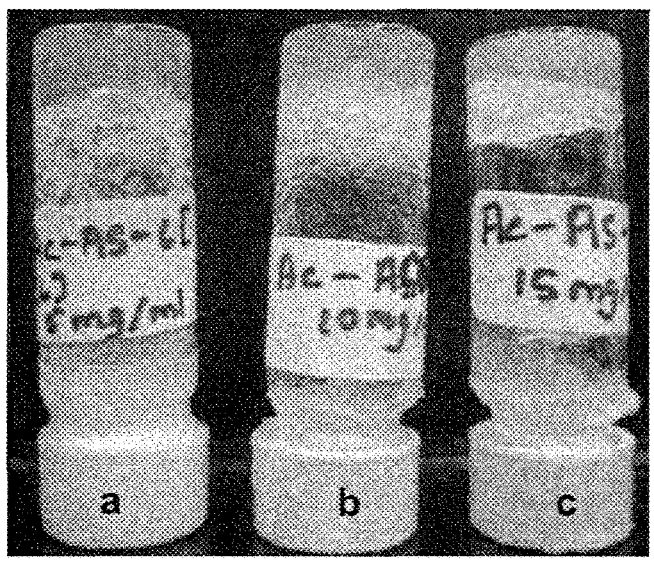
FIG. 3 depicts gelation pictures for Ac-AS-6 (Ac-AIVAGS) (L) at concentrations of 5 mg/ml, 10 mg/ml, 15 mg/ml.
Figure 4:
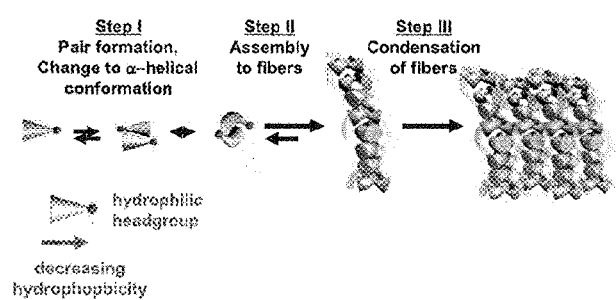
FIG. 4 depicts a hypothesis of self-assembly from peptide monomers to supramolecular network of condensed fibers. (A) Assembly is believed to initiate with antiparallel pairing of two peptide monomers by changing to a-helical conformations. Subsequently, peptide pairs assemble to fibers and nanostructures. Condensation of peptide fibers to fiber aggregates results in hydrogel formation.
Figures 5A, 5B:
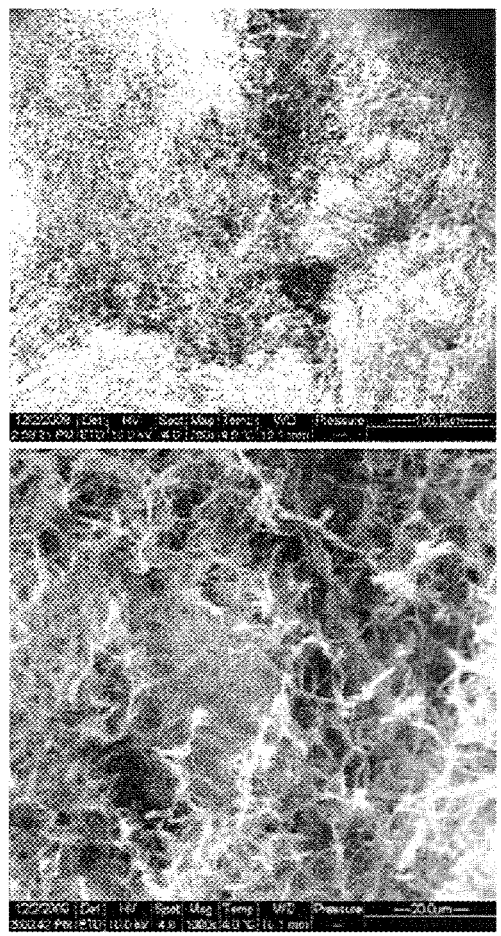
FIGS. 5A-C depict environmental scanning electron microscopy (ESEM) images of hydrogels of Ac-LD6 (Ac-LIVAGD) (L) (10 mg/ml), where
Figure 5C:
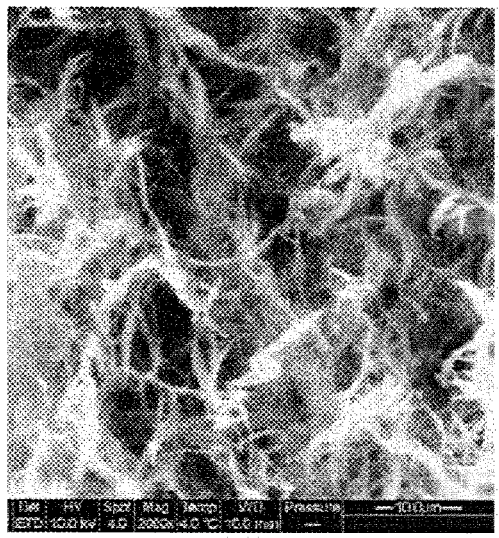
Figure 9A:
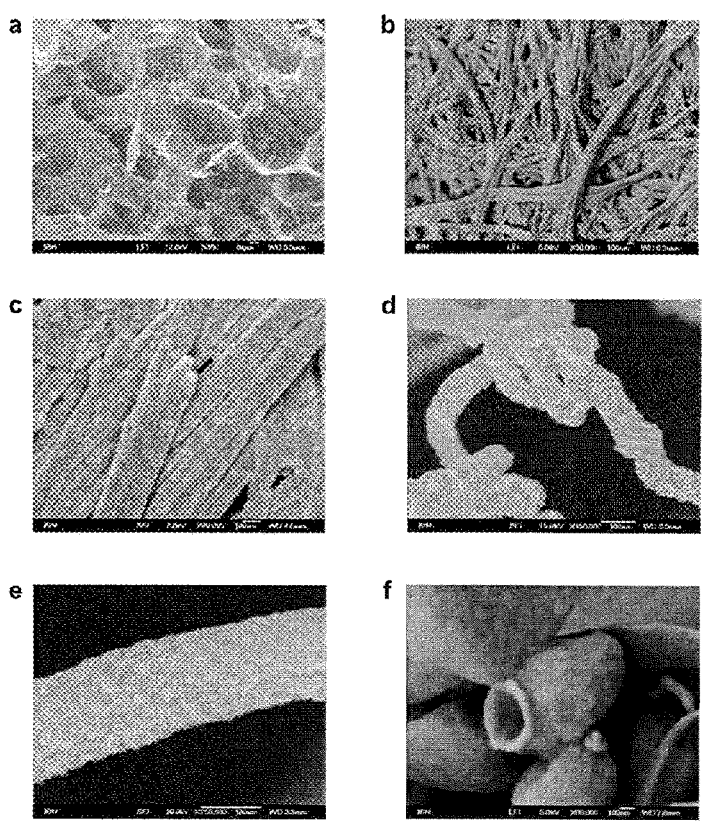
FIG. 9A shows the morphology and structure evaluation of the peptide scaffolds as determined by field emission scanning electron microscopy (a-f). (a) A honeycomb porous structure is observed following lyophilization of 20 mg/mL Ac-AD$_6$ (Ac-AIVAGD) (D) hydrogel. The pores are bounded by membranes of condensed fibers as shown in close-up views of 15 mg/mL (b) and 20 mg/mL (c) Ac-ID$_3$ (Ac-IVD) (L) hydrogels. Further magnification of 20 mg/mL Ac-AD$_6$ (L) hydrogel revealed single fibers (d, e). At lower concentrations, 0.1 mg/mL Ac-LD$_6$ (Ac-LIVAGD) (L), nanostructures are observed (f).
Figure 10A:
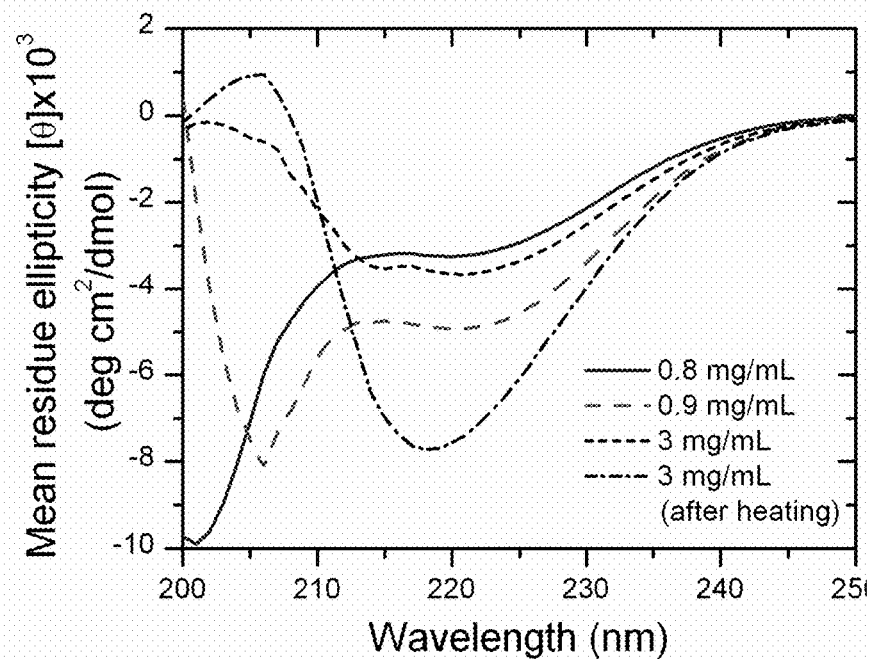
FIG. 10A shows Far-UV CD spectra demonstrating that with increasing concentration there is the transition of Ac-LD$_6$ (Ac-LIVAGD) peptide conformation from random coil (below threshold concentration) to α-helical (222 and 208 nm peaks) and further β-type (negative band at 218 nm) structures. Heating the samples to facilitate gelation increased the β type aggregation.
Figure 10B:
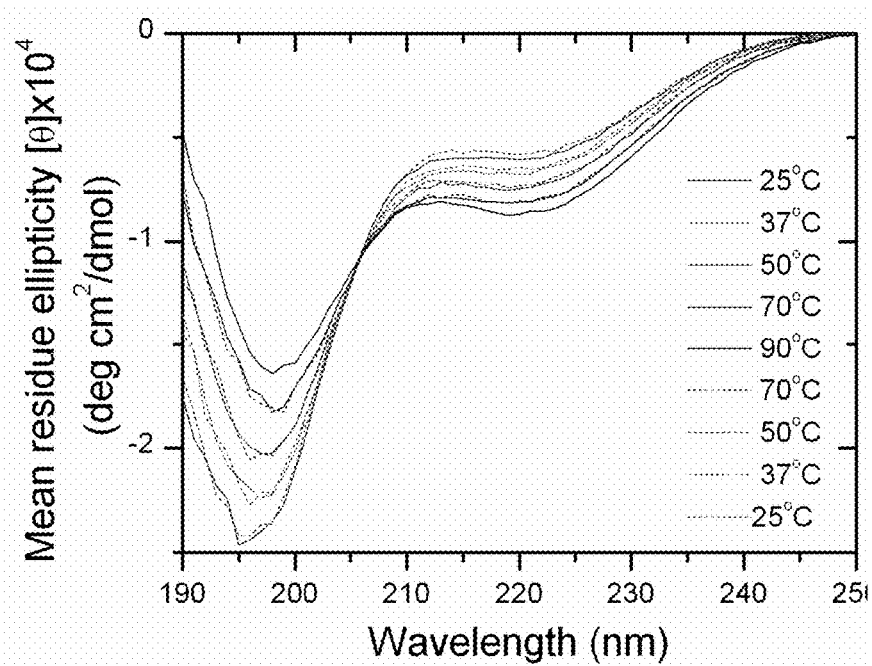
FIG. 10B Below threshold concentration, the random coil conformations of 0.2 mg/mL Ac-LD$_6$ were reversibly affected by step-wise temperature increases (solid lines) from 25° C. to 90° C. and cooling (dotted lines).
Figure 10C:
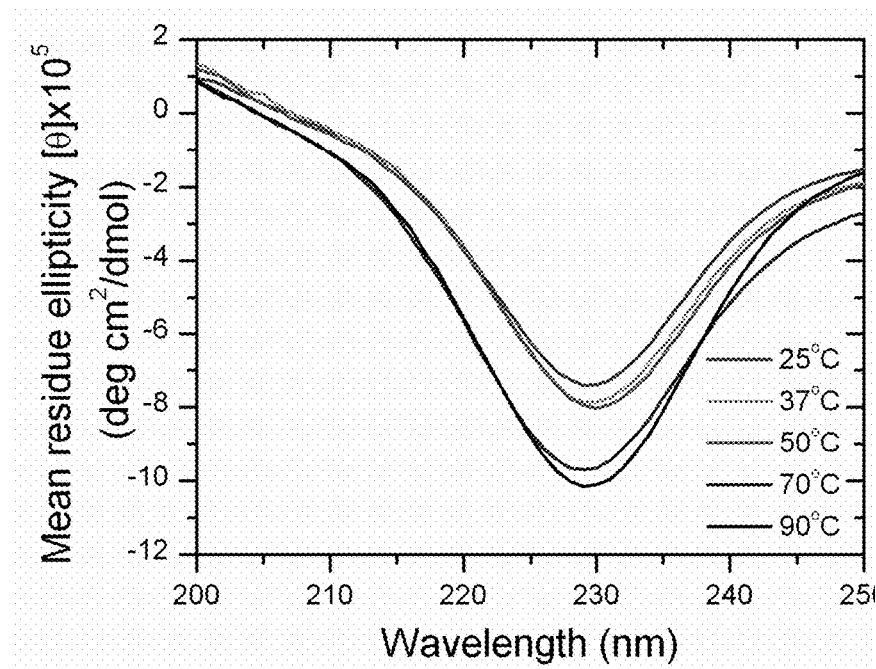
FIGS. 10C and 10D Above the threshold concentration in 1 mg/mL Ac-LD$_6$ gel, stepwise temperature increases FIG. 10C stabilized the β-type structures irreversibly, such that subsequent cooling FIG. 10D did not alter the CD spectra.
Figure 10D:
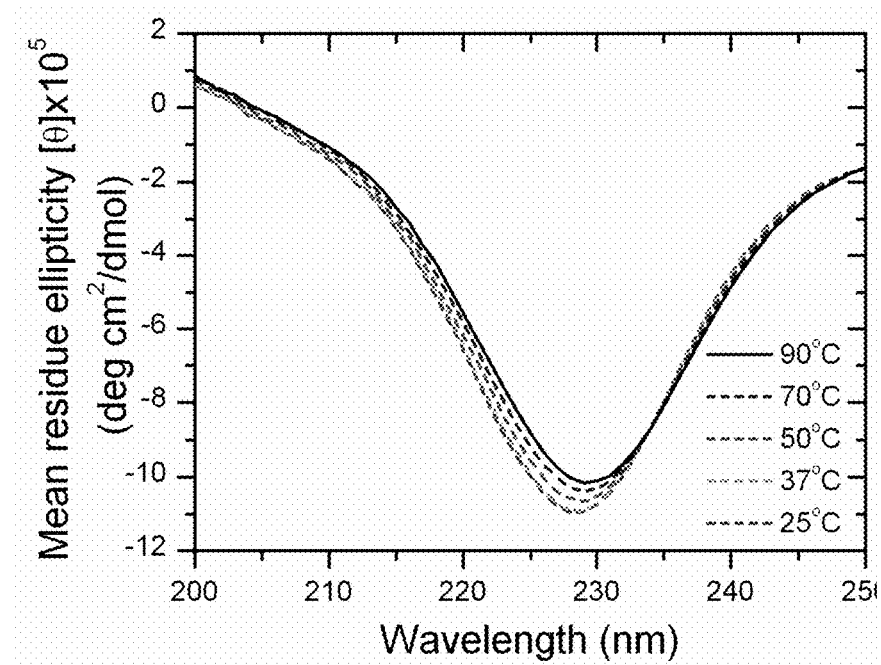
Figure 10E:
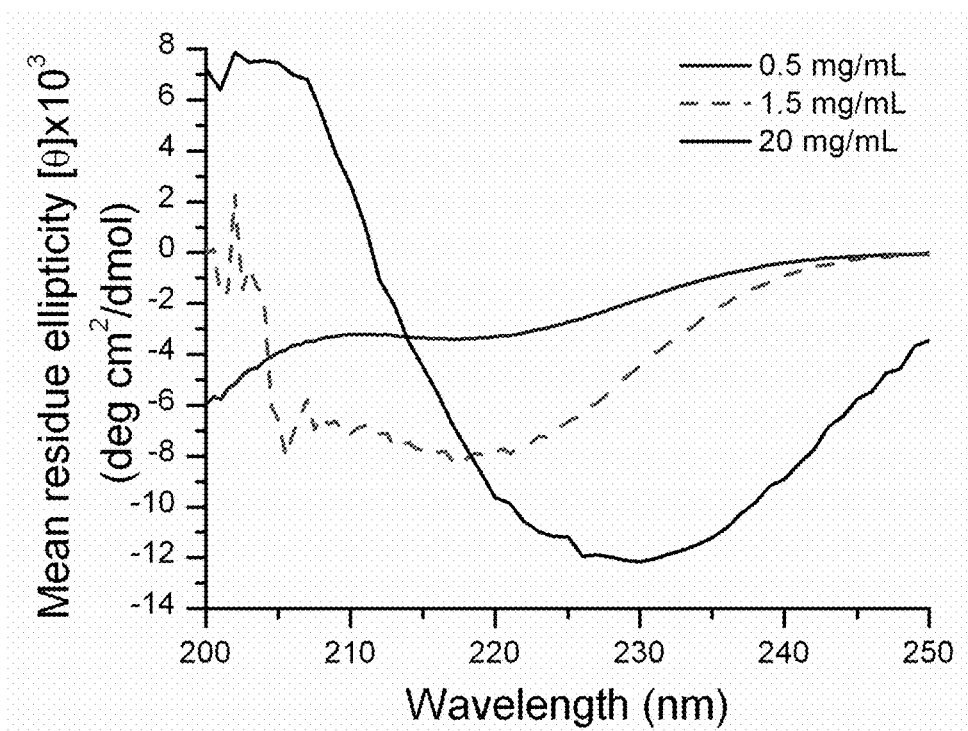
FIG. 10E Far-UV CD spectra of AcID$_3$ (Ac-IVD) at different concentrations. All curves were done at 25° C.
Figure 11A:
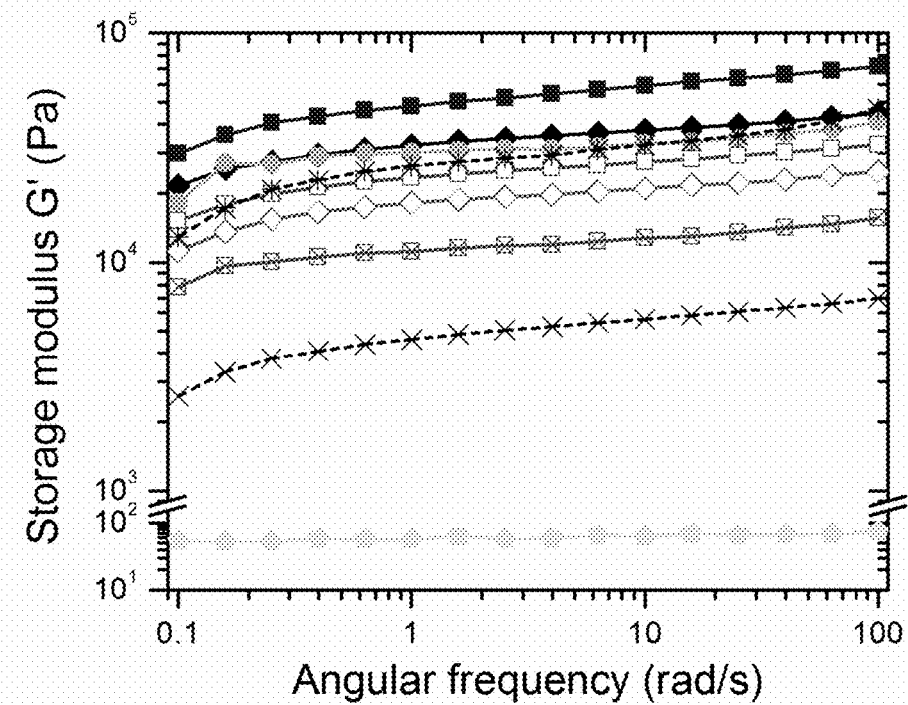
FIGS. 11A and 11B show rheological measurements. The high mechanical strengths of different peptide hydrogels at 20 mg/mL concentration was determined by measuring storage moduli (G') as a function of angular frequency under 0.1% strain, at 25° C. and 50° C. respectively. The gels demonstrate good thermal stability compared to gelatin, which liquified at 50° C. (hence excluded in 4B).
Figure 11B:
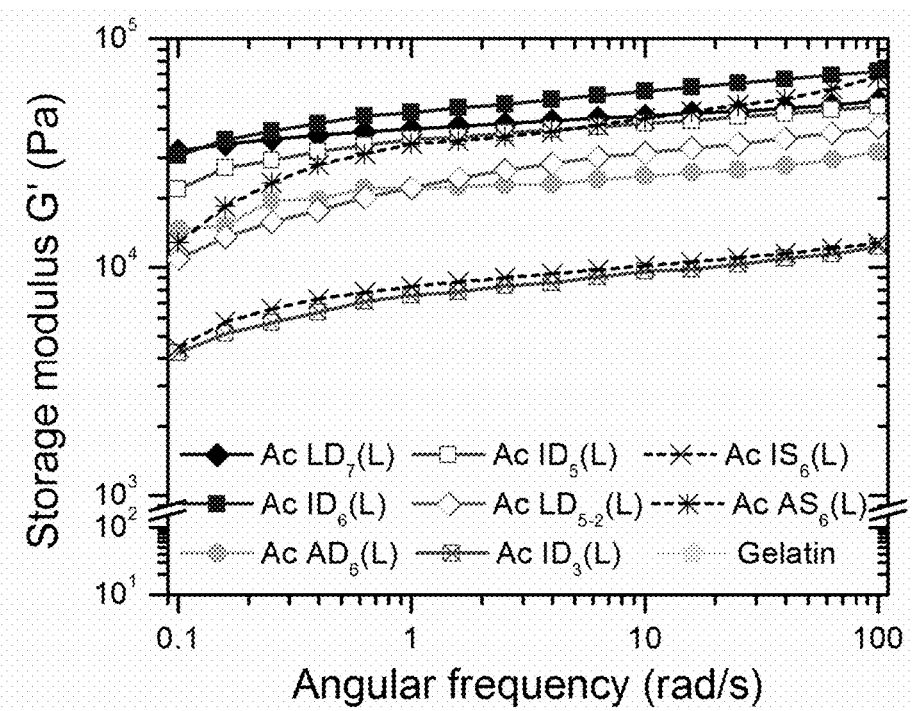
Figure 11C:
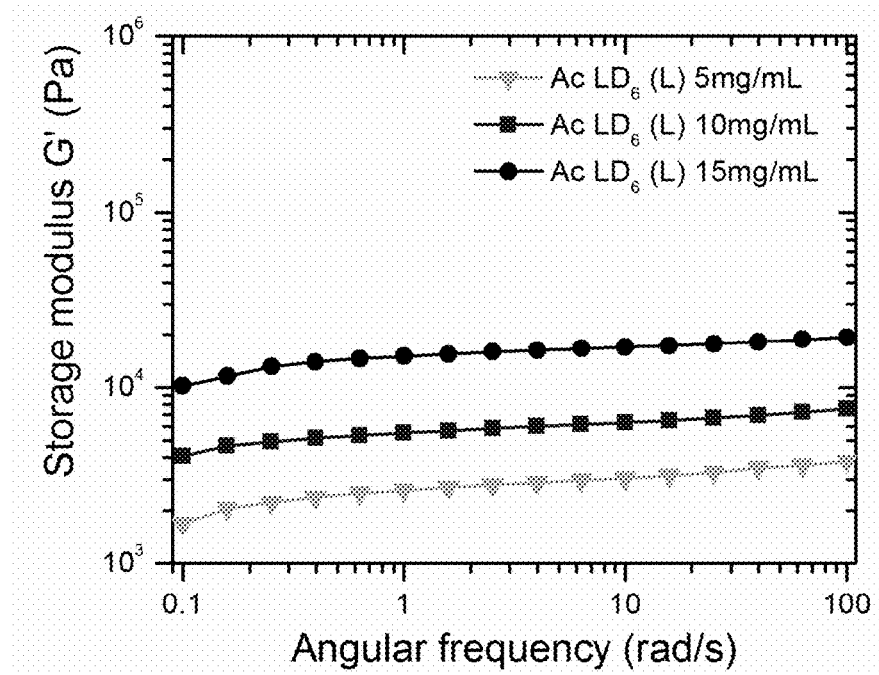
FIG. 11C Mechanical strength is a function of concentration, as determined from oscillatory frequency sweep studies using Ac-LD$_6$ (Ac-LIVAGD) (L) under 0.1% strain at 25° C.
Figure 11D:
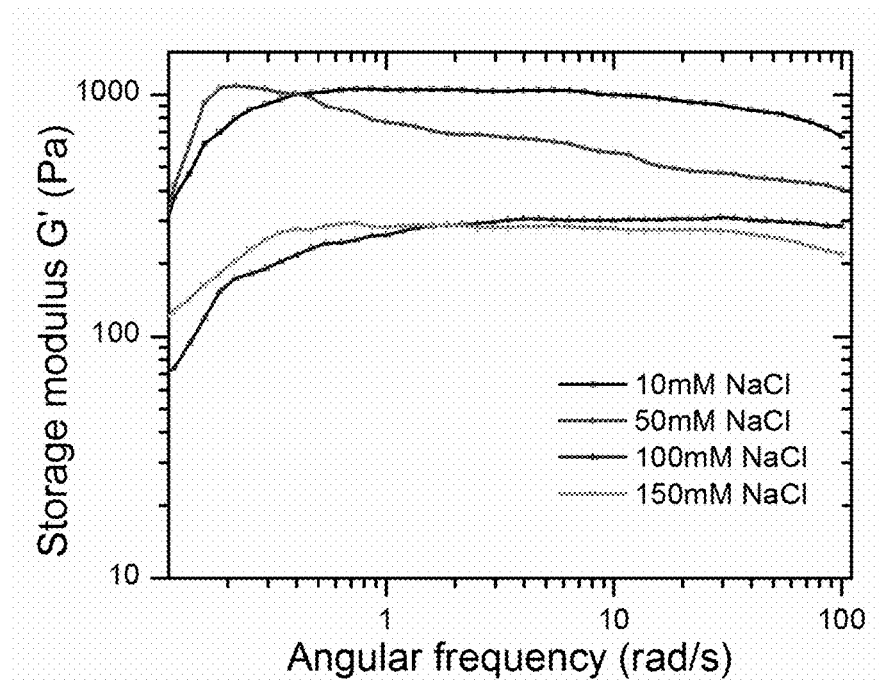
FIG. 11D Increasing salt concentration (NaCl) decreases G', reducing the rigidity of 10 mg/mL Ac-LD$_6$ (L) hydrogels, demonstrating the tunability and reversibility of gelation.
Figure 15A:
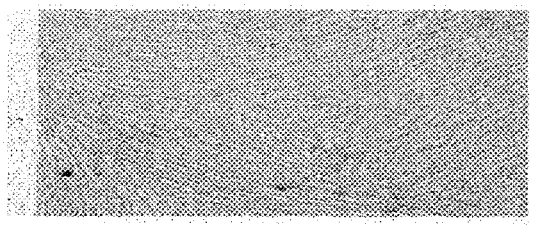
FIGS. 15A-D illustrate the biocompatibility of peptide-based hydrogels of the invention using further cell lines.
Figure 15D:
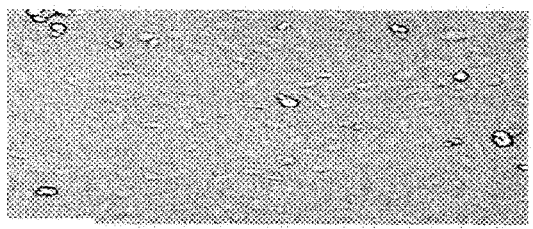
Figure 15B:
Figure 15C:
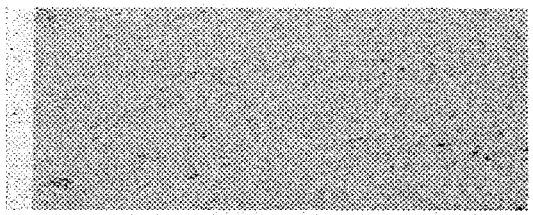
Figure 16A:
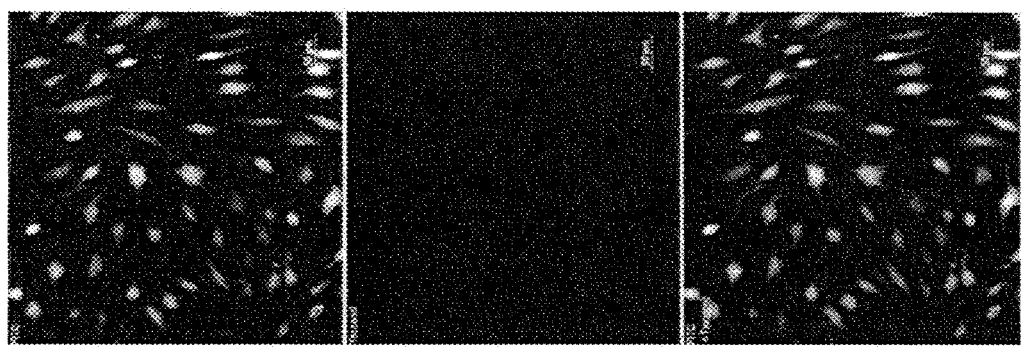
FIGS. 16A-B are further illustrations on the viability of cells in presence of a hydrogel of the invention. Human fibroblast cells were cultured in the presence (FIG. 16A) and absence (FIG. 16B) of Ac-LD$_6$ (Ac-LIVAGD) (L) (5 mg/ml). Fluorescein isothiocyanate (FITC) stained cells (left panels), Texas red stained cells (center panels) and cells stained with both FITC and Texas red (right panels) are shown.
Figure 16B:
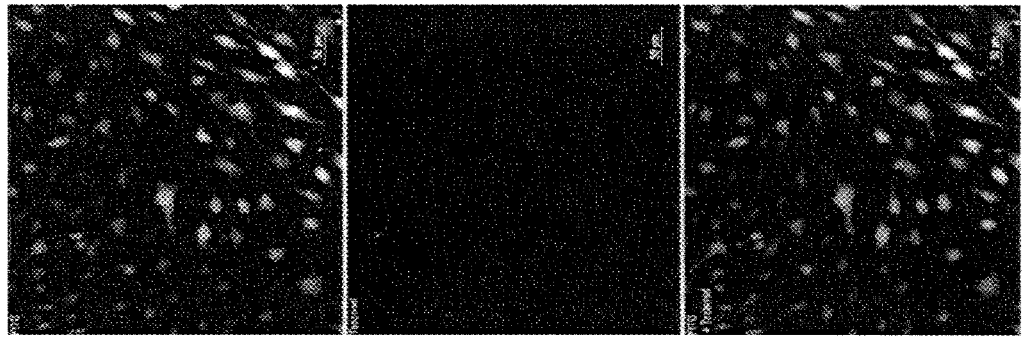
Figure 17:
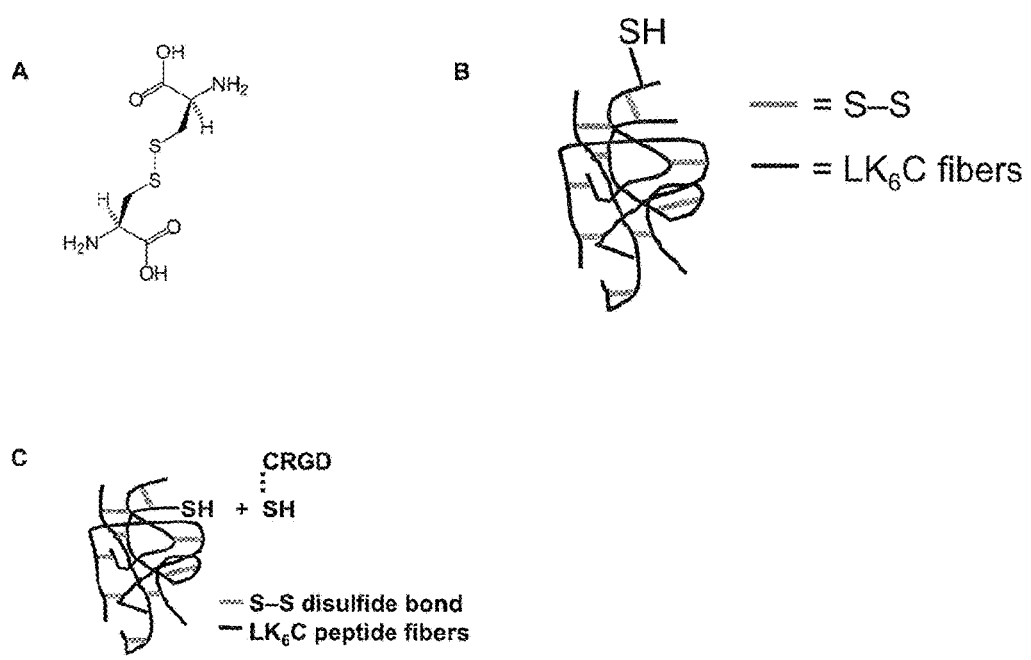

Embodiments of the invention will now be described by way of example with reference to the following figures, in which:

FIG. 17 shows the crosslinking strategy of the present invention using (A) disulfide bridges between two thiol-containing amino acids (here: two cysteines) which introduce (B) chemical intra- and inter-fiber crosslinks among LK$_6$C peptide fibers. The thiol groups further facilitate the conjugation of bioactive agents, such as the integrin binding sequence CRGD (C).

Figure 18:
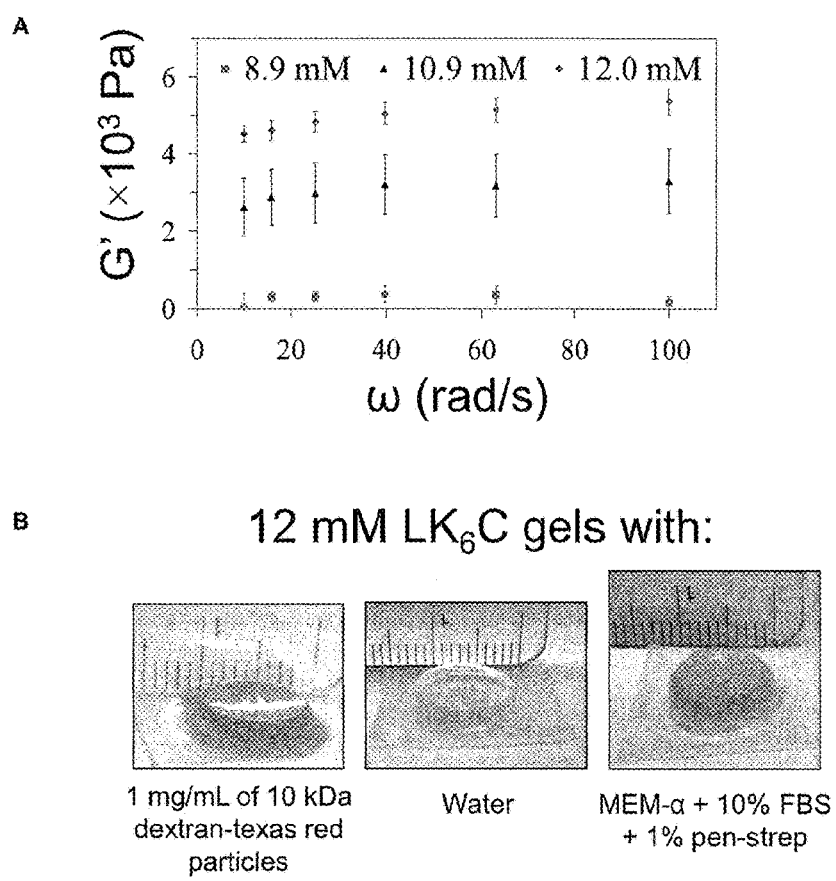

FIG. 18 at A illustrates the determination of a suitable gelation concentration with the LK$_6$ control peptide sequence. A working concentration was established that was suitably low so as to save on material during testing but yet, capable of forming gels strong enough to be manipulated. LK$_6$ gels were therefore casted at different concentrations and their stiffness was measured (average±s.d. of triplicates). As expected, G' values increased with peptide concentration and it was determined that a working concentration of 12 mM afforded gels with sufficient mechanical integrity to withstand handling. FIG. 18 at B shows that gels can be formed with 12 mM of LK$_6$C (~10 mg/mL after accounting for an amino acid content of 89.4%) and that gel formation is compatible with various aqueous media.

Figure 19:
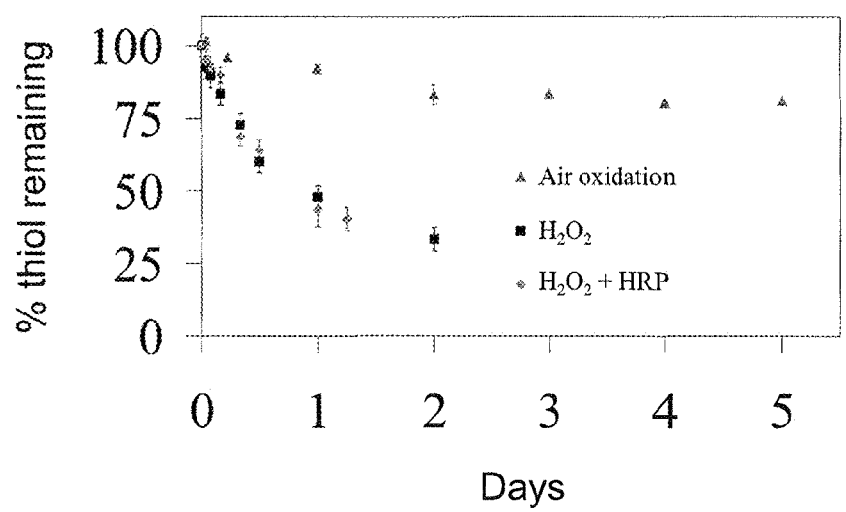

FIG. 19 shows the kinetics of disulfide formation when LK$_6$C was subjected to oxidation by air, as compared to H$_2$O$_2$-assisted oxidation+/−HRP (average±s.d. of duplicates). For oxidation by air, LK$_6$C dissolved in water at 12 mM was left in capped micro-centrifuge tubes at room temperature. As can be seen, kinetics of disulfide formation was sluggish and ~80% of thiols still remained after 5 days, as determined using an Ellman's assay. H$_2$O$_2$-assisted oxidation was much more efficient in the formation of disulfide bridges. Interestingly, horse-radish peroxidase (HRP, 0.6 U/mL), an enzyme commonly used with H$_2$O$_2$ to boost oxidation efficiency, did not significantly increase the rate of disulfide formation.

Figure 20:
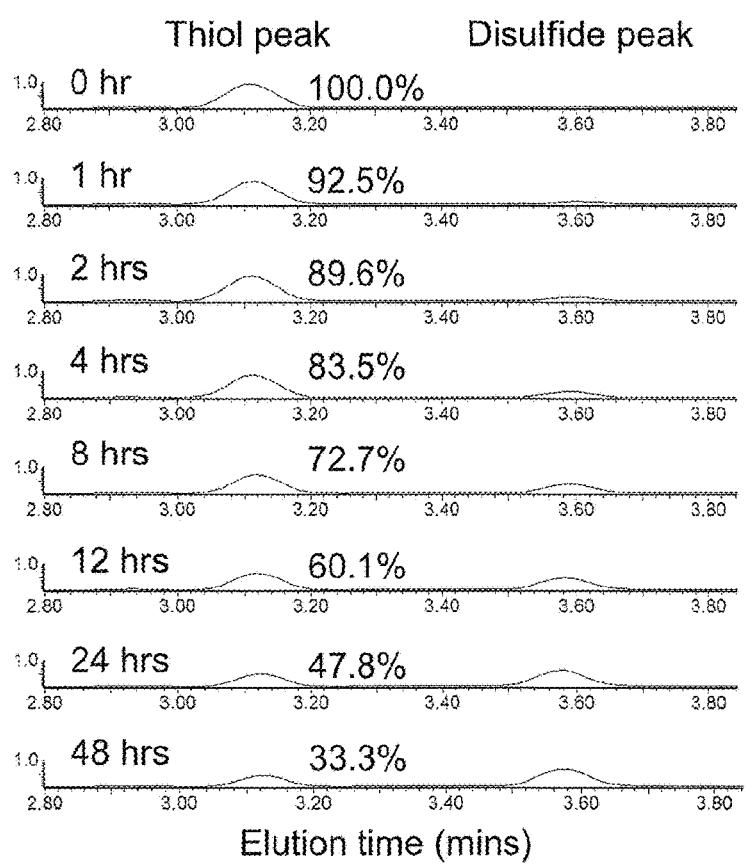

FIG. 20 shows representative UPLC chromatograms where the area under the peaks were used to follow the rate of disulfide formation in H$_2$O$_2$-assisted oxidation. 12 mM LK$_6$C dissolved in water containing 0.06% H$_2$O$_2$ was used, and the disulfide peak at ~3.6 min gradually increased. Only ~50% of thiols remained after 1 day. The $R^2$ value of the thiol calibration curve was 1.000.

Figure 21:
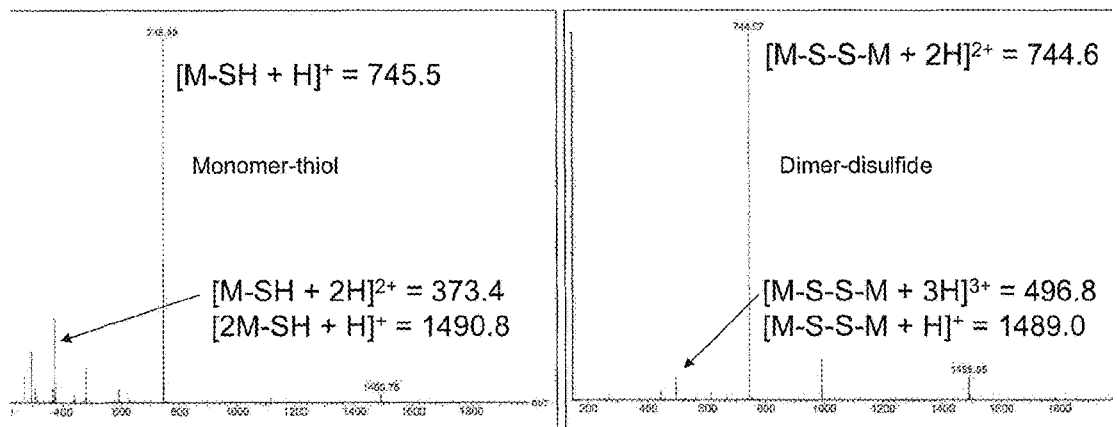

FIG. 21 shows mass spectra corresponding to the a) LK$_6$C monomer-thiol and b) (LK$_6$C)$_2$ dimer-disulfide peaks in the UPLC elution profile. In both cases, the expected masses were detected and verified the assignment of peaks.

Figure 22:
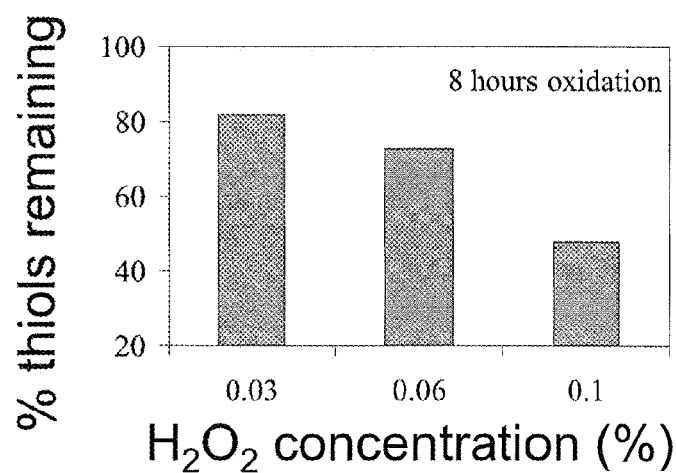

FIG. 22 shows the effect of the H$_2$O$_2$ concentration on the rate of disulfide formation. LK$_6$C was incubated with different concentrations of H$_2$O$_2$ for eight hours at 25° C. before UPLC analysis. The area under the thiol peaks were then normalised to that at 0 hour to give the % of thiol remaining. Before that, a calibration curve had been generated with pure LK$_6$C as standard ($R^2$=0.999). As expected, a higher concentration of H$_2$O$_2$ increased the kinetics of disulfide formation. However, as a compromise between oxidation efficiency and H$_2$O$_2$-associated toxicity, 0.06% H$_2$O$_2$ was chosen for subsequent experiments.

Figure 23:
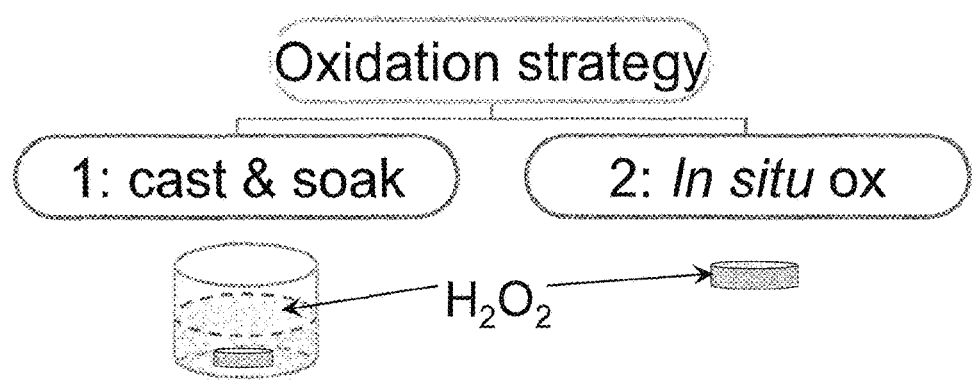

FIG. 23 illustrates two different methods to effect crosslinking: 1) cast-and-soak: gel is first formed in water and then soaked in a H$_2$O$_2$ solution for the desired amount of time. 2) in situ oxidation: LK$_6$C peptide powder is dissolved directly in water containing H$_2$O$_2$ to form the gel.

Figure 24:
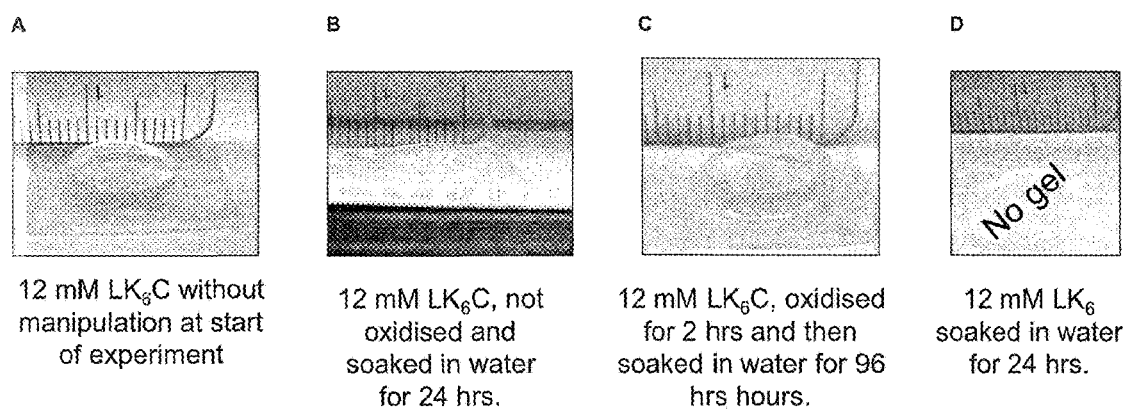

FIG. 24 shows that oxidation dramatically improved the ability of the gels to retain their shapes, as seen in panels A to D: (A) LK$_6$C gel casted at the start of experiment which was either (B) not oxidised and soaked in water for 24 hours, or (C) oxidised for two hours and soaked in water for 96 hours. (D) The control peptide sequence, LK$_6$, did not survive the 24-hour water soak.

Figure 25:
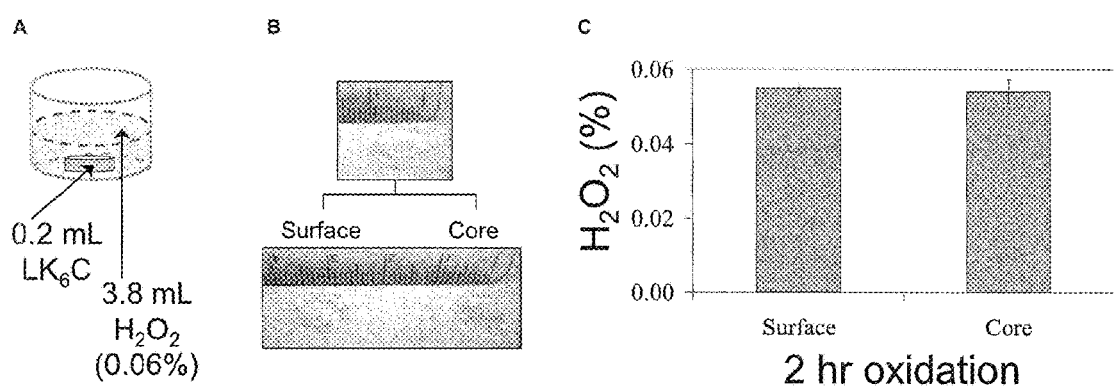
Figure 26:
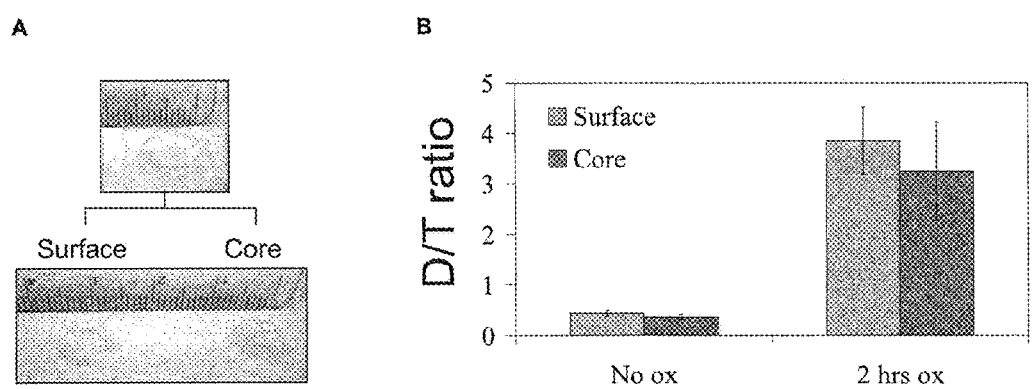

FIG. 25 and FIG. 26 show that the hydrogel was uniformly oxidised in the cast-and-soak method. In the cast-and-soak method, LK$_6$C was dissolved in water, casted overnight in a ring mould before being soaked in a solution containing $H_2O_2$ for the desired amount of time (FIG. 25A). To investigate if oxidation was uniform throughout the bulk or enriched only in the surface layers, the gel was removed from the $H_2O_2$ solution after two hours and carefully separated into its surface (top, bottom and circumference) and core fractions using a surgical blade (FIG. 25B and FIG. 26A). The amount of $H_2O_2$ in the respective fractions was quantified using the PeroXOquant $H_2O_2$ assay kit (Pierce, Ill., USA), according to the manufacture's recommendations (average±s.d. of triplicates). Samples were always diluted such that absorbance readings fell within the linear portion ($R^2=0.999$) of the calibration curve obtained with $H_2O_2$ standards (FIG. 25C). The gel fractions were also analysed using UPLC (FIG. 26B; average±s.d. of duplicates). To normalise for any differences in fiber density between the surface and core layers, the area ratio between the disulfide and thiol (D/T) peaks was taken to indicate the extent of oxidation that had occurred in the fractions. As can be seen, the amount of $H_2O_2$ detected in both the fractions was comparable, suggesting that the diffusion of small $H_2O_2$ molecules was extremely efficient. Compared to without oxidation, the D/T ratio of both layers was, as expected, significantly elevated after oxidation. However, the D/T ratio of the surface and core layer was insignificantly different after oxidation, indicating that the gel was uniformly oxidised in the cast-and-soak method.

Figure 27:
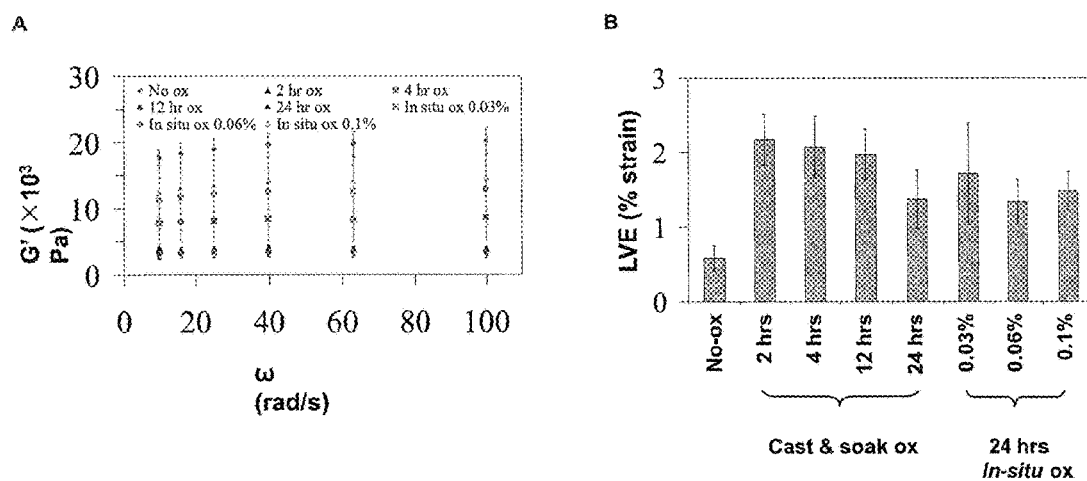

FIG. 27 illustrates the rheological properties and the effects of oxidation on the microstructure and ability of $LK_6C$ gels to retention their shape. The (A) stiffness and (B) elasticity of $LK_6C$ gels were measured after various oxidation regimes (average±s.d. of triplicates). Generally, elasticity increased whereas stiffness was either maintained or increased after the introduction of S—S bonds.

Figure 28:
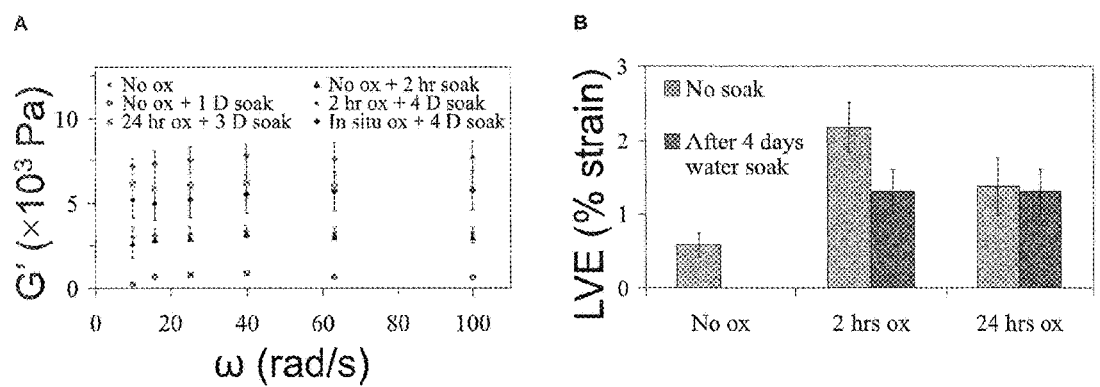

FIG. 28 illustrates the rheological properties of oxidized hydrogels. 12 mM $LK_6C$ gels were subjected to various oxidation regimes with 0.06% $H_2O_2$ and various durations of water soak before their (A) stiffness and (B) elasticity were measured (average±s.d. of triplicates). Without oxidation, $LK_6C$ gels could maintain their stiffness after two hours of water soak but broke down and lost their stiffness after 24 hours of water soak. On the other hand, gels subjected to 2 or 24 hours of cast-and-soak oxidation, or 22 hours of in situ oxidation maintained their shapes and in fact, became stiffer after up to four days of water soak. Presumably, the introduction of chemical S—S bonds was important in helping to keep the peptide fibers together and increase the ability of the gels to maintain their shape and stiffness. Compared to gels without oxidation, the increase in elasticity of the oxidised gels was also maintained after up to four days of water soak.

Figure 29:
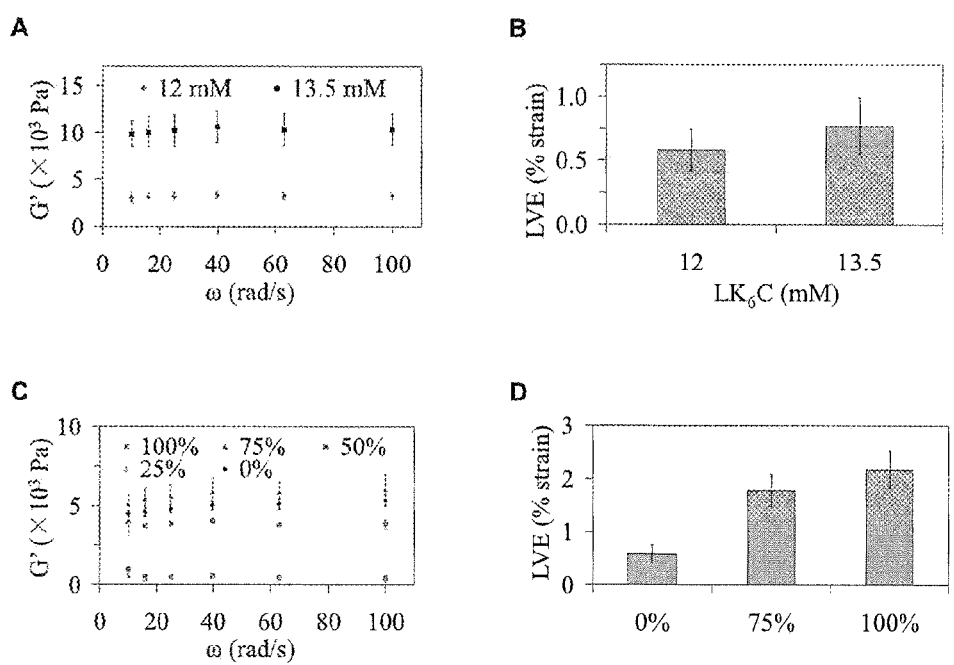

FIG. 29 shows the effects of concentration and LK6-doping on the rheological properties of $LK_6C$. $LK_6C$ was dissolved in water at 12 or 13.5 mM and casted overnight in a ring mould. The (A) stiffness and (B) elasticity of the gels were then measured (average±s.d. of triplicates). Increasing the concentration of $LK_6C$ increased the gel stiffness significantly but only resulted in a modest increase in elasticity. (C-D) $LK_6C$ was also mixed with varying amount of LK6 to a final concentration of 12 mM in water and casted overnight in a ring mould. The "%" values presented above refer to the proportion of $LK_6C$ in the formulation. The gels were then soaked in a 0.06% $H_2O_2$ solution for two hours (i.e., cast-and-soak) before their (C) stiffness and (D) elasticity were measured (average±s.d. of triplicates). As can be seen, pure $LK_6C$ (100%), pure LK6 (0%) and $LK_6C$/LK6 75/25 (75%) gels were relatively stiff. Gels containing ≤50% $LK_6C$, however, broke down before/during handling, resulting in low G' values. These suggest that the window to dope $LK_6C$ with $LK_6$ (at a final concentration of 12 mM) while still maintaining gel stiffness, lies between 75-50% of $LK_6C$. Gels containing oxidised $LK_6C$ were more elastic than pure $LK_6$ gels. However, the difference in elasticity between gels containing 75% and 100% of $LK_6C$ was only modest.

Figure 30:
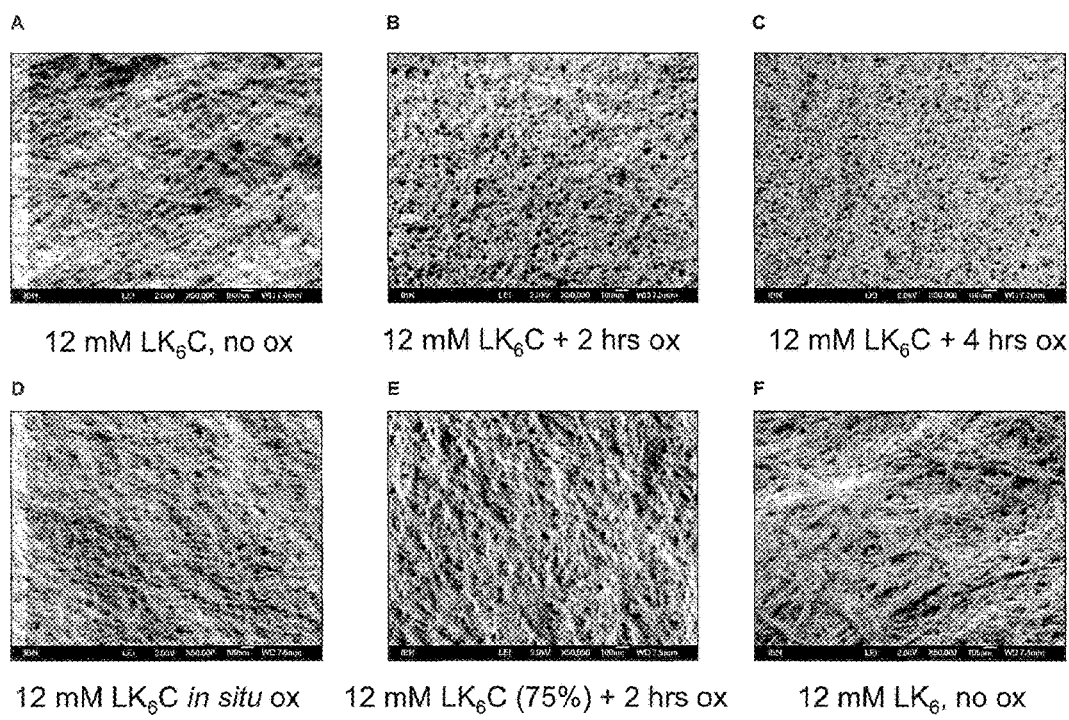

FIG. 30 depicts FESEM images showing that the fibrous microstructure of $LK_6C$ was maintained after oxidation. Freeze-dried gels were deposited onto carbon tapes, sputtered with platinum and observed under a JSM-7400F electron microscope (Jeol, Tokyo, Japan).

Figure 31:
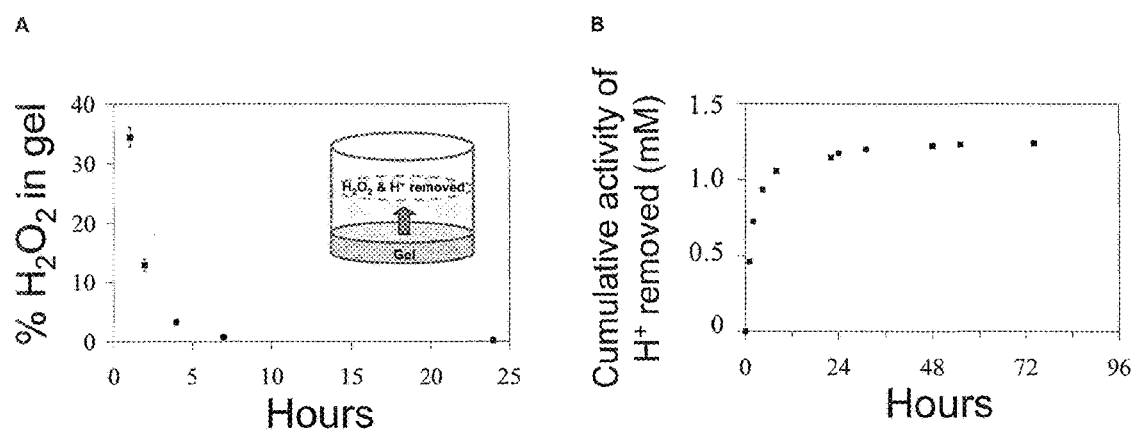

FIG. 31 illustrates the purification of hydro gels before their use in cell culture. $LK_6C$ was dissolved in 200 µL of water containing 0.06% $H_2O_2$ and casted directly into a 48-well plate for 22 hours at 25° C. 1 mL of water was then added on top of the gel and replaced at regular time intervals to leach out (A) unreacted $H_2O_2$ and (B) residual $H^+$ from solid-phase peptide synthesis (average±s.d. of duplicates at least). The amount of $H_2O_2$ in the supernatant was quantified as before and plotted with respect to time. The total amount of $H_2O_2$ at the start of experiment was obtained by: sum of all removed $H_2O_2$ in the supernatants+whatever amount of $H_2O_2$ remaining in the gel at the end of experiment. The amount of $H^+$ removed was determined by measuring the pH of the supernatant with respect to control wells with no gel (only water). Since pH is proportional to the negative logarithm of the activity of $H^+$ ions, the amount of $H^+$ removed from the gel can be calculated with respect to the control wells, which account for natural air acidification. Experiment was stopped when pH of supernatant matched that of the control wells and cumulative activity of $H^+$ removed was plotted as a function of time. As can be seen, >96% of $H_2O_2$ was removed after 4 hrs and >99% after 7 hrs. Similarly, >85% of residual acid was removed after 8 hrs. We however note that as the purification efficiency is diffusion controlled, the plots above are only valid for the reported frequency of water change. A more frequent regime of water change or using a buffered media (e.g., growth media or PBS) instead of water is expected to give even better results.

Figure 32:
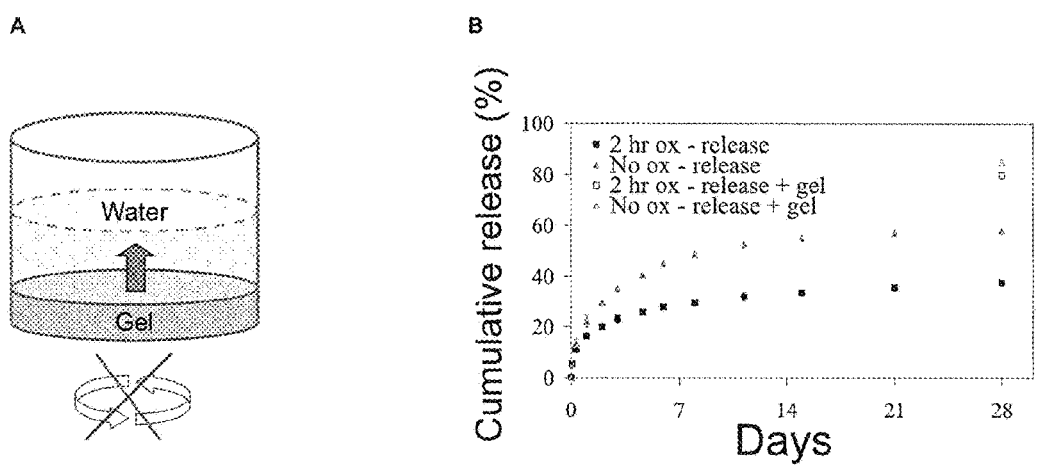

FIG. 32 illustrates the gradual and tunable release kinetics of the hydro gels according to the present invention. $LK_6C$ containing 1 mg/mL of dextran-dye (10 kDa) was first casted in 48-well plates and incubated overnight. The hydrogel was either not oxidized or oxidized for 2 hrs before water was introduced at room temperature. Water was then extracted to assay for dextran release from the hydrogel ($R^2$ of calibration curve was 0.999). The release profile showed no burst release, but a gradual release up till 28 days. The release rate of the oxidized hydrogel was lower, presumable due to its greater stability in water.

Figure 33:
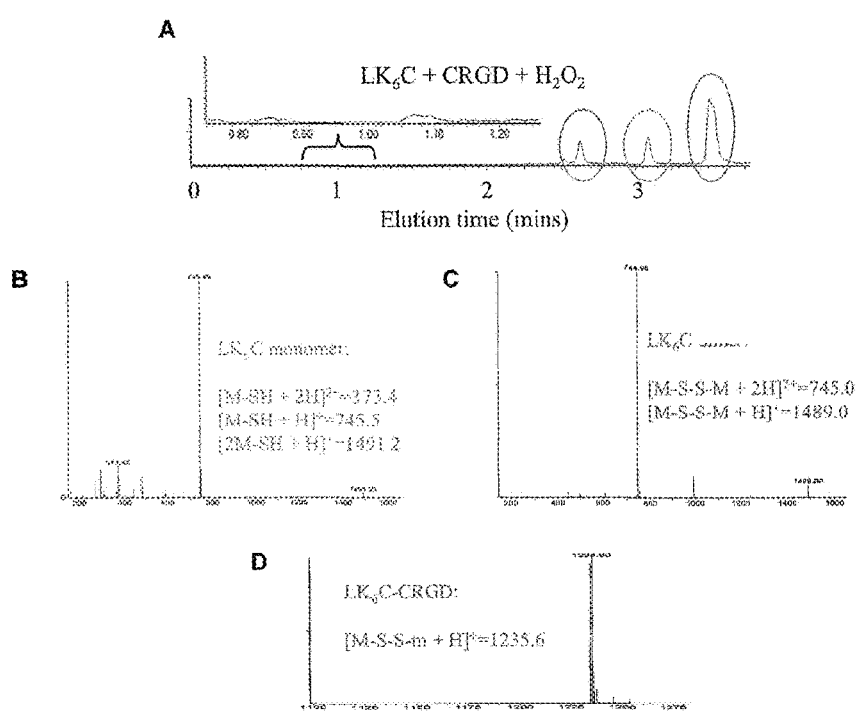

FIG. 33 shows the chemical conjugation of CRGD onto $LK_6C$ fibers via cysteine-mediated disulfide bonds. CRGD was mixed with $LK_6C$ in the presence of 0.06% $H_2O_2$ and casted in a ring mould at 25° C. for 22 hours. (A) UPLC later revealed that there were three main peaks in the chromatogram which could be assigned, based on their respective MS, to: (B) unreacted $LK_6C$ monomers, (C) ($LK_6Ch$ dimers and (D) disulfide-linked $LK_6C$–CRGD conjugates. All peaks have been colour-coded to facilitate interpretation. Earlier experiments also determined that unreacted CRGD monomers or $(CRGD)_2$ dimers eluted at ~1.1 min (data not shown), both of which were not observed here (see magnified inset of A). The integrin-recognition motif, CRGD was therefore successfully conjugated onto $LK_6C$ fibers. The conjugation of the CRGD motif is only intended to illustrate the versatility of this platform and the simplicity of reaction conditions. Future conjugations need not be limited to this sequence.

Figure 34:
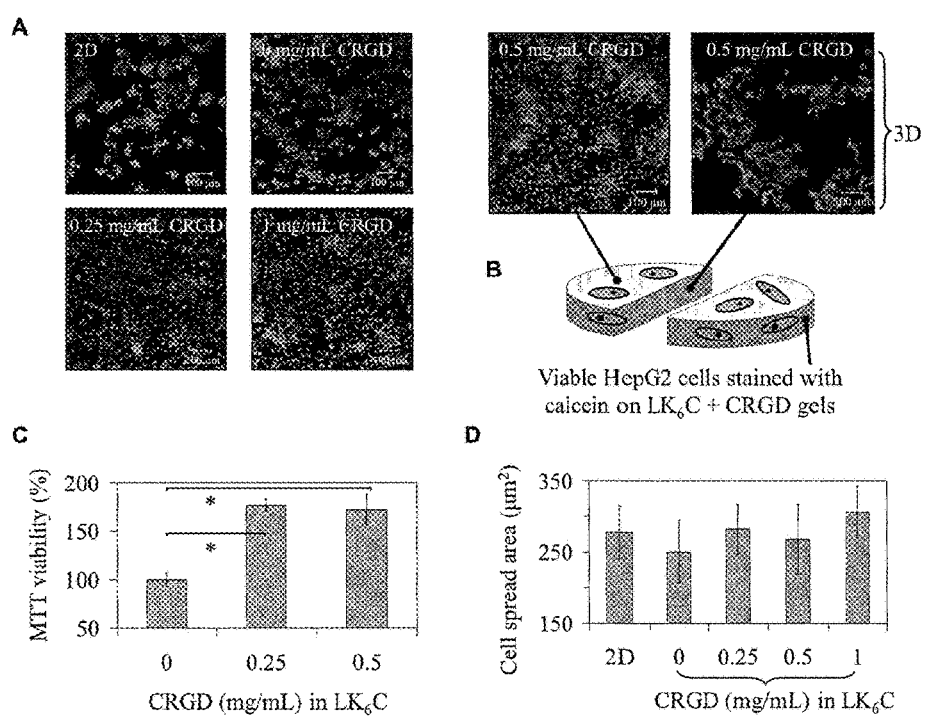

FIG. 34 shows the effects of 3D cell culture and the incorporation of RGD on the viability and spreading of HepG2 cells. (A) En face views of viable cells stained with calcein cultured on regular 2D surfaces for four days, compared to cells in $LK_6C+/-RGD$ gel culture. All images, except for the 2D culture, were mergers of several z-stacks. (B) Cells were viable, as evident from the positive calcein signals, after four days of culture on the RGD functionalised, crosslinked and purified $LK_6C$ gels. 3D distribution was also achieved, as con-31 firmed by cross-sectional slices which revealed multi-layered cell growth. The presence of RGD increased the viability of cells, as visually suggested in (A) and corroborated by (C) the MTT assay. (D) In the case of HepG2 cells, $LK_6C$ gel culture in the presence or absence of RGD had insignificant effects ($p>0.05$) on cell spreading compared to those in regular 2D culture. (C-D) Average±s.d. of triplicates at least.

Figure 35:
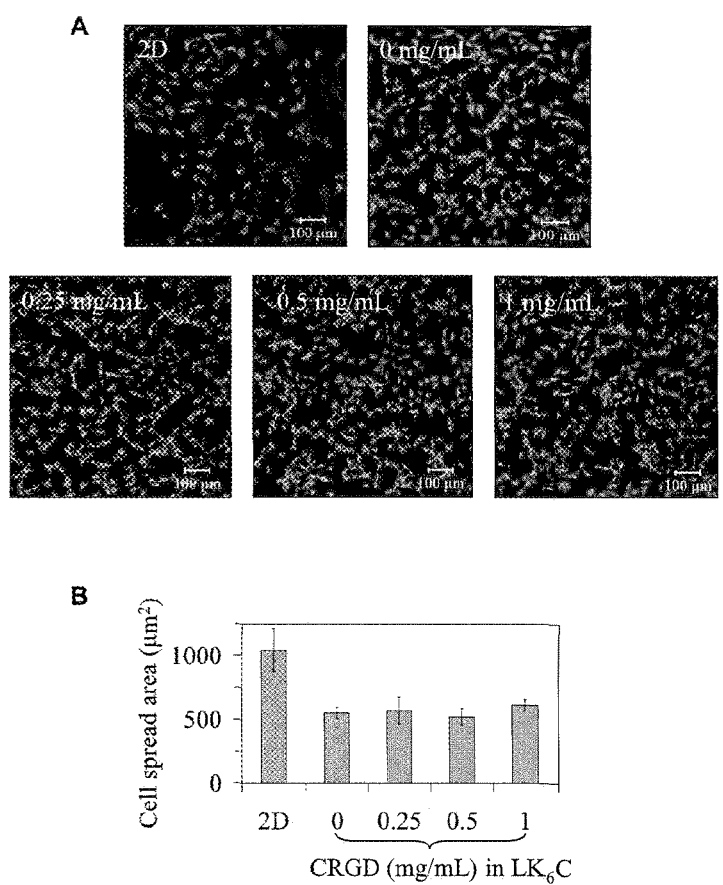

FIG. 35 illustrates the 3D primary cell culture and their cell-spread area. (A) Fibroblasts isolated from the cornea/sclera of New Zealand White rabbits were maintained in regular completed DMEM and grown in 2D culture or purified $LK_6C$ gels+/-various concentrations of CRGD. Cells were incubated for four days before they were stained with calcein AM for confocal imaging. Images from gel cultures were mergers of several z-stacks. As observed, viable fibroblasts were seen in all cases. In the case of 2D culture, it was repeatedly observed that the cells were heterogeneously distributed throughout the well area, i.e., the middle of the well was sparsely populated while the edges were confluent. Cells in gel culture, on the contrary, were evenly distributed across the gel. We note that seeding of cells was done on the same day using the same methods and most probably did not account for the in homogeneous distribution of cells. (B) Images taken at a higher magnification were then analysed using the ImageJ software to quantify the average cell-spread area of the fibroblasts (Average±s.d. of triplicates at least). The rabbit fibroblasts spreaded more in 2D culture compared to those in the various gel cultures (ANOV A, $p<0.05$). There were no significant differences in terms of cell-spread area between gels with or without CRGD in them.

Figure 36:
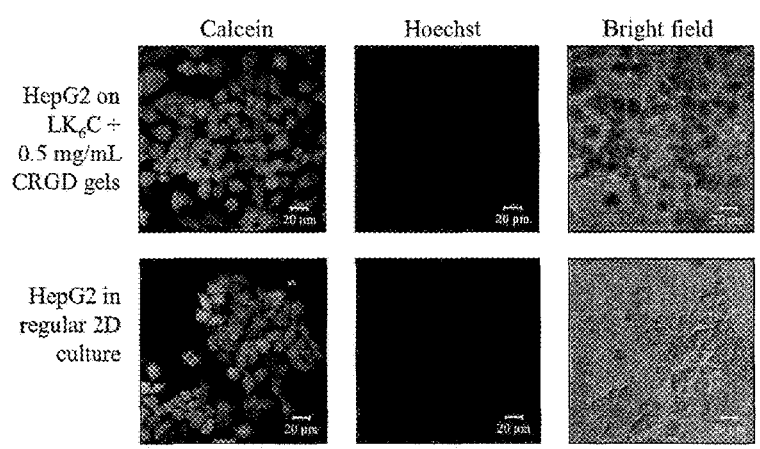

FIG. 36 shows confocal images (40× magnification) of HepG2 cells either cultured on $LK_6C$/CRGD gels or on regular 2D wells. In the former, the image presented was a merger of several z-stacks. Cells were stained with calcein AM and Hoechst (Invitrogen, Singapore) prior to confocal observations. The images from at least two independent locations were then processed with the ImageJ software to quantify the average spreading area of cells.

Figure 37:
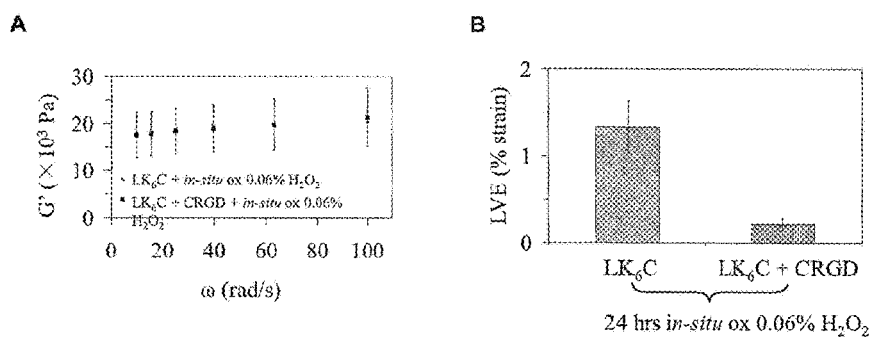

FIG. 37 shows the rheological properties of gels of $LK_6C$ (10 mg/mL) with or without CRGD (1 mg/mL) were casted overnight in the presence of 0.06% $H_2O_2$ before their (A) stiffness and (B) elasticity were quantified with oscillation rheometry (Average±s.d. of triplicates). Upon CRGD conjugation, the gel maintained their stiffness but became less elastic.

Figure 38:
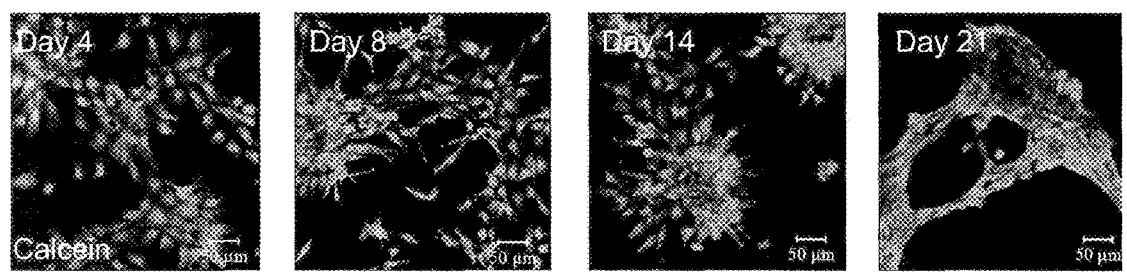

FIG. 38 shows that 3T3 murine fibroblasts cultured in 3D in $LK_6C$+CRGD hydrogels remained viable for at least 21 days. Cells were stained with calcein AM prior to confocal microscopy.

Figure 39:
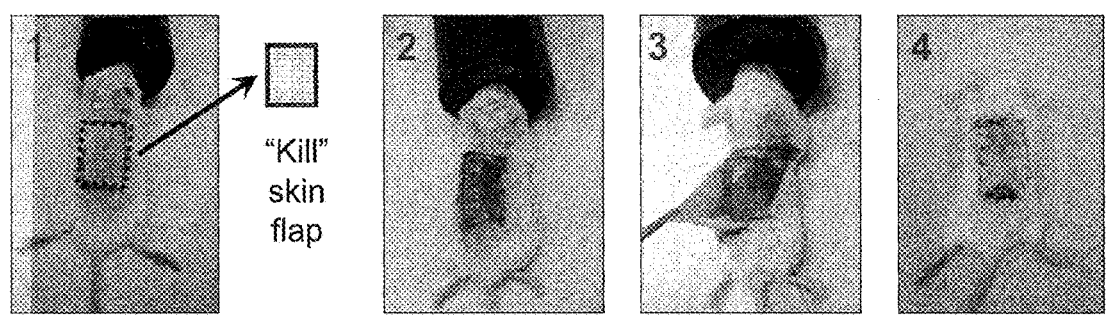

FIG. 39 illustrates the surgical procedure used for testing $LK_6C$+CRGD hydrogels in the treatment of wounds. (1) Hair was removed, and the area for surgical removal was marked. Both the epidermis and dermis were removed to simulate injury. The removed skin flap was killed by a repeated cycle of freezing and thawing. (2) Mouse with open wound. (3) $LK_6C$+CRGD hydrogels with or without 3T3 fibroblast cells were placed onto wound and the killed skin flap was sutured back to act as a bandage dressing. (4) Mouse after skin flap dressing was sutured back.

Figure 40:
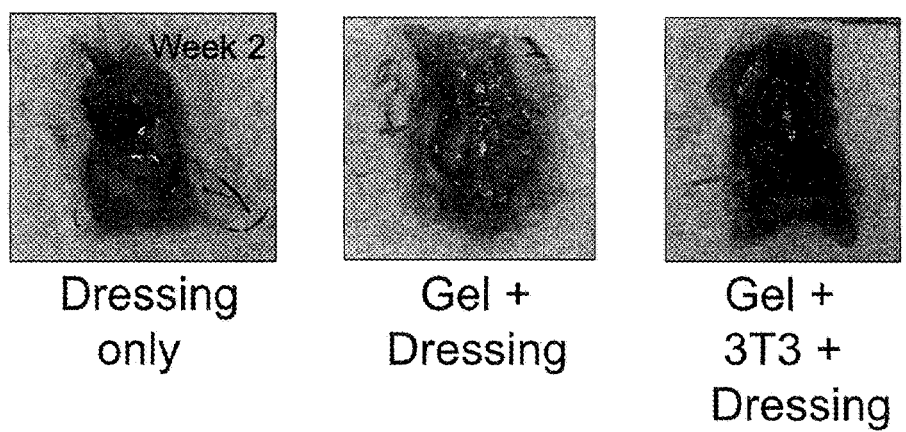

FIG. 40 shows that hydrogel treatment promotes vascularisation in wounds (see red arrows). Preliminary data obtained with H&E stained slides revealed that the gel+3T3+dressing group has the most significant re-epithelisation and regeneration of a thicker dermis (data not shown).

DETAILED DESCRIPTION OF THE INVENTION

The inventors have previously described short peptide sequences (3-7 residues) capable of self-assembly into helical fibers that ultimately result in hydrogel formation. While these peptides have good mechanical properties and can entrap large amount of water, they rely purely on physical forces to keep the interwoven fiber network together. Consequently, some peptide sequences—one example of which is LIVAGK, or abbreviated to LK6—are typically used at rather high concentrations to ensure the integrity and stability of the gel in aqueous solution. This has contributed significantly to cost.

The present invention as defined above offers significant improvements in material properties such as stiffness, elasticity and resistance of the gel to degradation compared to previous disclosures-ultra-small peptide-based and peptide/polymer-based hydrogels. Reactive chemical groups are also introduced to the peptide fibers which allow the facile in-situ chemical conjugation of biological signals. Furthermore, compared to previous formulations, less material is now needed for gelation (e.g. 10 mg/ml $LK_6C$ instead of 25 mg/ml for LK6), which translates into significant cost savings and higher water contents. This class of material is suitable for biomedical applications, for example but not limited to, three-dimensional cell culture, tissue engineering, sensing and drug and gene delivery.

The present invention is based on the introduction of chemical bonds to crosslink the peptide fibers, resulting in gels with increased stiffness, elasticity and resistance to degradation. According to the present invention chemical crosslinks are introduced by the modification of the peptide sequence with a cysteine residue at the C-terminus, e.g., LIVAGKC (or $LK_6C$). This way, the pure amino acid composition of the gel is still conserved, which makes it, in general, a biocompatible material. Three-dimensional gels have been casted using these cross-linkable peptides in water or cell culture medium, such as growth medium completed with FBS/Penicillin/Streptomycin, and cargoes have been encapsulated within the matrix. Crucially, on top of physical self assembly forces, inter- and intra-fiber chemical bonds (in particular, disulfide bonds between cysteine or homocysteine residues which each has a thiol group) are now introduced. These chemical bonds can be encouraged in the presence of an oxidising agent like hydrogen peroxide ($H_2O_2$). Alternatively, chemical bond (e.g. disulfide) formation can also be encouraged in the oxidative blood environment when used in vivo. The formation of crosslinks significantly increases the elasticity of the gel due to the presence of additional chemical bonds. Another advantage of introducing crosslinks includes the increased resistance of the gel to degradation due to stronger interactions within and between fibers. This also means that less material is needed to obtain gels with mechanical properties comparable or even superior to earlier formulations, which in turn translates into significant cost savings and higher water contents. The present invention also allows the tuning of the physical properties of the hydrogels (stiffness, elasticity etc.) by modifying the oxidation cross-linking regime. The presence of reactive chemical groups also enables the functionalization of the gel with cargos or adhesive signals (e.g., CRGD) that further increase the biocompatibility of the gel. Therefore, cargos can now be covalently attached to the gel matrix besides simple physical encapsulation. The conjugation procedure can furthermore be conveniently done in situ, while the gel is being formed. According to the present invention, only mild conditions for the hydrogen peroxide-assisted oxidation process are used. Importantly, the use of horseradishperoxidase (HRP) prescribed in many other oxidation protocols can be avoided. This further reduces cost and facilitates regulatory approval in the future. Moreover, the inventors have devised a method to remove most of the unreacted hydrogen peroxide (>99%) and residual acid from solid-phase peptide synthesis before the introduction of e.g. cells onto the gels. The release profile of cargoes encapsulated within the gel can also be tuned by modifying the oxidation strategy.

The hydrogels according to the present invention are non-allergenic and non-toxic. The inventors also showed the biocompatibility of the hydrogels by successfully culturing several cell types on purified and crosslinked $LK_6C$–CRGD gels. They also managed to show the 3D distribution of cells within $LK_6C$–CRGD hydrogels. More particularly, cells were seeded on the gel and stained with the fluorescent live cell marker calcein. By obtaining a vertical cross sectional slice of the hydrogel and directly imaging the penetration depth profile of the cells, they observed multi-layered cell growth. This confirmed the infiltration of cells into the gel and convincingly demonstrated the 3D cell growth environment.

Potential applications of the hydrogels according to the present invention include:
- (Injectable) application for tissue engineering, particularly in orthopaedic and aesthetic surgery applications. $H_2O_2$ may even be avoided altogether as the overall redox potential of the blood is oxidative (while the intracellular overall redox potential is reductive). Thus, disulfide bonds will be naturally formed and in the process and, thus, increase the long-term stability of gel, which is already an improvement over current formulations.
- 3D cell culture substrate. Adhesion or growth signals can be covalently attached to increase biocompatibility. Such 3D cell culture substrate may, for example, be used as 3D cancer model.
- Skin Grafting. Using e.g. an $LK_6C$-based hydrogel as a scaffold, first fibroblasts are embedded within the bulk of the gel, followed by seeding of keratinocytes onto the surface of the gel to mimic the dermis and epidermis, respectively, of the human skin. This artificial skin layer can then be explored for grafting applications.
- Scaffold for corneal endothelial transplantation. The endothelium of a human cornea is a monolayer and is critical to the maintenance of vision. Handling of the endothelium is therefore technically challenging and can influence the success of a corneal endothelial transplant. Hydrogels according to the present invention, such as those based on $LK_6C$, could be used as a matrix support, on which corneal endothelial cells are cultured, and which can then be used as an endothelium replacement for transplants.
- Cargo delivery. Drugs and nanoparticles, e.g., EI/DNA complexes can be encapsulated for gradual release. Physical concentration of cargo in the vicinity of cells. Less cargo may be needed to achieve similar effects (compared to dilution of particles by dripping directly into growth medium), reducing on cost and toxicity.
- Surface adhesion of cargoes, e.g., DNA solution can first be layered on top of gel. Electrostatic interactions can hold DNA on surface of gel before DNA solution removed and cells cultured over gel. In this case, localised transfection is achieved.
- Attachment of particles, e.g., gold particles for application in sensing or other biodevices.
- Wound treatment. Advantages of using hydro gels according to the present invention for the treatment of wounds include: the hydrogel keeps the wound moist; it provides a scaffold for the regenerating skin layers; therapeutics can be loaded into the gel to aid recovery.

Disclosed herein is a novel class of hydrogels comprising hydrogel-forming peptides/peptoids derived from inter alia natural amino acids. These peptides/peptoids are small amphiphilic peptides with a hydrophobic portion of aliphatic amino acids and, preferably, one or two polar amino acids. The peptides/peptoids (typically 3-7-mers) are typically in the L- or D-form and can self assemble into supramolecular fibers which are organized into mesh-like structures. The hydrogels are generally characterized by a remarkable rigidity and are biocompatible and non-toxic. Depending on the peptide/peptoid sequence these hydrogels can show thermoresponsive or thixotropic character. By selecting the peptide assembling conditions the thickness and length of the fibers can be controlled. The rigid hydro gels can be used for cultivation of a variety of primary human cells, providing peptide scaffolds that can be useful in the repair and replacement of various tissues. Also disclosed is the procedure of preparing these hydrogels. Disclosed is further the use of respective hydro gels in applications such as cell culture, tissue engineering, plastic surgery, drug delivery, oral applications, cosmetics, packaging and the like as well as for technical applications, as for example for use in electronic devices which may include solar or fuel cells.

Also disclosed herein is an amphiphilic peptide and/or peptoid capable of forming a hydrogel, i.e. a polymer network in which water is the dispersion medium. The amphiphilic peptide and/or peptoid includes one or more linear amphiphilic sequences, each having a polar and anon-polar portion. For sake of simplicity explanations are in the following to a large extent focused on amphiphilic peptides and/or peptoids that consist of a single respective linear sequence. In these explanations a respective peptide and/or peptoid is denominated a "linear peptide and/or peptoid". Respective explanations apply to any linear sequence, which may also be included in an amphiphilic peptide and/or peptoid with a plurality of these linear sequences. Each of these linear sequences is individually selected. In some embodiments an amphiphilic peptide and/or peptoid disclosed herein includes several linear amphiphilic sequences, each of them differing from any other of the linear amphiphilic sequences. In some embodiments an amphiphilic peptide and/or peptoid disclosed herein includes several identical linear amphiphilic sequences. In one embodiment an amphiphilic peptide and/or peptoid disclosed herein includes a plurality of linear amphiphilic sequences, each linear amphiphilic sequence being identical to each other linear amphiphilic sequence.

Also disclosed is a peptide and/or peptoid that includes o amphiphilic linear sequences. The symbol o represents an integer selected in the range from 1 to about 25, such as from 1 to about 20, from 1 to about 18, from 1 to about 15, from 1 to about 12, from 1 to about 10, from 1 to about 8, from 1 to about 6, from 1 to about 5 from 1 to about 4 or from 1 to about 3.

In some embodiments these amphiphilic linear sequences are linked in a consecutive manner, thereby defining a linear portion of the peptide and/or peptoid.

In some embodiments the peptide and/or peptoid has a backbone with one or more branches. In such an embodiment these amphiphilic linear sequences may be included on different branches. As mentioned above, each of the o amphiphilic linear sequences is independently selected. A respective amphiphilic linear sequence has a length of n aliphatic amino acids. The symbol n represents an integer selected in the range from 3 to about 18, such as from 3 to about 15, from 3 to about 14, from 3 to about 13, from 3 to about 12, from 3 to about 11, from 3 to about 10, from 3 to about 9, from 3 to about 8 or from 3 to about 7, such as 3, 4, 5, 6, 7, 8, 9 or 10 aliphatic amino acids.

In some embodiments an amphiphilic linear sequence of a peptide and/or peptoid described herein is chiral, rendering the entire amphiphilic peptide and/or peptoid chiral. A corresponding linear peptide and/or peptoid, i.e. an embodiment that consists of a single respective linear sequence, is accordingly a chiral peptide or peptoid. A respective amphiphilic linear sequence may include any linear non-aromatic amino acid. The term "amino acid" as used herein refers to an alpha-amino carboxylic acid, i.e. a carboxylic acid with an amino group in the α-position. The respective amino group may be an —$NH_2$ group or an —$NHR^1$ group. The moiety $R^1$ may be any aliphatic group, whether alkyl, alkenyl or alkynyl, with a main chain that includes 1 to 5, to 10, to 15 or to 20 carbon atoms. Examples of alkenyl radicals are straight chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, preferably such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3, dimethylbutyl.

A peptoid is an oligo(N-alkyl) glycine that, similar to the side chain connected to the a carbon atom (see below) of a peptide, at the amide nitrogen carries a moiety that is an aliphatic moiety. Accordingly, in embodiments where an —$NHR^1$ group (supra) is included in the amino acid and the a carbon atom is included in a —$CH_2$— group, the reaction product of coupling a plurality of such amino acids may be called a peptoid. A peptoid can also be taken to differ from a peptide in that it carries its side chain at the amide nitrogen rather than at the a carbon atom. Peptoids are typically resistant to proteases and other modifying enzymes and can have a much higher cell permeability than peptides (see e.g. Kwon, Y.-U., and Kodadek, T., J. Am. Chem. Soc. (2007) 129, 1508-1509).

The term "amino acid" includes compounds in which the carboxylic acid group is shielded by a protecting group in the form of an ester (including an ortho ester), a silyl ester, an amide, a hydrazide, an oxazole, an 1,3-oxazoline or a 5-oxo-1,3, oxazolidine. The term "amino acid" also includes compounds in which an amino group of the form —$NH^2$ or —$NHR^1$ (supra) is shielded by a protecting group. Suitable amino protecting groups include, but are not limited to, a carbamate, an amide, a sulfonamide, an imine, an imide, a histidine, a N-2,5,-dimethylpyrrole, an N-1,1,4,4-tetramethyldisilylazacyclopentane adduct, an N-1,1,3,3-tetramethyl-1,-disilisoindoline, an N-diphenylsilyldiethylene, an 1,3,5-dioxazine, a N-[2-(trimethyl silyl)ethoxy]methylamine, a N-(5,5-dimethyl-3-oxo-1-cyclohexenyl)amine, a N-4,4,4-trifluoro-3-oxo-1-butenylamine, a N-9-borabicyclononane and a nitroamine. A protecting group may also be present that shields both the amino and the carboxylic group such as e.g. in the form of a 2,2-dimethyl-4-alkyl-2-sila-5-oxo-1,3-oxazolidine. The alpha carbon atom of the amino acid typically further carries a hydrogen atom. The so called "side chain" attached to the alpha carbon atom, which is in fact the continuing main chain of the carboxylic acid, is an aliphatic moiety that may be linear or branched. The term "side chain" refers to the presence of the amino acid in a peptide (supra), where a backbone is formed by coupling a plurality of amino acids. An aliphatic moiety bonded to the a carbon atom of an amino acid included in such a peptide then defines a side chain relative to the backbone. As explained above, the same applies to an aliphatic moiety bonded to the amino group of the amino acid, which likewise defines a side chain relative to the backbone of a peptoid.

The term "aliphatic" means, unless otherwise stated, a straight or branched hydrocarbon chain, which may be saturated or mono- or poly-unsaturated and include heteroatoms. The term "heteroatom" as used herein means an atom of any element other than carbon or hydrogen. An unsaturated aliphatic group contains one or more double and/or triple bonds (alkenyl or alkynyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main)chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, preferably such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3, dimethylbutyl. Both the main chain as well as the branches may furthermore contain heteroatoms as for instance N, 0, S, Se or Si or carbon atoms may be replaced by these heteroatoms.

An aliphatic moiety may be substituted or unsubstituted with one or more functional groups. Substituents may be any functional group, as for example, but not limited to, amino, amido, azido, carbonyl, carboxyl, keto, cyano, isocyano, dithiane, halogen, hydroxyl, nitro, organametal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methanesulfonyl. As should be apparent from the above, the side chain of an amino acid in a peptide/peptoid described herein may be of a length of 0 to about 5, to about 10, to about 15 or to about 20 carbon atoms. It may be branched and include unsaturated carbon-carbon bonds. In some embodiments one or more natural amino acids are included in the peptide or peptoid. Such a natural amino acid may be one of the 20 building blocks of naturally occurring proteins.

In a peptide or peptoid, including a peptide/peptoid disclosed herein individual amino acids are covalently coupled via amide bonds between a carboxylic group of a first and an amino group of a second amino acid. A peptide and/or peptoid disclosed herein is non-repetitive, such that two amino acids coupled to each other are always different from one another.

The term amphiphilic refers to a compound that is soluble in both polar and non-polar fluids. It also encompasses multiphase compounds. The amphiphilic properties of the peptide and/or peptoid are due to the presence of both polar and non-polar moieties within the same peptide and/or peptoid. In this regard the peptide and/or peptoid may be of surfactant nature. Accordingly, the polar properties of a peptide and/or peptoid disclosed herein are based on a polar moiety. Two such moiety are a —COOH side group, in particular in the form of a charged COO— group and an amino group. A further such moiety is a C-terminal —COOH group if it is present in free, unprotected form. Generally, a surfactant molecule includes a polar, typically hydrophilic, head group attached to a non-polar, typically hydrocarbon, moiety. Non-polar moieties of a peptide or peptoid include a hydrocarbon chain that does not carry a functional group.

An amphiphilic linear sequence included in a peptide and/or peptoid disclosed herein thus includes a polar moiety and a non-polar moiety. The polar moiety includes an aliphatic amino acid that carries a polar group such as a hydroxyl group, a thiol group, a seleno group, an amino group, an amide group, an ether group, a thioether group or a seleno ether group. Accordingly, the polar moiety may include an amino acid that carries a functional polar group with a proton such as hydroxyl, thiol, selenol, amine or amide. The polar moiety may also include the C-terminus or the N-terminus of the peptide and/or peptoid. The C-terminus or the N-terminus may in such a case be present in the form of the free carboxyl or amino group, respectively, i.e. free of a protecting group.

Generally the polar moiety of a linear amphiphilic sequence of an amphiphilic peptide and/or peptoid disclosed herein is defined by a single amino acid, by two consecutive amino acids or by three consecutive amino acids that is/are coupled to the non-polar moiety of the peptide/peptoid. Accordingly, in some embodiments the polar moiety of the peptide/peptoid consists of two amino acids that are covalently coupled via an amide bond, both amino acids carrying a polar peptide/peptoid side chain. One of these two amino acids may be a terminal amino aid of the peptide/peptoid, defining its N- or C-terminus. In some embodiments the amphiphilic peptide/peptoid has a single amino acid with a polar side chain with the residual portion of the peptide/peptoid defining the non-polar moiety. In some embodiments the amphiphilic peptide/peptoid has two amino acids with a polar side chain while the residual portion of the peptide/peptoid defines the non-polar moiety. As three illustrative examples of a respective polar side chain may serve 4-methyl-4-thio-pentyl, 6-ethoxycarbonyl-4,5-dimethyl-hexyl and 6-hydroxy-4-(1-hydroxyethyl)-hexyl groups. As used herein, the numbering of corresponding peptide/peptoid side chains is started with "1" at the carbon atom that is covalently bonded to the a-carbon atom of the amino acid or to the amino group of the amino acid, respectively. Amino acids included in the polar moiety may be or include, but are not limited to, aspartic acid, asparagine, glutamic acid, 4-fluoro-glutamic acid, 2-aminoadipic acid, γ-carboxy-glutamic acid, 4-tert-butyl aspartic acid, glutamine, 5-N-ethyl-glutamine (theanine), itrulline, thio-citrulline, cysteine, homocysteine, methionine, ethionine, selenomethionine, telluromethionine, threonine, allo-threonine, serine, homoserine, arginine, homoarginine, ornithine, lysine, 5-hydroxy-lysine and N(6)-carboxymethyllysine. Any such amino acid maybe present in the L- or D-form.

The amphiphilic linear sequence of the amphiphilic peptide/peptoid disclosed herein can be defined as having n amino acids. Where a single amino acid with a polar side chain is included in the amphiphilic linear sequence, the non-polar moiety may then be taken to have n−1 amino acids. In this case the polar moiety consists of exactly one amino acid, such amino acid being selected from any amino acids of the foregoing paragraph. Where two consecutive amino acids with a polar side chain are included in the amphiphilic linear sequence of the peptide/peptoid, the non-polar moiety may then be taken to have n−2 amino acids. In this case the polar moiety consists of exactly two amino acids. Where three consecutive amino acids with a polar side chain are included in the amphiphilic linear sequence, the non-polar moiety may then be taken to have n−3 amino acids. In this case the polar moiety consists of exactly three amino acids. In embodiments where the polar moiety consists of two amino acids, the polar moiety may have a sequence selected from Asn-Asn, Asp-Asp, Glu-Glu, Gln-Gln, Asn-Gln, Gln-Asn, Asp-Gin, Gin-Asp, Asn-Glu, Glu-Asn, Asp-Glu, Glu-Asp, Gln-Glu, Glu-Gln, Asp-Asn, Asn-Asp, Thr-Thr, Ser-Ser, Thr-Ser, Ser-Thr, Asp-Ser, Ser-Asp, Ser-Asn, Asn-Ser, Gln-Ser, Ser-Gln, Glu-Ser, Ser-Glu, Asp-Thr, Thr-Asp, Thr-Asn, Asn-Thr, Gin-Thr, Thr-Gln, Glu-Thr, hr-Glu. In embodiments where the polar moiety consists of three amino acids, the polar moiety may have a sequence selected from Asn-Asn-Asn, Asn-Asn-Asp, Asn-Asp-Asn, Asp-Asn-Asn, Asp-Asp-Asn, Asp-Asn-Asp, Asp-Asp-Asp, Asn-Asn-Glu, Asn-Asn-Gln, Asn-Glu-Asn, Asn-Gln-Asn, Glu-Glu-Glu, Gln-Gln-Gln, Asn-Gln-Gln, Asn-Glu-Gln, Asp-Asn-Glu, Gln-Asn-Asn, Gln-Asn-Asn, Glu-Asp-Gln, Asp-Gin-Asp, Asn-Glu-Asp, Glu-Asn-Gln, Asp-Glu-Gln, Asn-Glu-Gln, Glu-Asp-Asn, and Gln-Asp-Asn, Thr-Thr-Thr, Ser-Ser-Ser, Asn-Thr-Thr, Asn-Ser-Ser Asn-Ser-Thr, Asn-Thr-Ser Asp-Asn-Ser, Ser-Asn-Asn, Thr-Asn-Asn, Ser-Asp-Thr, to name a few.

The amphiphilic linear sequence of the peptide/peptoid has a net charge at physiological pH. The term "physiological pH" is known to those in the art to refer to the pH value of blood, which has typically a pH value of about 7.4. In embodiments where the amphiphilic linear sequence is arranged at the C- or N-terminus of the peptide/peptoid, the respective terminus may provide the corresponding net charge. In embodiments where the amphiphilic linear sequence is not arranged at the C- or N-terminus of the peptide/peptoid, the polar moiety of the amphiphilic linear sequence includes one or more amino acids that have a side chain with a functional group that is charged at physiological pH. Illustrative examples of a respective functional group include an amino, a nitro-, a guanidino, a esteryl, a sulfonyl or a carboxyl group. In some embodiments the net charge of the amphiphilic linear sequence is, as a positive or as a negative charge, equal to or smaller than the number of amino acids included in the polar moiety thereof. In some embodiments the net charge of the amphiphilic linear sequence is one of −3, −2 or −1. In some embodiments the net charge of the amphiphilic linear sequence is +1, +2 or +3.

The respective polar side chain of an amino acid of the polar moiety, coupled to the a-carbon atom of the amino acid (supra) and/or to the amino group thereof, may typically be defined by a main chain that includes 1 to about 20, including 1 to about 15, 1 to about 10 or 1 to about 5 carbon atoms. For sake of clarity it is recited that the term "side chain" is used relative to the backbone of the peptide and/or peptoid. This peptide and/or peptoid side chain may be branched and thus be defined by a main chain and branches. Both the main chain and branches, f present, of the peptide and/or peptoid side chain may include one or more double or triple bonds (supra). Examples of side chains include, but are not limited to, methyl, ethyl, propyl, isopropyl, propenyl, propinyl, butyl, butenyl, sec-butyl, tert-butyl, isobutyl, pentyl, neopentyl, sopentyl, pentenyl, hexyl, 3,3 dimethylbutyl, heptyl, octyl, nonyl or decyl groups. The functional polar group is bonded to this the peptide and/or peptoid side chain. In some embodiments the polar moiety of the amphiphilic linear sequence includes two identical amino acids. Where these amino acids are naturally occurring amino acids, they may for example define one of the sequences Lys-Lys, Gln-Gln, Glu-Glu, Asp-Asp, Asn-Asn, Met-Met, Thr-Thr, Arg-Arg or Ser-Ser. The term "naturally occurring" in this context refers to the 20 amino acids into which the genetic code is directly being translated by any organism. Such two identical polar amino acids may for example be adjacent to the non-polar moiety. In some embodiments the amphiphilic linear sequence of the peptide/peptoid has a hydrophobic tail of aliphatic amino acids and at least one polar, including a charged, amino acid head group. The non-polar moiety includes an amino acid, generally at least two amino acids, with a hydrocarbon chain that does not carry a functional group. The respective side chain, coupled to the a-carbon atom of the amino acid (supra), may have a main chain that includes 0 to about 20 or 1 to about 20, including 0 to about 15, 1 to about 15, 0 to about 10, 1 to about 10, 1 to about 5 or 0 to about 5 carbon atoms.

The non-polar moiety may thus include an amino acid without side chain, i.e. glycine. The peptide and/or peptoid side chain may be branched (supra) and include one or more double or triple bonds (supra). Examples of peptide and/or peptoid side chains include, but are not limited to, methyl, ethyl, propyl, isopropyl, propenyl, ropinyl, butyl, butenyl, sec-butyl, tert-butyl, isobutyl, pentyl, neopentyl, isopentyl, pentenyl, exyl, 3,3 dimethylbutyl, heptyl, octyl, nonyl or decyl groups. As a few illustrative examples, the non-polar moiety may include an amino acid of alanine, valine, leucine, isoleucine, norleucine, norvaline, 2-(methylamino)-isobutyric acid, 2-amino-5-hexynoic acid. Such an amino acid may be present in any desired configuration. Bonded to the non-polar moiety may also be the C-terminus or the N-terminus of the peptide/peptoid. Typically the C-terminus or the N-terminus is in such a case shielded by a protecting group (supra).

In some embodiments the non-polar moiety includes a sequence of amino acids that is arranged in decreasing or increasing size. Hence, a portion of the amino acids of the non-polar moiety may be arranged in a general sequence of decreasing or increasing size. Relative to the direction from N- to C-terminus or from C- to N-terminus this general sequence can thus be taken to be of decreasing size. By the term "general sequence" of decreasing or increasing size is meant that embodiments are included in which adjacent amino acids are of about the same size as long as there is a general decrease or increase in size. Within a general sequence of decreasing size the size of adjacent amino acids of the non-polar moiety is accordingly identical or smaller in the direction of the general sequence of decreasing size. In some embodiments the general sequence of decreasing or increasing size is a non-repetitive sequence. As an illustrative example, where a respective portion of amino acids is a sequence of five amino acids, the first amino acid may have a 3,-dimethyl-hexyl side chain. The second amino acid may have a neopentyl side chain. The third amino acid may have a pentyl side chain. The fourth amino acid may have a butyl side chain. The fifth amino acid may be glycine, i.e. have no side chain. Although a neopently and a pentyl side chain are of the same size, the general sequence of such a non-polar peptide portion is decreasing in size. As a further illustrative example of a general sequence of decreasing size in a non-polar moiety the respective non-polar portion may be a sequence of three amino acids. The first amino acid may have an n-nonyl side chain. The second amino acid may have a 3-ethyl-2-methyl-pentyl side chain. The third amino acid may have a tert-butyl side chain. As yet a further illustrative example of a general sequence of decreasing size in a non-polar moiety, the non-polar moiety may be a sequence of nine amino acids. The first amino acid may have a 4-propyl-nonyl side chain. The second amino acid may have an n-dodecyl side chain. The third amino acid may have a 6,6-diethyl-3-octenyl side chain. An n-dodecyl side chain and a 6,6-diethyl-3-octenyl sidechain both have 12 carbon atoms and thus again have a comparable size, Nevertheless, the 6,6-diethyl-3-octenyl group includes an unsaturated carbon-carbon bond and is thus of slightly smaller size than the dodecyl group. The fourth amino acid may have a 2-methyl-nonyl sidechain. The fifth amino acid may have a 3-propyl-hexyl side chain. The sixth amino acid may have an n-hexyl side chain. The seventh amino acid may have a 2-butynyl side chain. The 8th amino acid may have an isopropyl side chain. The ninth amino acid may have a methyl sidechain.

Where a portion of the amino acids of the non-polar moiety arranged in a general sequence of decreasing (or increasing) size only contains naturally occurring amino acids (whether in the D- or the L-form), it may for example have a length of five amino acids, such as the sequence leucine-isoleucine-valine-alanine-glycine or isoleucine-leucine-valine-alanine-glycine, A general sequence of decreasing size of only natural amino acids may also have a length of four amino acids. Illustrative examples include the sequences isoleucine-leucine-valine-alanine, leucine-isoleucine-valine-alanine, isoleucine-valine-alanine-glycine, leucine-valine-alanine-glycine, eucine-isoleucine-alanine-glycine, leucine-isoleucine-valine-glycine, isoleucine-leucine-alanine-glycine or isoleucine-leucine-valine-glycine. A general sequence of decreasing size of only natural amino acids may also have a length of three amino acids. Illustrative examples include the sequences isoleucine-valine-alanine, leucine-valine-alanine, isoleucine-valine-glycine, leucine-valine-glycine, leucine-alanine-glycine, isoleucine-alanine-glycine or isoleucine-leucine-alanine. A general sequence of decreasing size of only natural amino acids may also have a length of two amino acids. Illustrative examples include the sequences isoleucine-valine, leucine-valine, isoleucine-alanine, leucine-alanine, leucine-glycine, isoleucine-glycine, valine-alanine, valine-glycine or alanine-glycine.

In some embodiments the direction of decreasing size of the above defined general sequence of decreasing size is the direction toward the polar moiety of the amphiphilic linear sequence. Accordingly, in such embodiments the size of adjacent amino acids within this portion of the non-polar moiety is accordingly identical or smaller in the direction of the polar moiety. Hence, as a general trend in such an embodiment, the closer to the polar moiety of the amphiphilic linear sequence, the smaller is the overall size of a peptide and/or peptoid side chain throughout the respective general sequence of decreasing size. In the above illustrative example of a general sequence of three amino acids with a n-nonyl, a 3-ethyl-2-methyl-pentyl and a tert-butyl side chain, the next amino acid may be polar in that it carries a peptide/peptoid sidechain with a polar functional group. As an illustrative example, adjacent to the tert-butyl sidechain within the peptide/peptoid there may be a 3-carboxy-n-butyl side chain.

In some embodiments the entire non-polar moiety of the amphiphilic linear peptide and/or peptoid or the amphiphilic linear sequence, respectively, consists of the general sequence of decreasing (or increasing) size. In such an embodiment the general sequence of decreasing (or increasing) size may have a length of n–m amino acids (cf. above). In some embodiments the general sequence of decreasing or increasing size is flanked by further non-polar side chains of the peptide/peptoid. In one embodiment the general sequence of decreasing (or increasing) size has a length of n–m–1 amino acids. In this embodiment there is one further amino acid included in the peptide/peptoid, providing a non-polar peptide/peptoid side chain. This amino acid may be positioned between the general sequence of decreasing (or increasing) size and the polar amino acid, the polar amino acid may be positioned between this additional non-polar amino acid and the general sequence of decreasing (or increasing) size or the general sequence of decreasing (or increasing) size may be positioned between the polar amino acid and this additional non-polar amino acid. Typically the general sequence of decreasing (or increasing) size is positioned between the polar amino acid and this additional non-polar amino acid. The additional non-polar amino acid may for example define the N-terminus of the peptide/peptoid, which may be shielded by a protecting group such as an amide, e.g. a propionic acyl or an acetyl group. Together with the general sequence of decreasing (or increasing) size as defined above it may define the non-polar portion of the peptide/peptoid. The polar amino acid may define the C-terminus of the peptide/peptoid. In this example the general sequence of decreasing (or increasing) size is thus flanked by the polar amino acid on one side and by the additional non-polar amino acid on the other side. In one embodiment where embodiment the general sequence of decreasing (or increasing) size has a length of n–m–1 amino acids, the remaining non-polar amino acid of the non-polar moiety of n–m amino acids is one of alanine and glycine.

As explained above, the polar moiety of the amphiphilic linear sequence may in some embodiments be defined by two or three consecutive amino acids. The polar moiety includes m aliphatic amino acids. Each of the m aliphatic amino acids is independently selected and carries an independently selected polar group. The symbol m represents an integer selected from 1, 2 and 3. The at least essentially non-polar moiety (supra) accordingly has a number of n–m, i.e. n–1, n–2 or n–3 amino acids. In some embodiments n is equal to or larger than m+2. In such an embodiment m may thus represent a number of n–2 or smaller.

In an embodiment where the entire non-polar moiety of the amphiphilic linear peptide and/or peptoid consists of the general sequence of decreasing (or increasing) size (supra), this non polar moiety may thus have a length of n–2 or n–3 amino acids. In an embodiment where the amphiphilic linear peptide and/or peptoid has a further non-polar side chain in addition to the non-polar moiety of decreasing (or increasing) size, this additional non-polar side chain maybe included in an amino acid that is directly bonded to an amino acid of the general sequence of decreasing (or increasing) size. The non-polar moiety may thus be defined by the non-polar moiety of decreasing (or increasing) size and the respective further amino acid with a non-polar side chain. In one such an embodiment where m=1, the non-polar moiety may thus have a length of n–2 amino acids, of which the non-polar moiety of decreasing (or increasing) size has a length of n–3 amino acids. The general sequence of decreasing (or increasing) size may be positioned between the two polar amino acids and this additional non-polar amino acid, or the additional non-polar amino acid may be positioned between the general sequence of decreasing (or increasing) size and the two polar amino acids. Typically the general sequence of decreasing (or increasing) size is positioned between the two polar amino acids and this additional non-polar amino acid. As mentioned above, one of the two polar amino acids may define the C-terminus of the peptide/peptoid. In this example the general sequence of decreasing (or increasing) size may thus be flanked by the two consecutive polar amino acids on one side and by the additional non-polar amino acid on the other side. Again, in some embodiments where m=1 the two consecutive polar amino acids may also be positioned between the general sequence of decreasing (or increasing) size and the additional non-polar amino acid, in which case the non-polar moiety has a first portion with a length of n–3 amino acids and a further portion of one amino acid.

Electrostatic forces, hydrogen bonding and van der Waals forces between amphiphilic linear sequences as defined above, including amphiphilic linear peptides and/or peptoids, result in these amphiphilic linear sequences to be coupled to each other. Without being bound by theory, hereby a cross-linking effect occurs that allows the formation of a hydrogel. In this regard the inventors have observed the formation of fibers based on helical structures.

The fibers formed of amphiphilic linear sequences of amphiphilic peptides and/or peptoids disclosed herein typically show high mechanical strength, which renders them particularly useful in tissue regeneration applications, for instance the replacement of damaged tissue. Amphiphilic peptides and/or peptoids disclosed herein have been observed to generally assemble into a fiber structure that resembles collagen fibers. Collagen, a component of soft tissue in the animal and human body, is a fibrous protein that provides most of the tensile strength of tissue. The mechanical strength of fibers of amphiphilic peptides and/or peptoids disclosed herein has been found to typically be much higher than that of collagen (cf. e.g. Figures) of gelatine, the hydrolysed form of collagen. An amphiphilic peptide and/or peptoid disclosed herein may thus be included in a hydrogel that is used as permanent or temporary prosthetic replacement for damaged or diseased tissue.

The amphiphilic linear sequence of the peptide/peptoid, which may represent the entire amphiphilic peptide/peptoid (supra) has been found to show remarkable stability at physiological conditions, even at elevated temperatures. It is in some embodiments stable in aqueous solution at physiological conditions at ambient temperature for a period of time in the range from 1 day to 1 month or more. It may in some embodiments be stable in aqueous solution at physiological conditions at 90° C. for at least 1 hour, at least 2 hours, at least 3 hours, at least 4 hours or at least 5 hours.

An amphiphilic linear sequence of an amphiphilic peptide and/or peptoid disclosed herein, including an amphiphilic linear peptide and/or peptoid, is capable of providing a self assembling a-helical fiber in aqueous solution under physiological conditions. The peptides/peptoids (typically 3-7-mers) in the L- or D-form can self assemble into supramolecular helical fibers which are organized into mesh-like structures mimicking biological substances such as collagen. It has previously been observed in X-ray crystallography that peptides of a length of 3 to 6 amino acids with repetitive alanine containing sequences and an acetylated C-terminus take a helical conformation (Hatakeyama, Y, et al, Angew. Chem. Int. Ed. (2009) 8695-8698). Using peptides with an amphiphilic sequence disclosed herein, Ac-LD$_6$ (L), the formation of aggregates has for example been observed already at 0.1 mg/ml. As the concentration of peptide is increased to 1 mg/ml, the peptide monomers were found to align to form fibrous structures. With a formation of fibers occurring under physiological conditions at concentrations below 2 mM a peptide/peptoid disclosed herein is well suited as an injectable hydrogel material that can form a hydrogel under physiological conditions. Also disclosed herein is an amphiphilic linear peptide and/or peptoid as defined above for tissue engineering as well as to a tissue engineering method that involves applying, including injecting a respective amphiphilic linear peptide and/or peptoid.

A hydrogel as disclosed herein is typically characterized by a remarkable rigidity and are generally biocompatible and non-toxic. Depending on the selected peptide/peptoid sequence these hydrogels can show thermoresponsive or thixotropic character. Reliant on the peptide/peptoid assembling conditions the fibers differ in thickness and length. Generally rigid hydro gels are obtained that are well suited for cultivation of a variety of primary human cells, providing peptide/peptoid scaffolds that can be useful in the repair and replacement of various tissues. Disclosed is also a process of preparing these hydrogels. The exemplary usage of these hydrogels in applications such as cell culture, tissue engineering, plastic surgery, drug delivery, oral applications, cosmetics, packaging and the like is described, as well as for technical applications, as for example for use in electronic devices which might include solar or fuel cells.

As an amphiphilic linear sequence of the peptide/peptoid, a hydrogel as disclosed herein shows high stability at physiological conditions, even at elevated temperatures. In some embodiments such a hydrogel is stable in aqueous solution at ambient temperature for a period of at least 7 days, at least 14 days, at least a month or more, such as at least 1 to about 6 months.

In some embodiments a hydrogel disclosed herein is coupled to a molecule or a particle, including a quantum dot, with characteristic spectral or fluorometric properties, such as a marker, including a fluorescent dye. A respective molecule may for instance allow monitoring the fate, position and/or the integrity of the hydrogel.

In some embodiments a hydrogel disclosed herein is coupled to a molecule with binding affinity for a selected target molecule, such as a microorganism, a virus particle, a peptide, a peptoid, a protein, a nucleic acid, a peptide, an oligosaccharide, a polysaccharide, an inorganic molecule, a synthetic polymer, a small organic molecule or a drug.

The term "nucleic acid molecule" as used herein refers to any nucleic acid in any possible configuration, such as single stranded, double stranded or a combination thereof. Nucleic acids include for instance DNA molecules (e.g., DNA or genomic DNA), RNA molecules (e.g., RNA), analogues of the DNA or RNA generated using nucleotide analogues or using nucleic acid chemistry, locked nucleic acid molecules (LNA), and protein nucleic acids molecules (PNA). DNA or RNA may be of genomic or synthetic origin and may be single or double stranded. In the present method of an embodiment of the invention typically, but not necessarily, an RNA or a DNA molecule will be used. Such nucleic acid can be e.g. mRNA, cRNA, synthetic RNA, genomic DNA, eDNA synthetic DNA, a copolymer of DNA and RNA, oligonucleotides, etc. A respective nucleic acid may furthermore contain non-natural nucleotide analogues and/or be linked to an affinity tag or a label. In some embodiments the nucleic acid molecule may be isolated, enriched, or purified. The nucleic acid molecule may for instance be isolated from a natural source by eDNA cloning or by subtractive hybridization. The natural source may be mammalian, such as human, blood, semen, or tissue. The nucleic acid may also be synthesized, e.g. by the triester method or by using an automated DNA synthesizer.

Many nucleotide analogues are known and can be used in nucleic acids and oligonucleotides used in the methods of exemplary embodiments of the invention. A nucleotide analogue is a nucleotide containing a modification at for instance the base, sugar, or phosphate moieties. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases. Other nucleotide analogues serve as universal bases. Universal bases include 3-nitropyrrole and 5-nitroindole. Universal bases are able to form a base pair with any other base. Base modifications often can be combined with for example a sugar modification, such as for instance 2'-O-methoxyethyl, .g. to achieve unique properties such as increased duplex stability.

A peptide may be of synthetic origin or isolated from a natural source by methods well known in the art. The natural source may be mammalian, such as human, blood, semen, or tissue. A peptide, including a polypeptide may for instance be synthesized using an automated polypeptide synthesizer. Illustrative examples of polypeptides are an antibody, a fragment thereof and a proteinaceous binding molecule with antibody-like functions. Examples of (recombinant)antibody fragments are Fab fragments, Fv fragments, single-chain Fv fragments (scFv), diabodies, triabodies (Iliades, P., et al., FEBS Lett (1997) 409, 437-441), decabodies (Stone, E., et al., Journal of Immunological Methods (2007) 318, 88-94) and other domain antibodies (Holt, L. J., et al., Trends Biotechnol. (2003), 21, 11, 484-490). An example of a proteinaceous binding molecule with antibody-like functions is a mutein based on a polypeptide of the lipocalin family (WO 03/029462, Beste et al., Proc. Natl. Acad. Sci. U.S.A. (1999)96, 1898-1903). Lipocalins, such as the bilin binding protein, the human neutrophil gelatinase-associated lipocalin, human Apolipoprotein D or glycodelin, posses natural ligand binding sites that can be modified so that they bind to selected small protein regions known as haptens. Examples of other proteinaceous binding molecules are the so-called glubodies (see e.g. international patent application WO 96/23879), proteins based on the ankyrin scaffold (Mosavi, L. K., et al., Protein Science (2004) 13, 6, 1435-1448) or crystalline scaffold (e.g. international patent application WO 01/04144) the proteins described in Skerra, J. Mol. Recognit. (2000) 13, 167-187, AdNectins, tetranectins and avimers. Avimers contain so called A-domains that occur as strings of multiple domains in several cell surface receptors (Silverman, J., et al., Nature Biotechnology (2005) 23, 1556-1561). Adnectins, derived from a domain of human fibronectin, contain three loops that can be engineered for immunoglobulin-like binding to targets (Gill, D. S. & Damle, N. K., Current Opinion in Biotechnology (2006) 17, 653-658). Tetranectins, derived from the respective human homotrimeric protein, likewise contain loop regions in a C-type lectin domain that can be engineered for desired binding (ibid.). Where desired, a modifying agent may be used that further increases the affinity of the respective moiety for any or a certain form, class etc. of target matter.

An example of a nucleic acid molecule with antibody-like functions is an aptamer. An aptamer folds into a defined three-dimensional motif and shows high affinity for a given target structure. Using standard techniques of the art such as solid-phase synthesis an aptamer with affinity to a certain target can accordingly be formed and immobilized on a hollow particle of an embodiment of the invention.

As a further illustrative example, a linking moiety such as an affinity tag may be used to immobilise the respective molecule. Such a linking moiety may be a molecule, e.g. a hydrocarbon-based (including polymeric) molecule that includes nitrogen-, phosphorus-, sulphur-, arben-, halogen- or pseudohalogen groups, or a portion thereof. As an illustrative example, the peptide/peptoid included in the hydrogel may include functional groups, for instance on aside chain of the peptide/peptoid, that allow for the covalent attachment of a biomolecule, for example a molecule such as a protein, a nucleic acid molecule, a polysaccharide or any combination thereof. A respective functional group may be provided in shielded form, protected by a protecting group that can be released under desired conditions. Examples of a respective functional group include, but are not limited to, an amino group, an aldehyde group, a thiol group, a carboxy group, an ester, an anhydride, a sulphonate, a sulphonate ester, an imidoester, a silyl halide, an epoxide, an aziridine, a phosphoramidite and a diazoalkane. Examples of an affinity tag include, but are not limited to, biotin, dinitrophenol or digoxigenin, ligohistidine, polyhistidine, an immunoglobulin domain, maltose-binding protein, glutathione-S-transferase (GST), calmodulin binding peptide (CBP), FLAG'-peptide, the T7 epitope (Ala-Ser-Met-Thr-Gly-Gly-Gln-Gln-Met-Gly), maltose binding protein (MBP), the HSV epitope of the sequence Gln-Pro-Glu-Leu-Ala-Pro-Glu-Asp-Pro-Glu-Asp of herpes simplex virus glycoprotein D, the hemagglutinin (HA) epitope of the sequence Tyr-Pro-Tyr-Asp-Val-Pro-Asp-Tyr-Ala, the "myc" epitope of the transcription factor c-myc of the sequence Glu-Gln-Lys-Leu-Ile-Ser-Glu-Glu-Asp-Leu, or an oligonucleotide tag. Such an oligonucleotide tag may for instance be used to hybridise to an immobilised oligonucleotide with a complementary sequence. A further example of a linking moiety is an antibody, a fragment thereof or a proteinaceous binding molecule with antibody-like functions (see also above). A further example of linking moiety is a cucurbituril or a moiety capable of forming a complex with a cucurbituril. A cucurbituril is a macrocyclic compound that includes glycoluril units, typically self-assembled from an acid catalyzed condensation reaction of glycoluril and formaldehyde. A cucurbit[n]uril, (CB[n]), that includes n glycoluril units, typically has two portals with polar ureido carbonyl groups. Via these ureido carbonyl groups cucurbiturils can bind ions and molecules of interest. As an illustrative example cucurbit[7]uril (CB[7]) can form a strong complex with ferrocenemethylammonium or adamantylammonium ions. Either the cucurbit[7]uril or e.g. ferrocenemethylammonium may be attached to a biomolecule, while the remaining binding partner (e.g. ferrocenemethylammonium or cucurbit[7]uril respectively) can be bound to a selected surface. Contacting the biomolecule with the surface will then lead to an immobilisation of the biomolecule. Functionalised CB[7] units bound to a gold surface via alkanethiolates have for instance been shown to cause an immobilisation of a protein carrying a ferrocenemethylammonium unit (Hwang, I., et al., J. Am. Chem. Soc. (2007) 129, 4170-4171).

Further examples of a linking moiety include, but are not limited to an oligosaccharide, anoligopeptide, biotin, dinitrophenol, digoxigenin and a metal chelator (cf. also below). As an illustrative example, a respective metal chelator, such as ethylenediamine, ethylenediaminetetraaceticacid (EDTA), ethylene glycol tetraacetic acid (EGTA), diethylenetriaminepentaaceticacid (DTPA), N,N-bis(carboxymethyl)glycine (also called nitrilotriacetic acid, NTA), 1,2-bis (o-aminophenoxy)ethane-N,N,N',N'-tetraacetic acid (BAPTA), 2,3-dimercapto-1-propanol (dimercaprol), porphine or heme may be used in cases where the target molecule is a metal ion. As an example, EDTA forms a complex with most monovalent, divalent, trivalent and tetravalent metal ions, such as e.g. silver ($Ag^+$), calcium ($Ca^{2+}$), manganese ($Mn^{2+}$), copper ($Cu^{2+}$), iron ($Fe^{2+}$), cobalt ($Co^{3+}$) and zirconium ($Zr^{4+}$), while BAPTA is specific for $Ca^{2+}$. In some embodiments a respective metal chelator in a complex with a respective metal ion or metal ions defines the linking moiety. Such a complex is for example a receptor molecule for a peptide of a defined sequence, which may also be included in a protein. As an illustrative example, a standard method used in the art is the formation of a complex between an oligo histidine tag and copper ($Cu^{2+}$), nickel ($Ni^{2+}$), cobalt ($Co^{2+}$), or zink ($Zn^{2+}$) ions, which are presented by means of the chelator nitrilotriacetic acid (NTA).

Avidin or streptavidin may for instance be employed to immobilise a biotinylated nucleic acid, or a biotin containing monolayer of gold may be employed (Shumaker-Parry, J. S., et al., Anal. Chem. (2004) 76, 918). As yet another illustrative example, the biomolecule may be locally deposited, e.g. by scanning electrochemical microscopy, for instance via pyrroleoligonucleotide patterns (e.g. Fortin, E., et al., Electroanalysis (2005) 17, 495). In other embodiments, in particular where the biomolecule is a nucleic acid, the biomolecule may be directly synthesised on the surface of the immobilisation unit, for example using photoactivation and deactivation.

As an illustrative example, the synthesis of nucleic acids or oligonucleotides on selected surface areas (so called "solid phase" synthesis) may be carried out using electrochemical reactions using electrodes. An electrochemical deblocking step as described by Egeland & Southern (Nucleic Acids Research (2005) 33, 14, e125) may for instance be employed for this purpose. A suitable electrochemical synthesis has also been disclosed in US patent application US 2006/0275927. In some embodiments light-directed synthesis of a biomolecule, in particular of a nucleic acid molecule, including UV-linking or light dependent 5'-deprotection, may be carried out.

The molecule that has a binding affinity for a selected target molecule may be immobilised on the nanocrystals by any means. As an illustrative example, an oligo- or polypeptide, including a respective moiety, may be covalently linked to the surface of nanocrystals via a thio-ether bond, or example by using ω functionalized thiols. Any suitable molecule that is capable of linking a nanocrystal of an embodiment of the invention to a molecule having a selected binding affinity may be used to immobilise the same on a nanocrystal. For instance a (bifunctional)linking agent such as ethyl-3-dimethylaminocarbodiimide, N-(3-aminopropyl)

3-mercaptobenzamide, 3-aminopropyl-trimethoxysilane, 3-mercaptopropyl-trimethoxysilane, 3-(trimethoxysilyl) propyl-maleimide, or 3-(trimethoxysilyl) propyl-hydrazide may be used. Prior to reaction with the linking agent, the surface of the nanocrystals can be modified, for example by treatment with glacial mercaptoacetic acid, in order to generate free mercaptoacetic groups which can then employed for covalently coupling with an analyte binding partner via linking agents.

Embodiments of the present invention also include a hydrogel, which can be taken to be a water-swollen water-insoluble polymeric material. The hydrogel includes, including contains and consists of, a peptide and/or peptoid as defined above. Since a hydrogel maintains a three dimensional structure, a hydrogel of an embodiment of the invention may be used for a variety of applications. Since the hydrogel has a high water content and includes amino acids, it is typically of excellent biocompatibility.

A hydrogel according to an embodiment of the invention is formed by self-assembly. The inventors have observed that the peptides/peptoids assemble into fibers that form mesh-like structures. Without being bound by theory hydrophobic interaction between non-polar portions of peptides/peptoids as disclosed herein are contemplated to assist such self-assembly process.

The method of forming the hydrogel includes dissolving the peptide/peptoid in aqueous solution. Agitation, including mixing such as stirring, and/or sonication may be employed to facilitate dissolving the peptide/peptoid. In some embodiments the aqueous solution with the peptide/peptoid therein is exposed to a temperature below ambient temperature, such as a temperature selected from about 2° C. to about 15° C. In some embodiments the aqueous solution with the peptide/peptoid therein is exposed to an elevated temperature, i.e. a temperature above ambient temperature. Typically the aqueous solution is allowed to attain the temperature to which it is exposed. The aqueous solution may for example be exposed to a temperature from about 25° C. to about 85° C. or higher, such as from about 25° C. to about 75° C., from about 25° C. to about 70° C., from about 30° C. to about 70° C., from about 35° C. to about 70° C., from about 25° C. to about 60° C., from about 30° C. to about 60° C., from about 25° C. to about 50° C., from about 30° C. to about 50° C. or from about 40° C. to about 65° C., such as e.g. a temperature of about 40° C., about 45° C., about 50° C., about 55° C., about 60° C. or about 65° C. The aqueous solution with the peptide/peptoid therein may be maintained at this temperature for a period of about 5 min to about 10 hours or more, such as about 10 min to about 6 hours, about 10 min to about 4 hours, about 10 min to about 2.5 hours, about 5 min to about 2.5 hours, about 10 min to about 1.5 hours or about 10 min to about 1 hour, such as about 15 min, about 20 min, about 25 min, about 30 min, about 35 min or about 40 min.

A hydrogel according to an embodiment of the invention may be included in a fuel cell, here it may for example provide a substrate between the anode and the cathode. A liquid electrolyte may be encompassed by the hydrogel. Likewise, a hydrogel according to an embodiment of the invention may provide a substrate between two electrodes in an electrophoresis apparatus. The hydrogel may also be conducting. The hydrogel may also serve in enhancing the efficiency of charge-separated states and/or slowing down charge recombination. The hydrogel may thus be applied in any form photovoltaics, including a solar cell.

In some embodiments a hydrogel disclosed herein is a biocompatible, including a pharmaceutically acceptable hydrogel. The term "biocompatible" (which also can be referred to as "tissue compatible"), as used herein, is a hydrogel that produces little if any adverse biological response when used in vivo. The term thus generally refers to the inability of a hydrogel to promote a measurably adverse biological response in a cell, including in the body of an animal, including a human. A biocompatible hydrogel can have one or more of the following properties: non-toxic, non-mutagenic, non-allergenic, non-carcinogenic, and/or non-irritating. A biocompatible hydrogel, in the least, can be innocuous and tolerated by the respective cell and/or body. A biocompatible hydrogel, by itself, may also improve one or more functions in the body.

Depending on the amino acids that are included in the peptide/peptoid that is included in a hydrogel, a respective hydrogel may be biodegradable. A biodegradable hydrogel gradually disintegrates or is absorbed in vivo over a period of time, e.g., within months or years. Disintegration may for instance occur via hydrolysis, may be catalysed by an enzyme and may be assisted by conditions to which the hydrogel is exposed in a human or animal body, including a tissue, a blood vessel or a cell thereof. Where a peptide is made up entirely of natural amino acids, a respective peptide can usually be degraded by enzymes of the human/animal body.

A hydrogel according to an embodiment of the invention may also serve as a depot for a pharmaceutically active compound such as a drug. A hydrogel according to an embodiment of the invention may be designed to mimic the natural extracellular matrix of an organism such as the human or animal body. A fiber formed from the peptide/peptoid of an embodiment of the invention, including a respective hydrogel, may serve as a biological scaffold. A hydrogel of an embodiment of the invention may be included in an implant, in a contact lens or may be used in tissue engineering. In one embodiment, the peptides consist typically of 3-7 amino acids and are able to self-assemble into complex fibrous scaffolds which are seen as hydrogels, hen dissolved in water or aqueous solution. These hydrogels can retain water up to 99.9% and possess sufficiently high mechanical strength. Thus, these hydrogels can act as artificial substitutes for a variety of natural tissues without the risk of immunogenicity. The hydrogels in accordance with the present invention may be used for cultivating suitable primary cells and thus establish an injectable cell-matrix compound in order to implant or reimplant the newly formed cell-matrix in vivo. Therefore, the hydrogels in accordance with the present invention are particularly useful for tissue regeneration or tissue engineering applications. As used herein, a reference to an "implant" or "implantation" refers to uses and applications of/for surgical or arthroscopic implantation of a hydrogel containing device into a human or animal, e.g. mammalian, body or limb. Arthroscopic techniques are taken herein as a subset of surgical techniques, and any reference to surgery, surgical, etc., includes arthroscopic techniques, methods and devices. A surgical implant that includes a hydrogel according to an embodiment of the invention may include a peptide and/or peptoid scaffold. This the peptide and/or peptoid scaffold may be defined by the respective hydrogel. A hydrogel of an embodiment of the invention may also be included in a wound cover such as gauze or a sheet, serving in maintaining the wound in a moist state to promote healing.

Depending on the amino acid sequence used in the peptide/peptoid the hydrogel may be temperature-sensitive. It may for instance have a lower critical solution temperature or a temperature range corresponding to such lower critical solution temperature, beyond which the gel collapses as hydrogen bonds by water molecules are released as water molecules are released from the gel.

The disclosed subject matter also provides improved chiral amphiphilic natural-based peptides and/or peptoids that assemble to peptide/peptoid hydrogels with very favorable material properties. The advantage of these peptide/peptoid hydrogels is that they are accepted by a variety of different primary human cells, thus providing peptide scaffolds that can be useful in the repair and replacement of various tissues. Depending on the chirality of the peptide monomer the character of the hydro gels can be designed to be more stable and less prone to degradation though still biocompatible.

A hydrogel and/or a peptide/peptoid described herein can be administered to an organism, including a human patient per se, or in pharmaceutical compositions where it may include or be mixed with pharmaceutically active ingredients or suitable carriers or excipient(s). Techniques for formulation and administration of respective hydro gels or peptides/peptoids resemble or are identical to those of low molecular weight compounds well established in the art. Exemplary routes include, but are not limited to, oral, transdermal, and parenteral delivery. A hydrogel or a peptide/peptoid may be used to fill a capsule or tube, or may be provided in compressed form as a pellet. The peptide/peptoid or the hydrogel may also be used in injectable or sprayable form, for instance as a suspension of a respective peptide/peptoid.

A hydrogel of an embodiment of the invention may for instance be applied onto the skin or onto a wound. Further suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. It is noted in this regard that for administering microparticles a surgical procedure is not required. Where the microparticles include a biodegradable polymer there is no need for device removal after release of the anti-cancer agent. Nevertheless the microparticles may be included in or on a scaffold, a coating, patch, composite material, a gel or a plaster.

In some embodiments one may administer a hydrogel and/or a peptide/peptoid in a local rather than systemic manner, for example, via injection.

Pharmaceutical compositions that include a hydrogel and/or a peptide/peptoid of an embodiment of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with an embodiment of the present invention thus may be formulated in conventional manner using one or more physiologically acceptable carriers including excipients and auxiliaries that facilitate processing of the hydrogel and/or peptide/peptoid into preparations that can be used pharmaceutically. Proper formulation is dependent upon the route of administration chosen.

For injection, the peptide/peptoid of an embodiment of the invention may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the hydrogel and/or peptide/peptoid can be formulated readily by combining them with pharmaceutically acceptable carriers well known in the art. Such carriers enable the hydrogel and/or peptide/peptoid, as well as a pharmaceutically active compound, o be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatine, as well as soft, sealed capsules made of gelatine and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the peptides/peptoids may be suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

The hydrogel and/or peptide/peptoid may be formulated for parenteral administration by injection, .g., y intramuscular injections or bolus injection or continuous infusion. Formulations for injection may be presented in unit dosage form, e.g., in ampules or in multi-dose containers, with an added preservative. The respective compositions may take such forms as suspensions, solutions or emulsions in oily or aqueous vehicles, and may contain formulator agents such as suspending, stabilizing and/or dispersing agents. The hydrogel and/or peptide/peptoid may be formulated for other drug delivery systems like implants, or trandermal patches or stents.

Examples

Experiments have been performed to illustrate the technical aspects of exemplary embodiments of the present invention. The following examples are described in the Experimental Methods and Results. The skilled artisan will readily recognize that the examples are intended to be illustrative and are not intended to limit the scope of the present invention.

Experimental Methods and Results

Peptides

The peptide sequences were designed to represent an amphiphilic peptide structure containing a hydrophilic head group and a hydrophobic tail. The rationale for the peptides design was to create a peptide monomer of decreasing size resembling a cone shaped structure. The hydrophobic tail differs by using different aliphatic amino acids. It is consisting of the following aliphatic amino acids such as glycine, alanine, valine, leucine and isoleucine and the hydrophilic head group is consisting of one or two polar or charged amino acids. The sequence order of the hydrophobic tail differed by using different aliphatic amino acids. The peptides were commercially synthesized from GL Biochem, Shanghai, China. In order to verify the reproducibility of the peptide hydro gel-forming behavior peptides were also synthesized from other companies (Biomatik Corp., Anaspec. Inc, USA). The peptides have a purity of equal or higher than 95% verified by High-performance liquid chromatography (HPLC) and mass spectrometry. The peptide stock solutions were dissolved in water at 5 to 10 mg/ml. Most of the peptides are acetylated at the N-terminus.

Peptide-Based Hydrogel Preparation

All peptides (GL Biochem, Shanghai, China, ≥98% purity) were freshly prepared in order to avoid premature peptide aggregation. The peptides were dissolved in water and left at room temperature to form hydrogels. Depending on the peptide concentration, the self-assembly process occurred immediately, within hours or even within days (experimental time frame for gelation). For higher peptide concentrations peptides were dissolved in milliQ water by vortexing. If a forced and accelerated hydrogel preparation was needed, the peptide solution was subjected to sonication in a water bath (Barnstead Labline 9319 UltrasonicLC60H). No significant structural differences were observed between hydrogels produced via self-assembly and those whose assembly was facilitated by sonication. Few peptides formed hydrogels more easily at elevated temperatures, i.e. at 50° C.

To study the effect of concentration variation, both AcLD$_6$ (L) and AciD$_3$ (L) hydrogels were prepared with varying concentration as specified above. To study the effect of monovalent and divalent cations, AcLD$_6$ (L) hydrogels were prepared by dissolving peptide in 10, 50, 100 and 150 mM NaCl and CaCl$_2$ solutions. FESEM and rheology studies were further performed to characterize the morphology and strength of these hydro gels.

Preparation of gelatin and collagen gels: Gelatin (Type A, G 1890; Sigma Aldrich) hydrogels was prepared by first dissolving gelatin in milli Q water by heating followed by cooling till the gelation was observed. Collagen (Type I from bovine, Advanced Biomatrix, USA) was diluted with PBS buffer to a concentration of 1.5 mg/ml and titrated to pH 7.4 using 0.1M NaOH. Gelation was achieved by incubating the solution at 37° C. for 1 hour.

Circular Dichroism (ω) Spectroscopy

Secondary peptide structures were analyzed by measuring ellipticity spectra using the Aviv Circular Dichroism Spectrometer, model 410. ω samples were prepared by diluting stock peptides solutions (5-10 mg/ml) in water. The diluted peptide solutions were filled in to a cuvette with 1 mm path length and spectra were acquired. As a blank reference water was used and the reference was subtracted from the raw data before molar ellipticity was calculated. The calculation was based on the formula: $[\theta]\lambda = \theta_{obs} \times 1/(10 \text{ Lcn})$, where $[\theta]\lambda$ the molar ellipticity at $\lambda$, in deg cm$^2$ d/mol, is the observed ellipticity at $\lambda$ in mdeg, L is the path length in cm, c is the concentration of the peptide in M, and n is the number of amino acids in the peptide. Secondary structure analysis was done using CDNN software.

Environmental Scanning Electron Microscopy (ESEM)

Samples were placed onto a sample holder of FEI Quanta 200 Environmental Scanning Electron Microscopy. The surface of interest was then examined using accelerating voltage of 10 kV at a temperature of 4° C.

Field Emission Scanning Electron Microscopy (FESEM)

Samples were frozen at −20° C. and subsequently to −80° C. Frozen samples were further freeze dried. Freeze dried samples were fixed onto a sample holder using conductive tape and sputtered with platinum from both the top and the sides in a JEOL JFC-1600 High Resolution Sputter Coater. The coating current used was 30 mA and the process lasted for 60 sec. The surface of interest was then examined with a JEOL JSM-7400F Field Emission Scanning Electron Microscopy system using an accelerating voltage of 5-10 kV.

Rheological Measurements

To determine the viscoelastic properties of the peptide-based hydro gels, hydro gels were subjected to dynamic time, strain and frequency sweep experiments using the ARES-G2 rheometer (TA Instruments, Piscataway, N.J.) with the 25.0 mm diameter titanium parallel plate geometry and a 0.8 mm gap distance. Oscillatory frequency study was performed to compare the strength of peptide based hydrogel with varying concentration of peptides, or for peptide in presence of monovalent or divalent ions. Oscillatory frequency sweep studies were performed at 0.1-100 rad/s frequency and 0.1% strain at 25° C. and 50° C.

Ac-LD$_6$ [L]:

Peptide Sequence:

Ac-LIVAGD-COOH

Molecular weight: 629.56

(1) Temperature sweep study for Ac-LD$_6$ (L):
 (a) The peptide mixture was then placed on rheometer lower plate. Following parameters were optimized:
 Gap between two plates: 1 mm
 Strain: 10%
 Frequency: 6.28 rad/sec
 Temperature scan: 4° C. to 60° C.
 Sample volume: 500 μl (2) Frequency sweep study for Ac-LD$_6$(L):
 Optimized parameter required to perform frequency sweep study
 Gap between two plates: 0.8 mm
 Strain: 0.1%
 Temperature: 25 and 50° C.
 Sample volume: 1 ml
 Frequency scan: 0.1 rad/sec to 100 rad/sec
 Concentration of Ac-LD-6 (L) in hydrogel: 10 mg/ml (3) Effect of concentration variation of Ac-LD$_6$ (L) on gel strength:
 Optimized parameters that are required to perform frequency sweep studies for measuring gel strength are as follows:
 Gap between two plates: 0.8 mm
 Strain: 0.1%
 Temperature: 25 and 50° C.
 Sample volume: 1 ml
 Frequency scan: 0.1 rad/sec to 100 rad/sec
 Concentrations of Ac-LD$_6$ (L) in hydrogels: 5 mg/ml, 10 mg/ml, 15 mg/ml and, 0 mg/ml and 30 mg/ml in water.

(4) Effect of sodium chloride (NaCl) on the gel strength of Ac-LD$_6$ (L):

Effect of sodium chloride on Ac-LD$_6$ (L) based hydrogels, were studied by performing a frequency sweep study on hydro gels prepared by dispersing 10 mg of Ac-LD-6 (L) in varying concentration of NaCl solution for example 10 mM, 50 mM, 100 mM and 150 mM of NaCl solution using optimized procedure to form hydro gels. Optimized parameter required to perform frequency sweep study to measure gel strength in presence of NaCl are as follows:

Gap between two plates: 0.5 mm and 0.8 mm
Strain: 10% and 0.1% respectively
Temperature: 25° C. and 50° C.
Sample volume: 1 ml
Frequency scan: 0.1 rad/sec to 100 rad/sec
Concentrations of NaCl solutions used to prepare 10 mg/ml of Ac-LD-6 (L) Hydrogels: 10 mM, 50 mM, 100 mM, 150 mM NaCl solution.

Cell Growth Experiments

In order to find out whether the peptide hydrogels can serve as a scaffold for tissue engineering, its biocompatibility was investigated. Different primary human cells were seeded on top of the hydrogel after its gelation in tissue culture medium (DMEM without serum) in 6-well, 4-well or 96-well culture plates, see the culture conditions below. During the next 2-4 days no change of medium was necessary, but eventually fresh media was added to the wells. The cells were analyzed for viability.

Primary human renal proximal tubule cells (HPTCs) and primary human umbilical vein endothelial cells (HUVECs) were obtained from ScienCell Research Laboratories (Carlsbad, Calif., SA). HPTCs were cultivated in basal epithelial cell medium supplemented with 2% fetal bovine serum (FBS) and 1% epithelial cell growth supplement (all components obtained from ScienCell Research Laboratories). The culture medium for HUVECs was endothelial cell medium containing 5% FBS and 1% endothelial cell growth supplement (ScienCell Research Laboratories). All cell culture media used were supplemented with 1% penicillin/streptomycin solution (ScienCell Research Laboratories), and all cells were cultivated at 37° C. in a 5% CO$_2$ atmosphere. The seeding density of the cells was about $5 \times 10^4$ cells/cm$^2$. However since HUVECs are bigger than HPTCs the cell number would be slightly lower than one for HPTC cells (~$4.5 \times 10^4$ cells/cm$^2$). Both cell types had a confluency of about 80% in the wells after seeding.

Crosslinked Hydrogels
Material & Methods
Peptides

All peptides were synthesised at American Peptide Company (CA, USA) using SPPS and purified to >95% (HPLC). Amino acid content (AA %) analysis was performed and the net weight (gross weight×AA %) was used for calculations.

Kinetics of Disulfide Formation

For air oxidation, LK$_6$C was dissolved in MilliQ water by vigorous vortexing for five minutes and dispensed into 20 µL aliquots. At appropriate time points, 180 µL of DTNB (Sigma, Singapore) working solution (4 mg/mL in 0.1M phosphate buffer pH 7.0) was mixed with the peptide solution for 15 minutes. Absorbance at 412 nm was then measured (InfiniteM200, Tecan, Switzerland). Using a calibration curve generated with L-cysteine (Sigma) as standard ($R^2$=0.999), the background-subtracted value was normalised to the reading at 0 hour to give the % of thiol remaining. For H$_2$O$_2$-assissted oxidation, LK$_6$C was dissolved in water (HPLC grade, J. T. Baker, NJ, USA) containing 0.06% H$_2$O$_2$ (Merck, Sinagpore) and dispensed into aliquots. At appropriate time points, the aliquots were analysed using an Aquity® UPLC (Waters, SA) fitted with a single-quadrupole MS. Using a calibration curve generated with pure LK$_6$C as standard ($R^2$=0.999), the area under the peak corresponding to LK$_6$C monomer was normalised to that at 0 hour to give the % of thiol remaining.

Gel Casting

Peptide was dissolved in 200 µL of water+/−H$_2$O$_2$ and filled into custom-made hollow ring casts (diameter ~1 cm). The ring ends were sealed with parafilm to minimise evaporation and the cast was kept at 25° C. for 22 hours before further manipulations.

Rheology: The rheological properties of casted gels were measured with an ARES-G2 (TA Instruments, USA) using the oscillation method. Frequency-sweep studies were performed with ω=0-100 rad/s at strain, γ=0.1%. The gel stiffness was represented by plotting G' against ω. Amplitude-sweep studies were performed beforehand at 1 Hz with γ=0-100%. The LVE limit of the gel was defined as the value of γ when G' first dropped below 90% of the average initial value.

Rheology

The rheological properties of casted gels were measured with an ARES-G2 (TA Instruments, USA) using the oscillation method. Frequency-sweep studies were performed with ω=0-100 rad/s at strain, γ=0.1%. The gel stiffness was represented by plotting G' against ω. Amplitude sweep studies were performed beforehand at 1 Hz with γ=0-100%. The LVE limit of the gel was defined as the value of γ when G' first dropped below 90% of the average initial value.

FESEM

Freeze-dried gels were deposited onto carbon tapes, sputtered with platinum and observed under a JSM-7400F electron microscope (Jeol, Tokyo, Japan).

3D Cell Culture

LK$_6$C+/−CRGD gels were casted directly into 8-chamber Lab-Tek® wells (Nunc, N.Y., USA) and purified as reported in the SI. 0.5 mL of cell suspension in regular completed DMEM (Invitrogen, Singapore) was either seeded onto the gel or directly into the well (2D control) and incubated for four days. 0.5 µL of calcein-AM (Invitrogen) was then added to the media to identify live cells and images were captured using a confocal microscope (LSM5 DUO, Carl Zeiss, Germany). Beforehand, calcein-AM was verified to stain only live cells as ethanol- and H$_2$O$_2$-treated cells excluded the dye. All images, except for the 2D controls, were presented as mergers of several z-stacks. To further verify the 3D distribution of cells, the gel was embedded vertically in Jung Tissue Freezing Medium (Leica Instruments GmbH, Germany) and 20 µm cross-sectional slices were obtained with a cryostat (CM3050 S, Leica). Sections were mounted with coverslips and imaged as above.

Quantification of Cell-Spread Area

Confocal images after calcein staining were processed using ImageJ (NIH, USA) to obtain the average cell-spread area under various culture conditions. For cells in 3D gel culture, images used for quantification were mergers of several z-stacks to capture the maximum cell-spread area. In all cases, at least three independent experiments with at least two locations selected from each culture were used for averaging.

MTT Viability Assay

After four days of 3D gel culture, cells were separated from the substrate by trypsination and centrifugation and re-seeded into 48-well plates (Nunc) overnight for attachment. MTT (Sigma) dissolved in PBS was then added to the media for four hours, before the formazan crystals were dissolved using DMSO (Sigma). Absorbance was read at 560 nm, subtracted with the 680 nm reference and normalised to the appropriate control to give an indication of relative cell viability.

Statistical Analysis

ANOVA testing (OriginLab Corporation, MA, USA) was performed on sample means with p<0.05 being denoted by * and accepted to be statistically significant.

Results $LK_6C$ Peptides can be Casted into 3-Dimensional Shapes $LK_6C$ peptides can be easily casted into 3-dimensional gels using the appropriate moulds (see FIG. 18). In this experiment, a mould in the shape of a ring was used and $LK_6C$ gels were casted using water or completed growth medium. Dextran particles, employed here as a model cargo, could also be encapsulated within the gel matrix.

$H_2O_2$-Assisted Formation of Disulfide Crosslinks

The kinetics of disulfide formation under air oxidation is inefficient (FIG. 19). The addition of $H_2O_2$ speeds up disulfide formation (FIG. 20). LC-MS confirms the formation of disulfide-crosslinked dimers in the presence of $H_2O_2$ (FIG. 21). The data further suggests that the addition of HRP has no significant effect on the kinetics of disulfide formation (FIG. 19). The rate of disulfide formation can also be accelerated by increasing the amount of $H_2O_2$ used (FIG. 22).

Oxidation Strategy

Two different methods were devised for the $H_2O_2$-assissted cross-linking: 1) The cast-and-soak method, where the gel is first being casted overnight before being soaked in an oxidative solution. 2) The in situ oxidation method where the aqueous solution used to dissolve the peptide powder already contains the oxidative agent (FIG. 23).

Oxidation Increases the Long-Term Stability of $LK_6C$ in Water $LK_6$ or $LK_6C$ gels were first casted and then soaked in water for various durations. After 24 hours of water soak, the non-crosslinkable LK6 gels were completely degraded while the non-oxidised $LK_6C$ gels were severely degraded (FIG. 24). In stark contrast, $LK_6C$ gels oxidised for 2 hours using the cast-and-soak method and $LK_6C$ gels oxidised in situ remained intact after 96 hours of water soak. These observations are also supported by rheological measurements (FIG. 28). Therefore, the strategy of disulfide cross-linking has increased the resistance of the gel to degradation and has made it possible to use the gel at a lower concentration compared to previous formulations. This, in turn, will translate into significant cost savings.

Gel Oxidised Using the Cast-and-Soak Method is Uniformly Oxidised $LK_6C$ gels were casted overnight and then soaked in $H_2O_2$ solution for 2 hours (see scheme in FIG. 25). Then the surfaces (circumference+top+bottom layers) were separated from the core and it was shown that the amount of $H_2O_2$ and disulfide/thiol ratio of both the layers were comparable (FIGS. 25 and 26). This suggests that oxidation is not restricted to the surfaces of the gel and that the diffusion of $H_2O_2$ is rapid in this experimental set-up. However, if the gel is casted into a 48-well plate and the $H_2O_2$ solution is merely applied over the top of the gel (as per later experiments, see scheme in FIG. 31), the diffusion rate of $H_2O_2$ will be reduced as only the top surface is accessible to the solution in this configuration.

Effects of Oxidation on G' and Elasticity of the Gel

The rheological properties of various $LK_6C$ gels were next quantified. As a measure of stiffness, the elastic modulus, G' was plotted against angular frequency, ω after the gel was subjected to 2-24 hours of cast-and-soak oxidation with 0.06% $H_2O_2$, or 24 hours of in situ oxidation with 0.03-0.1% $H_2O_2$ (FIG. 27 A). Compared to non-oxidised gels, the stiffness was either maintained or increased following different oxidation regimes. Interestingly, the stiffness achieved after 24 hours of cast-and-soak differed from that after in situ oxidation with 0.06% $H_2O_2$. This could be due to the different availability of $H_2O_2$ and sequence of oxidation. More specifically, in cast-and-soak, the gel has access to a sink of $H_2O_2$ and cross-linking happens only after self-assembly of peptide fibers; while during in situ oxidation, $H_2O_2$ is limited to the gel volume and cross-linking occurs concurrently with self-assembly. The linear viscoelastic (LVE) limit (elasticity) of the gel, however, increased 2.4-3.8 fold following oxidation (FIG. 27B). This is presumably attributed to the introduction of additional chemical bonds. Other strategies to modulate the stiffness and elasticity of $LK_6C$ gels include varying its concentration (FIG. 29A/B) or doping $LK_6C$ with LK6 (FIG. 29C/D). This also allows the tuning of the amount of thiol groups available in the gel.

Fibrous Microstructures of Gels

Field emission scanning electron microscopy (FESEM) revealed that the fibrous microstructures of $LK_6C$ gels were maintained after various oxidation regimes (FIG. 30).

$H_2O_2$ and Residual Acid Readily Removed

Using a configuration closer to cell culture experiments, gels were casted overnight in 48-well plates and water was applied over the gels to purify it before the introduction of cells. The majority of $H_2O_2$ and residual acid can be removed be simply changing the water regularly (FIG. 31). Growth medium can be used instead of water to ensure that the gel is essentially free of $H_2O_2$ and adjusted to a pH amenable for cell culture.

Gradual and Tunable Release Kinetics

As a model system, dextran particles were encapsulated within the gel and their release profile monitored. No burst release was observed in both cases and release rate was suppressed in the oxidized sample, presumably due to the increased stability in water (FIG. 32).

Functionalization of the Hydrogel

The gel was next functionalized with a bioactive signal. CRGD (0-1 mg/mL) was simply mixed with $LK_6C$ (fixed at 10 mg/mL, i.e., CRGD ligand density 0-9. 1 gross weight %) in the presence of $H_2O_2$ and ring-casted overnight. UPLC-MS confirmed the formation of $LK_6C$–CRGD conjugate and the disappearance of free CRGD (FIG. 33). The mild and simple reaction conditions are to be noted. A person skilled in the art will also recognize the versatility of this peptide platform as well as the fact that future conjugations need not be limited to RGD. The gels were next purified by a dialysis-inspired method whereby water was layered on top and changed regularly. Doing so, >96% of unreacted $H_2O_2$ was removed after 4 hrs and >99% after 7 hrs (FIG. 31 A). Similarly, >85% of residual acid from SPPS was removed after 8 hrs (FIG. 31 B).

Biocompatibility and Use for Cell Culture

To test for biocompatibility, HepG2 cells were either seeded directly into wells (2D control) or onto purified $LK_6C$ gels conjugated with different concentrations of RGD. After four days, calcein staining revealed that cells were viable in all experiments (FIG. 34 A/B). This was repeated with primary rabbit fibroblasts (FIG. 35), 3T3 murine fibroblasts (FIG. 38) and NIH-3T3 murine fibroblasts (data not shown), confirming the biocompatibility of the gels. With regular media changes, cells remained viable for at least 3 weeks (FIG. 38). Images obtained from the gel cultures were presented as mergers of several z-stacks. While that may already suggest a 3D distribution, the inventors wanted to verify that they were not artifacts due to, e.g., the meniscus on gel surfaces or the gel being casted in a non-horizontal position. The gels were therefore embedded vertically and cross-sectional slices were obtained for depth profiling. From FIG. 34B, calcein-stained cells were observed to infiltrate the gel, resulting in multi-layered growth and validating their 3D spatial distribution. As visually suggested in FIG. 34A, HepG2 cells appeared to have proliferated faster within gels with RGD compared to the ones without.

This was supported by data from the MTT assay (FIG. 34C). Being an anchorage-dependent cell line, the better adhesion to RGD conjugated gels presumably provided the cells with a more ideal growth environment. Higher magnification images (FIG. 36) were subsequently taken and the average cell-spread area of HepG2 cells was quantified. Interestingly, 3D gel culture had insignificant effects ($p>0.05$) on the average cell-spread area of HepG2 cells compared to those in regular 2D culture (FIG. 34D). The amount of RGD ligand present also did not significantly ($p>0.05$) impact the cell spreading area of HepG2 cells. The trend was different, though, in the case of primary rabbit fibroblasts (FIG. 35B) and NIH-3T3 murine fibroblasts (data not shown), both of which spreaded more in 2D culture. Cells are known to respond to mechanical properties such as stiffness and elasticity of their microenvironment and these observations are consistent with an earlier report that hydrogel-encapsulated murine fibroblasts maintained rounder morphologies. However, while a transition from 2D to 3D culture caused the fibroblasts to spread differently, the amount of RGD ligand present had insignificant effects ($p>0.05$). Compared to before CRGD attachment, the gel was as stiff (FIG. 37 A) but less elastic (FIG. 37B) after conjugation.

Non-Allergenicity and Non-Toxicity

Experiments conducted by the CRO Toxikon further showed that $LK_6C$ was non-allergenic and non-toxic. More particularly, $LK_6C$ caused no sensitization on the skins of guinea pigs in the direct contact Kligman maximization test during a GLP study conducted by Toxikon according to the ISO 10993-10 guidelines. Also, $LK_6C$ exhibited no significant toxicity in the direct contact V79 colony assay in another GLP study performed by Toxikon.

Use in Wound Treatment

A first round of wound healing experiments with mice was conducted. In this model, the epidermis and dermis of mice we removed to simulate injury (FIG. 39). The following groups were analyzed:
a) No treatment control (i.e., simply bandage up the wound)
b) Application of $LK_6C$–CRGD gel
c) Application of $LK_6C$–CRGD gel with 3T3 murine fibroblasts cultured in 3D Here, the fibroblasts (the major population of the dermis) act as a therapeutic/bioactive agent. The hypothesis is that the 3T3 cells secrete factors that encourage the growth of keratinocytes, which make up the epidermis. This should further aid healing as compared to the gel-only treatment (group b). After 2 weeks, the extent of vascularisation of the wound (a prerequisite feature of recovery) was indeed most significant in group c, followed by group b and then group a (FIG. 40). Subsequent histology also showed the regeneration of a significant dermal layer in group c mice. In comparison, group b mice had less regenerated dermis, and group a mice had the least extent of dermal regeneration.

Summary

Cysteine-mediated disulfide-crosslinked ultra small peptide hydrogel were analyzed. Cross-linking was driven by $H_2O_2$ and produced only water as a by-product. Moreover, $H_2O_2$ helped to maintain the sterility of the gel and can be virtually removed before the introduction of cells. Oxidation increased both the elasticity of the gel and its ability to keep its shape after being soaked in water. Due to the cysteine residue, bioactive signals can be conjugated to the peptide fibers using facile chemistry and gels can be easily purified. Gels formed were shown to support the true 3D distribution of cells and influence their growth and spreading characteristics. Furthermore, their applicability in wound treatment was demonstrated.

The listing or discussion of a previously published document in this specification should not necessarily be taken as an acknowledgement that the document is part of the state of the art or is common general knowledge. All documents listed are hereby incorporated herein by reference in their entirety for all purposes.

Exemplary embodiments of the invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed maybe resorted to by those skilled in the art, and that such modifications and variations are considered to be within the scope of this invention.

The invention has been described broadly and generically herein. Each of the narrower species and sub generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method of preparing a cell culture substrate, preparing a device for drug or gene delivery, or preparing a wound dressing or implant that gels in situ, the method comprising:
preparing a hydrogel by a method comprising steps of:
dissolving amphiphilic peptides having the general formula:

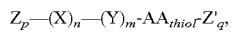

wherein
Z is an N-terminal protecting group,
X is, at each occurrence, independently selected from an aliphatic amino acid,
Y is, at each occurrence, independently selected from a hydrophilic amino acid,
$AA_{thiol}$ is an amino acid comprising a thiol group,
Z' is a C-terminal protecting group,
n is an integer selected from 2 to 6,
m is selected from 0, 1 and 2,
and p and q are independently selected from 0 and 1,
in an aqueous solution,
wherein the aqueous solution comprises an oxidizing agent or
wherein the method further comprises the step of exposing the ready-made hydrogel to a solution of an oxidizing agent,
forming the hydrogel into the cell culture substrate, the device for drug or gene delivery, or the wound dressing or implant that gels in situ.

2. The method of claim 1, wherein the amino acid comprising a thiol group is selected from cysteine and homocysteine.

3. The method of claim 1, wherein the oxidizing agent is $H_2O_2$.

4. The method of claim 1, wherein the amphiphilic peptides are dissolved at a concentration from 0.01 µg/ml to 50 mg/ml; and
optionally wherein the dissolved amphiphilic peptides in aqueous solution are further exposed to a temperature in the range of from 20° C. to 90° C.; and
optionally wherein the dissolved amphiphilic peptides in aqueous solution are exposed to the temperature for at least 1 hour.

5. The method of claim 1, wherein the method further comprises a step of:
exposing the ready-made hydrogel to an aqueous solution not comprising the oxidizing agent, wherein, if the method comprises the step of exposing the ready-made hydrogel to a solution of the oxidizing agent, the step of exposing the ready-made hydrogel to an aqueous solution not comprising the oxidizing agent is performed after the step of exposing the ready-made hydrogel to a solution of the oxidizing agent.

6. The method of claim 5, wherein the step of exposing the ready-made hydrogel to an aqueous solution not comprising the oxidizing agent is repeated at least once; and
optionally wherein the step of exposing the ready-made hydrogel to an aqueous solution not comprising the oxidizing agent occurs for at least 1 hour; and
optionally wherein the step of exposing the ready-made hydrogel to an aqueous solution not comprising the oxidizing agent occurs at a temperature in the range of from 30° C. to 45° C.

7. The method of claim 1, wherein the method comprises at least one of step of:
adding at least one of a microorganism, a cell, a virus particle, a peptide, a peptoid, a protein, a nucleic acid, an oligosaccharide, a polysaccharide, a vitamin, an inorganic molecule, a nano- or microparticle, a synthetic polymer, a small organic molecule, a cosmetic agent or a pharmaceutically active compound;
adding at least one non-peptidic polymer;
adding at least one gelation enhancer; or
adding at least one buffer.

8. The method of claim 7, wherein the gelation enhancer is a salt or a solution of a salt.

9. The method of claim 1, wherein the N-terminal protecting group is any of a group of the general formula —C(O)—R, wherein R is selected from the group consisting of H, unsubstituted or substituted alkyls, and unsubstituted or substituted aryls; or
a peptidomimetic molecule, including natural and synthetic amino acid derivatives, wherein the N-terminus of the peptidomimetic molecule may be modified with a functional group selected from the group consisting of carboxylic acid, amide, alcohol, aldehyde, amine, imine, nitrile, an urea analog, thiol, phosphate, carbonate, sulfate, nitrate, maleimide, vinyl sulfone, azide, alkyne, alkene, carbohydrate, imide, peroxide, ester, thioester, aryl, ketone, sulphite, nitrite, phosphonate and silane.

10. The method of claim 1, wherein the C-terminal protecting group is any one of an amide group or an ester group; or
a peptidomimetic molecule, including natural and synthetic amino acid derivatives, wherein the C-terminus of the peptidomimetic molecule may be modified with a functional group selected from the group consisting of carboxylic acid, amide, alcohol, aldehyde, amine, imine, nitrile, an urea analog, thiol, phosphate, carbonate, sulfate, nitrate, maleimide, vinyl sulfone, azide, alkyne, alkene, carbohydrate, imide, peroxide, ester, thioester, aryl, ketone, sulphite, nitrite, phosphonate and silane.

11. The method of claim 1, wherein, for a given amphiphilic peptide, the aliphatic amino acid, the hydrophilic amino acid and the amino acid comprising a thiol group are either D-amino acids or L-amino acids.

12. The method of claim 1, wherein the hydrophilic amino acid has a polar group which is independently selected from a hydroxyl, an ether, a carboxyl, an imido, an amido, an ester, an amino, a guanidino, a thio, a thioether, a seleno, and a telluro group.

13. The method of claim 1, wherein the aliphatic amino acid is selected from the group consisting of isoleucine, norleucine, leucine, valine, alanine, glycine, homoallylglycine and homopropargylglycine.

14. The method of claim 1, wherein all or a portion of the aliphatic amino acids of the amphiphilic peptides are arranged in an order of decreasing amino acid size in the direction from N- to C-terminus of the amphiphilic peptides, wherein the size of the aliphatic amino acids is defined as I=L>V>A>G.

15. The method of claim 1, wherein the aliphatic amino acids arranged in an order of decreasing amino acid size have a sequence selected from LIVAG (SEQ ID NO. 54), ILVAG (SEQ ID NO. 55), LIVAA (SEQ ID NO. 56), LAVAG (SEQ ID NO. 57), IVAG (SEQ ID NO. 58), LIVA (SEQ ID NO. 59), LIVG (SEQ ID NO. 60), IVA and IV, wherein, optionally, there is an A preceding such sequence at the N-terminus.

16. The method of claim 1, wherein the amphiphilic peptides are the same or different.

17. The method of claim 1, wherein $(X)_n$-$(Y)_m$-$AA_{thiol}$ is selected from the group consisting of LIVAGKC (SEQ ID NO: 43), LIVAGSC (SEQ ID NO: 44), LIVAGDC (SEQ ID NO: 45), ILVAGKC (SEQ ID NO: 46), ILVAGDC (SEQ ID NO: 47), LIVAGC (SEQ ID NO: 48), AIVAGC (SEQ ID NO: 49), ILVAGC (SEQ ID NO: 50), IVKC (SEQ ID NO: 51), IVDC (SEQ ID NO: 52) and IVSC (SEQ ID NO: 53).

18. The method of claim 1, wherein at least 5% of the plurality of amphiphilic peptides are chemically cross-linked.

* * * * *

SEQUENCE LISTING

<160> NUMBER OF SEQ ID NOS: 60

<210> SEQ ID NO 1
<211> LENGTH: 7

```
<212> TYPE: PRT
<213> ORGANISM: Artificial Sequence
<220> FEATURE:
<223> OTHER INFORMATION: Chemically synthesized peptide

<400> SEQUENCE: 1

Leu Ile Val Ala Gly Asp Asp
1               5

<210> SEQ ID NO 2
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 2

Leu Ile Val Ala Gly Asp
1               5

<210> SEQ ID NO 3
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 3

Leu Ile Val Ala Gly Asp
1               5

<210> SEQ ID NO 4
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 4

Ala Ile Val Ala Gly Asp
1               5

<210> SEQ ID NO 5
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 5

Ala Ile Val Ala Gly Asp
1               5

<210> SEQ ID NO 6
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 6

Ile Leu Val Ala Gly Asp
1               5

<210> SEQ ID NO 7
<211> LENGTH: 6
<212> TYPE: PRT
```

```
<213> ORGANISM: Artificial Sequence
<220> FEATURE:
<223> OTHER INFORMATION: Chemically synthesized peptide

<400> SEQUENCE: 7

Ile Leu Val Ala Gly Asp
1               5

<210> SEQ ID NO 8
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 8

Leu Ala Val Ala Gly Asp
1               5

<210> SEQ ID NO 9
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 9

Leu Ile Val Ala Ala Asp
1               5

<210> SEQ ID NO 10
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 10

Leu Ile Val Ala Gly Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 11

Leu Ile Val Ala Gly Ser
1               5

<210> SEQ ID NO 12
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 12

Ala Ile Val Ala Gly Ser
1               5

<210> SEQ ID NO 13
<211> LENGTH: 6
<212> TYPE: PRT
<213> ORGANISM: Artificial Sequence
```

```
<220> FEATURE:
<223> OTHER INFORMATION: Chemically synthesized peptide

<400> SEQUENCE: 13

Ile Leu Val Ala Gly Ser
1               5

<210> SEQ ID NO 14
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 14

Leu Ile Val Ala Gly Thr
1               5

<210> SEQ ID NO 15
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 15

Ala Ile Val Ala Gly Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Chemically synthesized peptide

<400> SEQUENCE: 16

Leu Ile Val Ala Gly Glu Glu
1               5

<210> SEQ ID NO 17
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 17

Leu Ile Val Ala Gly Glu
1               5

<210> SEQ ID NO 18
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 18

Leu Ile Val Ala Gly Glu
1               5

<210> SEQ ID NO 19
<211> LENGTH: 6
<212> TYPE: PRT
<213> ORGANISM: Artificial Sequence
<220> FEATURE:
```

-continued

```
<223> OTHER INFORMATION: Chemically synthesized peptide

<400> SEQUENCE: 19

Leu Ile Val Ala Gly Lys
1               5

<210> SEQ ID NO 20
<211> LENGTH: 5
<212> TYPE: PRT
<213> ORGANISM: Artificial Sequence
<220> FEATURE:
<223> OTHER INFORMATION: Chemically synthesized peptide

<400> SEQUENCE: 20

Leu Ile Val Ala Asp
1               5

<210> SEQ ID NO 21
<211> LENGTH: 5
<212> TYPE: PRT
<213> ORGANISM: Artificial Sequence
<220> FEATURE:
<223> OTHER INFORMATION: Chemically synthesized peptide

<400> SEQUENCE: 21

Leu Ile Val Gly Asp
1               5

<210> SEQ ID NO 22
<211> LENGTH: 4
<212> TYPE: PRT
<213> ORGANISM: Artificial Sequence
<220> FEATURE:
<223> OTHER INFORMATION: Chemically synthesized peptide

<400> SEQUENCE: 22

Ile Val Ala Asp
1

<210> SEQ ID NO 23
<211> LENGTH: 4
<212> TYPE: PRT
<213> ORGANISM: Artificial Sequence
<220> FEATURE:
<223> OTHER INFORMATION: Chemically synthesized peptide

<400> SEQUENCE: 23

Ile Val Ala Asp
1

<210> SEQ ID NO 24
<211> LENGTH: 3
<212> TYPE: PRT
<213> ORGANISM: Artificial Sequence
<220> FEATURE:
<223> OTHER INFORMATION: Chemically synthesized peptide

<400> SEQUENCE: 24

Ile Val Asp
1

<210> SEQ ID NO 25
<211> LENGTH: 4
<212> TYPE: PRT
<213> ORGANISM: Artificial Sequence
<220> FEATURE:
<223> OTHER INFORMATION: Chemically synthesized peptide
```

```
<400> SEQUENCE: 25

Ile Ile Ile Asp
1

<210> SEQ ID NO 26
<211> LENGTH: 4
<212> TYPE: PRT
<213> ORGANISM: Artificial Sequence
<220> FEATURE:
<223> OTHER INFORMATION: Chemically synthesized peptide

<400> SEQUENCE: 26

Ile Ile Ile Asp
1

<210> SEQ ID NO 27
<211> LENGTH: 4
<212> TYPE: PRT
<213> ORGANISM: Artificial Sequence
<220> FEATURE:
<223> OTHER INFORMATION: Chemically synthesized peptide

<400> SEQUENCE: 27

Ile Ile Ile Lys
1

<210> SEQ ID NO 28
<211> LENGTH: 4
<212> TYPE: PRT
<213> ORGANISM: Artificial Sequence
<220> FEATURE:
<223> OTHER INFORMATION: Chemically synthesized peptide

<400> SEQUENCE: 28

Ile Ile Ile Lys
1

<210> SEQ ID NO 29
<211> LENGTH: 3
<212> TYPE: PRT
<213> ORGANISM: Artificial Sequence
<220> FEATURE:
<223> OTHER INFORMATION: Chemically synthesized peptide

<400> SEQUENCE: 29

Ile Ile Asp
1

<210> SEQ ID NO 30
<211> LENGTH: 3
<212> TYPE: PRT
<213> ORGANISM: Artificial Sequence
<220> FEATURE:
<223> OTHER INFORMATION: Chemically synthesized peptide

<400> SEQUENCE: 30

Ile Ile Asp
1

<210> SEQ ID NO 31
<211> LENGTH: 7
<212> TYPE: PRT
<213> ORGANISM: Artificial Sequence
<220> FEATURE:
<223> OTHER INFORMATION: Chemically synthesized peptide
```

```
<400> SEQUENCE: 31

Leu Ile Val Ala Gly Asp Asp
1               5

<210> SEQ ID NO 32
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 32

Leu Ala Val Ala Gly Asp
1               5

<210> SEQ ID NO 33
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 33

Leu Ile Val Ala Ala Asp
1               5

<210> SEQ ID NO 34
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 34

Ala Ile Val Ala Gly Ser
1               5

<210> SEQ ID NO 35
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 35

Ile Leu Val Ala Gly Ser
1               5

<210> SEQ ID NO 36
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 36

Leu Ile Val Ala Gly Thr
1               5

<210> SEQ ID NO 37
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 37
```

Ala Ile Val Ala Gly Thr
1               5

<210> SEQ ID NO 38
<211> LENGTH: 7
<212> TYPE: PRT
<213> ORGANISM: Artificial Sequence
<220> FEATURE:
<223> OTHER INFORMATION: Chemically synthesized peptide

<400> SEQUENCE: 38

Leu Ile Val Ala Gly Glu Glu
1               5

<210> SEQ ID NO 39
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 39

Leu Ile Val Ala Gly Lys
1               5

<210> SEQ ID NO 40
<211> LENGTH: 5
<212> TYPE: PRT
<213> ORGANISM: Artificial Sequence
<220> FEATURE:
<223> OTHER INFORMATION: Chemically synthesized peptide

<400> SEQUENCE: 40

Leu Ile Val Ala Asp
1               5

<210> SEQ ID NO 41
<211> LENGTH: 5
<212> TYPE: PRT
<213> ORGANISM: Artificial Sequence
<220> FEATURE:
<223> OTHER INFORMATION: Chemically synthesized peptide

<400> SEQUENCE: 41

Leu Ile Val Gly Asp
1               5

<210> SEQ ID NO 42
<211> LENGTH: 3
<212> TYPE: PRT
<213> ORGANISM: Artificial Sequence
<220> FEATURE:
<223> OTHER INFORMATION: Chemically synthesized peptide

<400> SEQUENCE: 42

Ile Val Asp
1

<210> SEQ ID NO 43
<211> LENGTH: 7
<212> TYPE: PRT
<213> ORGANISM: Artificial Sequence
<220> FEATURE:
<223> OTHER INFORMATION: Chemically synthesized peptide

<400> SEQUENCE: 43

Leu Ile Val Ala Gly Lys Cys
1               5

<210> SEQ ID NO 44
<211> LENGTH: 7
<212> TYPE: PRT
<213> ORGANISM: Artificial Sequence
<220> FEATURE:
<223> OTHER INFORMATION: Chemically synthesized peptide

<400> SEQUENCE: 44

Leu Ile Val Ala Gly Ser Cys
1               5

<210> SEQ ID NO 45
<211> LENGTH: 7
<212> TYPE: PRT
<213> ORGANISM: Artificial Sequence
<220> FEATURE:
<223> OTHER INFORMATION: Chemically synthesized peptide

<400> SEQUENCE: 45

Leu Ile Val Ala Gly Asp Cys
1               5

<210> SEQ ID NO 46
<211> LENGTH: 7
<212> TYPE: PRT
<213> ORGANISM: Artificial Sequence
<220> FEATURE:
<223> OTHER INFORMATION: Chemically synthesized peptide

<400> SEQUENCE: 46

Ile Leu Val Ala Gly Lys Cys
1               5

<210> SEQ ID NO 47
<211> LENGTH: 7
<212> TYPE: PRT
<213> ORGANISM: Artificial Sequence
<220> FEATURE:
<223> OTHER INFORMATION: Chemically synthesized peptide

<400> SEQUENCE: 47

Ile Leu Val Ala Gly Asp Cys
1               5

<210> SEQ ID NO 48
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 48

Leu Ile Val Ala Gly Cys
1               5

<210> SEQ ID NO 49
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 49

Ala Ile Val Ala Gly Cys

```
1               5

<210> SEQ ID NO 50
<211> LENGTH: 6
<212> TYPE: PRT
<213> ORGANISM: Artificial Sequence
<220> FEATURE:
<223> OTHER INFORMATION: Chemically synthesized peptide

<400> SEQUENCE: 50

Ile Leu Val Ala Gly Cys
1               5

<210> SEQ ID NO 51
<211> LENGTH: 4
<212> TYPE: PRT
<213> ORGANISM: Artificial Sequence
<220> FEATURE:
<223> OTHER INFORMATION: Chemically synthesized peptide

<400> SEQUENCE: 51

Ile Val Lys Cys
1

<210> SEQ ID NO 52
<211> LENGTH: 4
<212> TYPE: PRT
<213> ORGANISM: Artificial Sequence
<220> FEATURE:
<223> OTHER INFORMATION: Chemically synthesized peptide

<400> SEQUENCE: 52

Ile Val Asp Cys
1

<210> SEQ ID NO 53
<211> LENGTH: 4
<212> TYPE: PRT
<213> ORGANISM: Artificial Sequence
<220> FEATURE:
<223> OTHER INFORMATION: Chemically synthesized peptide

<400> SEQUENCE: 53

Ile Val Ser Cys
1

<210> SEQ ID NO 54
<211> LENGTH: 5
<212> TYPE: PRT
<213> ORGANISM: Artificial Sequence
<220> FEATURE:
<223> OTHER INFORMATION: Chemically synthesized peptide

<400> SEQUENCE: 54

Leu Ile Val Ala Gly
1               5

<210> SEQ ID NO 55
<211> LENGTH: 5
<212> TYPE: PRT
<213> ORGANISM: Artificial Sequence
<220> FEATURE:
<223> OTHER INFORMATION: Chemically synthesized peptide

<400> SEQUENCE: 55

Ile Leu Val Ala Gly
1               5
```

```
<210> SEQ ID NO 56
<211> LENGTH: 5
<212> TYPE: PRT
<213> ORGANISM: Artificial Sequence
<220> FEATURE:
<223> OTHER INFORMATION: Chemically synthesized peptide

<400> SEQUENCE: 56

Leu Ile Val Ala Ala
1               5

<210> SEQ ID NO 57
<211> LENGTH: 5
<212> TYPE: PRT
<213> ORGANISM: Artificial Sequence
<220> FEATURE:
<223> OTHER INFORMATION: Chemically synthesized peptide

<400> SEQUENCE: 57

Leu Ala Val Ala Gly
1               5

<210> SEQ ID NO 58
<211> LENGTH: 4
<212> TYPE: PRT
<213> ORGANISM: Artificial Sequence
<220> FEATURE:
<223> OTHER INFORMATION: Chemically synthesized peptide

<400> SEQUENCE: 58

Ile Val Ala Gly
1

<210> SEQ ID NO 59
<211> LENGTH: 4
<212> TYPE: PRT
<213> ORGANISM: Artificial Sequence
<220> FEATURE:
<223> OTHER INFORMATION: Chemically synthesized peptide

<400> SEQUENCE: 59

Leu Ile Val Ala
1

<210> SEQ ID NO 60
<211> LENGTH: 4
<212> TYPE: PRT
<213> ORGANISM: Artificial Sequence
<220> FEATURE:
<223> OTHER INFORMATION: Chemically synthesized peptide

<400> SEQUENCE: 60

Leu Ile Val Gly
1
```